United States Patent
Barthe et al.

(10) Patent No.: US 10,010,724 B2
(45) Date of Patent: *Jul. 3, 2018

(54) ULTRASOUND PROBE FOR TREATING SKIN LAXITY

(71) Applicant: Guided Therapy Systems, L.L.C., Mesa, AZ (US)

(72) Inventors: Peter G. Barthe, Phoenix, AZ (US); Michael H. Slayton, Tempe, AZ (US); Inder Raj S. Makin, Mesa, AZ (US)

(73) Assignee: Guided Therapy Systems, L.L.C., Mesa, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/821,070

(22) Filed: Nov. 22, 2017

(65) Prior Publication Data

US 2018/0085607 A1    Mar. 29, 2018

Related U.S. Application Data

(63) Continuation of application No. 15/625,700, filed on Jun. 16, 2017, now Pat. No. 9,827,449, which is a
(Continued)

(51) Int. Cl.
*A61N 7/02* (2006.01)
*A61B 5/00* (2006.01)
(Continued)

(52) U.S. Cl.
CPC .............. *A61N 7/02* (2013.01); *A61B 5/682* (2013.01); *A61B 5/6842* (2013.01); *A61B 8/08* (2013.01);
(Continued)

(58) Field of Classification Search
CPC .... A61N 7/02; A61N 7/00; A61N 2007/0008; A61N 2007/0034; A61N 2007/0052;
(Continued)

(56) References Cited

U.S. PATENT DOCUMENTS 2,427,348 A    9/1947   Bond et al.
2,792,829 A    2/1952   Calosi
(Continued)

FOREIGN PATENT DOCUMENTS

CN    104027893    9/2014
DE    4029175      3/1992
(Continued)

OTHER PUBLICATIONS

Ulthera Exhibit 1025, Ulthera Oral Proceeding Demonstrative Slides (filed Oct. 2, 2017 in re IPR2016-01459).
(Continued)

*Primary Examiner* — Bo J Peng
(74) *Attorney, Agent, or Firm* — Knobbe Martens Olson & Bear LLP

(57) ABSTRACT

A probe for ultrasound treatment of skin laxity are provided. Systems and methods can include ultrasound imaging of the region of interest for localization of the treatment area, delivering ultrasound energy at a depth and pattern to achieve the desired therapeutic effects, and/or monitoring the treatment area to assess the results and/or provide feedback. In an embodiment, a treatment system and method can be configured for producing arrays of sub-millimeter and larger zones of thermal ablation to treat the epidermal, superficial dermal, mid-dermal or deep dermal components of tissue.

20 Claims, 22 Drawing Sheets

Related U.S. Application Data continuation of application No. 15/248,407, filed on Aug. 26, 2016, now Pat. No. 9,694,211, which is a continuation of application No. 14/692,114, filed on Apr. 21, 2015, now Pat. No. 9,427,600, which is a continuation of application No. 14/169,709, filed on Jan. 31, 2014, now Pat. No. 9,039,619, which is a continuation of application No. 13/230,498, filed on Sep. 12, 2011, now Pat. No. 8,641,622, which is a continuation of application No. 11/163,150, filed on Oct. 6, 2005, now Pat. No. 8,066,641.

(60) Provisional application No. 60/617,295, filed on Oct. 7, 2004.

(51) Int. Cl.

| | |
|---|---|
| A61B 8/08 | (2006.01) |
| A61B 8/12 | (2006.01) |
| A61B 8/13 | (2006.01) |
| A61B 8/00 | (2006.01) |
| A61B 17/32 | (2006.01) |
| A61H 23/02 | (2006.01) |
| G01S 15/89 | (2006.01) |
| A61N 7/00 | (2006.01) |

(52) U.S. Cl.
CPC ............ *A61B 8/0858* (2013.01); *A61B 8/12* (2013.01); *A61B 8/13* (2013.01); *A61B 8/4483* (2013.01); *A61B 8/461* (2013.01); *A61B 8/483* (2013.01); *A61B 8/546* (2013.01); *A61B 17/320068* (2013.01); *A61H 23/0245* (2013.01); *A61N 7/00* (2013.01); *G01S 15/8909* (2013.01); *A61B 8/4209* (2013.01); *A61B 8/4281* (2013.01); *A61B 8/4455* (2013.01); *A61H 2201/5007* (2013.01); *A61N 2007/0008* (2013.01); *A61N 2007/0034* (2013.01); *A61N 2007/0052* (2013.01); *A61N 2007/027* (2013.01)

(58) Field of Classification Search
CPC ............ A61N 2007/027; A61B 5/682; A61B 5/6842; A61B 8/08; A61B 8/0858; A61B 8/12; A61B 8/13; A61B 8/4483; A61B 8/461; A61B 8/483; A61B 8/546; A61B 17/320068; A61H 23/0245; A61H 2201/5007; G01S 15/8909

See application file for complete search history.

(56) References Cited

U.S. PATENT DOCUMENTS

| | | |
|---|---|---|
| 3,913,386 A | 10/1975 | Saglio |
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto |
| 4,151,834 A | 5/1979 | Sato et al. |
| 4,166,967 A | 9/1979 | Benes et al. |
| 4,211,948 A | 7/1980 | Smith et al. |
| 4,211,949 A | 7/1980 | Brisken et al. |
| 4,213,344 A | 7/1980 | Rose |
| 4,276,491 A | 6/1981 | Daniel |
| 4,315,514 A | 2/1982 | Drewes et al. |
| 4,325,381 A | 4/1982 | Glenn |
| 4,343,301 A | 8/1982 | Indech |
| 4,372,296 A | 2/1983 | Fahim |
| 4,379,145 A | 4/1983 | Masuho et al. |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Taenzer |
| 4,431,008 A | 2/1984 | Wanner et al. |
| 4,441,486 A | 4/1984 | Pounds |
| 4,452,084 A | 6/1984 | Taenzer |
| 4,484,569 A | 11/1984 | Driller |
| 4,507,582 A | 3/1985 | Glenn |
| 4,513,749 A | 4/1985 | Kino |
| 4,513,750 A | 4/1985 | Heyman et al. |
| 4,527,550 A | 7/1985 | Ruggera et al. |
| 4,528,979 A | 7/1985 | Marchenko |
| 4,534,221 A | 8/1985 | Fife et al. |
| 4,566,459 A | 1/1986 | Umemura et al. |
| 4,567,895 A | 2/1986 | Putzke |
| 4,586,512 A | 5/1986 | Do-Huu |
| 4,601,296 A | 7/1986 | Yerushalmi |
| 4,620,546 A | 11/1986 | Aida et al. |
| 4,637,256 A | 1/1987 | Sugiyama et al. |
| 4,646,756 A | 3/1987 | Watmough |
| 4,663,358 A | 5/1987 | Hyon |
| 4,668,516 A | 5/1987 | Duraffourd et al. |
| 4,672,591 A | 6/1987 | Breimesser et al. |
| 4,680,499 A | 7/1987 | Umemura et al. |
| 4,697,588 A | 10/1987 | Reichenberger |
| 4,754,760 A | 7/1988 | Fukukita et al. |
| 4,757,820 A | 7/1988 | Itoh |
| 4,771,205 A | 9/1988 | Mequio |
| 4,801,459 A | 1/1989 | Liburdy |
| 4,803,625 A | 2/1989 | Fu et al. |
| 4,807,633 A | 2/1989 | Fry |
| 4,817,615 A | 4/1989 | Fukukita et al. |
| 4,858,613 A | 8/1989 | Fry |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,881,212 A | 11/1989 | Takeuchi |
| 4,891,043 A | 1/1990 | Zeimer et al. |
| 4,893,624 A | 1/1990 | Lele |
| 4,896,673 A | 1/1990 | Rose |
| 4,900,540 A | 2/1990 | Ryan et al. |
| 4,901,729 A | 2/1990 | Saitoh |
| 4,917,096 A | 4/1990 | Englehart |
| 4,932,414 A | 6/1990 | Coleman et al. |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry |
| 4,955,365 A | 9/1990 | Fry |
| 4,958,626 A | 9/1990 | Nambu |
| 4,976,709 A | 12/1990 | Sand |
| 4,979,501 A | 12/1990 | Valchanov |
| 4,992,989 A | 2/1991 | Watanabe et al. |
| 5,012,797 A | 5/1991 | Liang |
| 5,018,508 A | 5/1991 | Fry et al. |
| 5,030,874 A | 7/1991 | Saito et al. |
| 5,036,855 A | 8/1991 | Fry |
| 5,040,537 A | 8/1991 | Katakura |
| 5,054,310 A | 10/1991 | Flynn |
| 5,054,470 A | 10/1991 | Fry |
| 5,054,491 A | 10/1991 | Saito et al. |
| 5,070,879 A | 12/1991 | Herres |
| 5,088,495 A | 2/1992 | Miyagawa |
| 5,115,814 A | 5/1992 | Griffith |
| 5,117,832 A | 6/1992 | Sanghvi |
| 5,123,418 A | 6/1992 | Saurel |
| 5,142,511 A | 8/1992 | Kanai et al. |
| 5,143,063 A | 9/1992 | Fellner |
| 5,143,074 A | 9/1992 | Dory |
| 5,149,319 A | 9/1992 | Unger |
| 5,150,711 A | 9/1992 | Dory |
| 5,150,714 A | 9/1992 | Green |
| 5,152,294 A | 10/1992 | Mochizuki et al. |
| 5,156,144 A | 10/1992 | Iwasaki |
| 5,158,536 A | 10/1992 | Sekins |
| 5,159,931 A | 11/1992 | Pini |
| 5,163,421 A | 11/1992 | Bernstein |

(56) References Cited

U.S. PATENT DOCUMENTS

| | | | |
|---|---|---|---|
| 5,163,436 A | 11/1992 | Saitoh et al. | |
| 5,178,135 A | 1/1993 | Uchiyama et al. | |
| 5,190,518 A | 3/1993 | Takasu | |
| 5,190,766 A | 3/1993 | Ishihara | |
| 5,191,880 A | 3/1993 | McLeod | |
| 5,205,287 A | 4/1993 | Erbel et al. | |
| 5,209,720 A | 5/1993 | Unger | |
| 5,212,671 A | 5/1993 | Fujii et al. | |
| 5,215,680 A | 6/1993 | D'Arrigo | |
| 5,224,467 A | 7/1993 | Oku | |
| 5,230,334 A | 7/1993 | Klopotek | |
| 5,230,338 A | 7/1993 | Allen et al. | |
| 5,247,924 A | 9/1993 | Suzuki et al. | |
| 5,255,681 A | 10/1993 | Ishimura et al. | |
| 5,257,970 A | 11/1993 | Dougherty | |
| 5,265,614 A | 11/1993 | Hayakawa | |
| 5,267,985 A | 12/1993 | Shimada | |
| 5,269,297 A | 12/1993 | Weng | |
| 5,282,797 A | 2/1994 | Chess | |
| 5,295,484 A | 3/1994 | Marcus | |
| 5,295,486 A | 3/1994 | Wollschlager et al. | |
| 5,304,169 A | 4/1994 | Sand | |
| 5,305,756 A | 4/1994 | Entrekin et al. | |
| 5,321,520 A | 6/1994 | Inga et al. | |
| 5,323,779 A | 6/1994 | Hardy et al. | |
| 5,327,895 A | 7/1994 | Hashimoto et al. | |
| 5,329,202 A | 7/1994 | Garlick et al. | |
| 5,348,016 A | 9/1994 | Unger et al. | |
| 5,358,466 A * | 10/1994 | Aida | A61B 17/2256 600/439 |
| 5,360,268 A | 11/1994 | Hayashi | |
| 5,370,121 A | 12/1994 | Reichenberger | |
| 5,370,122 A | 12/1994 | Kunig et al. | |
| 5,371,483 A | 12/1994 | Bhardwaj | |
| 5,375,602 A | 12/1994 | Lancee et al. | |
| 5,379,773 A | 1/1995 | Hornsby | |
| 5,380,280 A | 1/1995 | Peterson | |
| 5,380,519 A | 1/1995 | Schneider et al. | |
| 5,383,917 A | 1/1995 | Desai et al. | |
| 5,391,140 A | 2/1995 | Schaetzle et al. | |
| 5,391,197 A | 2/1995 | Burdette et al. | |
| 5,392,259 A | 2/1995 | Bolorforosh | |
| 5,396,143 A | 3/1995 | Seyed-Bolorforosh et al. | |
| 5,398,689 A | 3/1995 | Connor et al. | |
| 5,406,503 A | 4/1995 | Williams | |
| 5,413,550 A * | 5/1995 | Castel | A61H 23/0245 601/2 |
| 5,417,216 A | 5/1995 | Tanaka | |
| 5,419,327 A | 5/1995 | Rohwedder | |
| 5,423,220 A | 6/1995 | Finsterwald et al. | |
| 5,435,311 A | 7/1995 | Umemura | |
| 5,438,998 A | 8/1995 | Hanafy | |
| 5,443,068 A * | 8/1995 | Cline | A61B 5/0555 600/411 |
| 5,445,611 A | 8/1995 | Eppstein et al. | |
| 5,458,596 A | 10/1995 | Lax | |
| 5,460,179 A | 10/1995 | Okunuki et al. | |
| 5,460,595 A | 10/1995 | Hall et al. | |
| 5,469,854 A | 11/1995 | Unger et al. | |
| 5,471,488 A | 12/1995 | Fujio | |
| 5,472,405 A | 12/1995 | Buchholtz et al. | |
| 5,487,388 A | 1/1996 | Rello et al. | |
| 5,492,126 A | 2/1996 | Hennige | |
| 5,496,256 A | 3/1996 | Bock | |
| 5,501,655 A | 3/1996 | Rolt | |
| 5,503,152 A | 4/1996 | Oakley et al. | |
| 5,503,320 A | 4/1996 | Webster et al. | |
| 5,507,790 A | 4/1996 | Weiss | |
| 5,511,296 A | 4/1996 | Dias et al. | |
| 5,520,188 A | 5/1996 | Hennige | |
| 5,522,869 A | 6/1996 | Burdette | |
| 5,523,058 A | 6/1996 | Umemura et al. | |
| 5,524,620 A | 6/1996 | Rosenchein | |
| 5,524,624 A | 6/1996 | Tepper | |
| 5,524,625 A | 6/1996 | Okazaki | |
| 5,526,624 A | 6/1996 | Berg | |
| 5,526,812 A | 6/1996 | Dumoulin et al. | |
| 5,526,814 A | 6/1996 | Cline et al. | |
| 5,526,815 A | 6/1996 | Granz | |
| 5,529,070 A | 6/1996 | Augustine et al. | |
| 5,540,235 A | 7/1996 | Wilson | |
| 5,558,092 A | 9/1996 | Unger | |
| 5,560,362 A | 10/1996 | Sliwa et al. | |
| 5,575,291 A | 11/1996 | Hayakawa | |
| 5,575,807 A | 11/1996 | Faller | |
| 5,577,502 A | 11/1996 | Darrow et al. | |
| 5,577,507 A | 11/1996 | Snyder et al. | |
| 5,577,991 A | 11/1996 | Akui et al. | |
| 5,580,575 A | 12/1996 | Unger et al. | |
| 5,601,526 A * | 2/1997 | Chapelon | A61N 7/02 601/2 |
| 5,603,323 A | 2/1997 | Pflugrath et al. | |
| 5,605,154 A * | 2/1997 | Ries | G01S 7/52046 600/444 |
| 5,609,562 A | 3/1997 | Kaali | |
| 5,615,091 A | 3/1997 | Palatnik | |
| 5,618,275 A | 4/1997 | Bock | |
| 5,620,479 A | 4/1997 | Diederich | |
| 5,622,175 A | 4/1997 | Sudol et al. | |
| 5,617,858 A | 5/1997 | Taverna et al. | |
| 5,638,819 A | 6/1997 | Manwaring et al. | |
| 5,643,179 A * | 7/1997 | Fujimoto | A61N 7/02 601/2 |
| 5,644,085 A | 7/1997 | Lorraine et al. | |
| 5,647,373 A | 7/1997 | Paltieli | |
| 5,655,535 A | 8/1997 | Frlemel et al. | |
| 5,655,538 A | 8/1997 | Lorraine | |
| 5,657,760 A | 8/1997 | Ying | |
| 5,658,328 A | 8/1997 | Johnson | |
| 5,660,836 A * | 8/1997 | Knowlton | A61B 18/12 128/898 |
| 5,662,116 A | 9/1997 | Kondo | |
| 5,665,053 A | 9/1997 | Jacobs | |
| 5,665,141 A | 9/1997 | Vago | |
| 5,671,746 A | 9/1997 | Dreschel et al. | |
| 5,673,699 A | 10/1997 | Trahey et al. | |
| 5,676,692 A | 10/1997 | Sanghvi | |
| 5,685,820 A | 11/1997 | Riek et al. | |
| 5,690,608 A | 11/1997 | Watanabe | |
| 5,694,936 A | 12/1997 | Fujimoto | |
| 5,697,897 A | 12/1997 | Buchholtz | |
| 5,701,900 A | 12/1997 | Shehada et al. | |
| 5,704,361 A | 1/1998 | Seward et al. | |
| 5,706,252 A | 1/1998 | Le Verrier et al. | |
| 5,706,564 A | 1/1998 | Rhyne | |
| 5,715,823 A | 2/1998 | Wood et al. | |
| 5,720,287 A | 2/1998 | Chapelon et al. | |
| 5,722,411 A | 3/1998 | Suzuki | |
| 5,727,554 A | 3/1998 | Kalend et al. | |
| 5,735,280 A | 4/1998 | Sherman et al. | |
| 5,743,863 A | 4/1998 | Chapelon | |
| 5,746,005 A | 5/1998 | Steinberg | |
| 5,746,762 A | 5/1998 | Bass | |
| 5,748,767 A | 5/1998 | Raab | |
| 5,749,364 A | 5/1998 | Sliwa et al. | |
| 5,755,228 A | 5/1998 | Wilson et al. | |
| 5,755,753 A | 5/1998 | Knowlton | |
| 5,762,066 A | 6/1998 | Law | |
| 5,763,886 A | 6/1998 | Schulte | |
| 5,769,790 A | 6/1998 | Watkins | |
| 5,779,644 A | 7/1998 | Eberle et al. | |
| 5,792,058 A | 8/1998 | Lee | |
| 5,795,297 A | 8/1998 | Daigle | |
| 5,795,311 A | 8/1998 | Wess | |
| 5,810,009 A | 9/1998 | Mine et al. | |
| 5,810,888 A | 9/1998 | Fenn | |
| 5,814,599 A | 9/1998 | Mitragotri et al. | |
| 5,817,013 A | 10/1998 | Ginn et al. | |
| 5,817,021 A | 10/1998 | Reichenberger | |
| 5,820,564 A | 10/1998 | Slayton | |
| 5,823,962 A | 10/1998 | Schaetzle | |
| 5,827,204 A | 10/1998 | Grandia et al. | |
| 5,840,032 A | 11/1998 | Hatfield et al. | |
| 5,844,140 A | 12/1998 | Seale | |

(56) References Cited

U.S. PATENT DOCUMENTS

| | | | |
|---|---|---|---|
| 5,853,367 A | 12/1998 | Chalek et al. | |
| 5,869,751 A | 2/1999 | Bonin | |
| 5,871,524 A | 2/1999 | Knowlton | |
| 5,873,902 A | 2/1999 | Sanghvi | |
| 5,876,341 A | 3/1999 | Wang et al. | |
| 5,879,303 A | 3/1999 | Averkiou et al. | |
| 5,882,557 A | 3/1999 | Hayakawa | |
| 5,891,034 A | 4/1999 | Bucholz | |
| 5,895,356 A | 4/1999 | Andrus et al. | |
| 5,899,861 A | 5/1999 | Friemel et al. | |
| 5,904,659 A | 5/1999 | Duarte | |
| 5,919,219 A | 7/1999 | Knowlton | |
| 5,923,099 A | 7/1999 | Bilir | |
| 5,924,989 A | 7/1999 | Polz | |
| 5,928,169 A | 7/1999 | Schatzle et al. | |
| 5,931,805 A | 8/1999 | Brisken | |
| 5,938,606 A | 8/1999 | Bonnefous | |
| 5,938,612 A | 8/1999 | Kline-Schoder | |
| 5,948,011 A | 9/1999 | Knowlton | |
| 5,957,844 A | 9/1999 | Dekel | |
| 5,957,882 A | 9/1999 | Nita et al. | |
| 5,957,941 A | 9/1999 | Ream | |
| 5,964,707 A | 10/1999 | Fenster et al. | |
| 5,967,980 A | 10/1999 | Ferre et al. | |
| 5,968,034 A | 10/1999 | Fullmer | |
| 5,971,949 A | 10/1999 | Levin | |
| 5,977,538 A | 11/1999 | Unger et al. | |
| 5,984,881 A * | 11/1999 | Ishibashi | A61B 17/2256 601/2 |
| 5,984,882 A | 11/1999 | Rosenchein | |
| 5,990,598 A | 11/1999 | Sudol et al. | |
| 5,997,471 A | 12/1999 | Gumb et al. | |
| 5,997,497 A | 12/1999 | Nita et al. | |
| 5,999,843 A | 12/1999 | Anbar | |
| 6,004,262 A | 12/1999 | Putz et al. | |
| 6,007,499 A | 12/1999 | Martin et al. | |
| 6,013,032 A | 1/2000 | Savord | |
| 6,014,473 A | 1/2000 | Hossack et al. | |
| 6,016,255 A | 1/2000 | Bolan et al. | |
| 6,019,724 A | 2/2000 | Gronningsaeter et al. | |
| 6,022,308 A | 2/2000 | Williams | |
| 6,022,327 A | 2/2000 | Chang | |
| 6,030,374 A | 2/2000 | McDaniel | |
| 6,036,646 A | 3/2000 | Barthe | |
| 6,039,048 A | 3/2000 | Silberg | |
| 6,039,689 A | 3/2000 | Lizzi | |
| 6,042,556 A * | 3/2000 | Beach | A61N 7/02 600/437 |
| 6,049,159 A | 4/2000 | Barthe | |
| 6,050,943 A | 4/2000 | Slayton | |
| 6,059,727 A | 5/2000 | Fowlkes | |
| 6,071,239 A | 6/2000 | Cribbs | |
| 6,080,108 A | 6/2000 | Dunham | |
| 6,083,148 A | 7/2000 | Williams | |
| 6,086,535 A | 7/2000 | Ishibashi | |
| 6,086,580 A | 7/2000 | Mordon et al. | |
| 6,090,054 A | 7/2000 | Tagishi | |
| 6,093,148 A * | 7/2000 | Fujimoto | A61N 7/00 600/438 |
| 6,093,883 A | 7/2000 | Sanghvi | |
| 6,101,407 A | 8/2000 | Groezinger | |
| 6,106,469 A | 8/2000 | Suzuki et al. | |
| 6,113,558 A | 9/2000 | Rosenchein | |
| 6,113,559 A | 9/2000 | Klopotek | |
| 6,120,452 A | 9/2000 | Barthe | |
| 6,123,081 A | 9/2000 | Durette | |
| 6,126,619 A | 10/2000 | Peterson et al. | |
| 6,135,971 A | 10/2000 | Hutchinson | |
| 6,139,499 A | 10/2000 | Wilk | |
| 6,159,150 A | 12/2000 | Yale et al. | |
| 6,171,244 B1 | 1/2001 | Finger et al. | |
| 6,176,840 B1 | 1/2001 | Nishimura | |
| 6,183,426 B1 | 2/2001 | Akisada | |
| 6,183,502 B1 | 2/2001 | Takeuchi | |
| 6,183,773 B1 | 2/2001 | Anderson | |
| 6,190,323 B1 | 2/2001 | Dias | |
| 6,190,336 B1 | 2/2001 | Duarte | |
| 6,193,658 B1 | 2/2001 | Wendelken | |
| 6,198,956 B1 | 3/2001 | Dunne | |
| 6,210,327 B1 | 4/2001 | Brackett et al. | |
| 6,213,948 B1 | 4/2001 | Barthe | |
| 6,216,029 B1 | 4/2001 | Paltieli | |
| 6,233,476 B1 | 5/2001 | Strommer et al. | |
| 6,234,990 B1 | 5/2001 | Rowe et al. | |
| 6,241,753 B1 * | 6/2001 | Knowlton | A61B 18/12 128/898 |
| 6,246,898 B1 | 6/2001 | Vesely et al. | |
| 6,251,074 B1 | 6/2001 | Averkiou et al. | |
| 6,251,088 B1 | 6/2001 | Kaufman et al. | |
| 6,268,405 B1 | 7/2001 | Yao | |
| 6,273,864 B1 | 8/2001 | Duarte | |
| 6,280,402 B1 | 8/2001 | Ishibashi et al. | |
| 6,287,257 B1 | 9/2001 | Matichuk | |
| 6,287,304 B1 | 9/2001 | Eggers et al. | |
| 6,296,619 B1 | 10/2001 | Brisken | |
| 6,301,989 B1 | 10/2001 | Brown et al. | |
| 6,307,302 B1 | 10/2001 | Toda | |
| 6,309,355 B1 | 10/2001 | Cain et al. | |
| 6,311,090 B1 | 10/2001 | Knowlton | |
| 6,315,741 B1 * | 11/2001 | Martin | A61B 8/4254 601/3 |
| 6,322,509 B1 | 11/2001 | Pan et al. | |
| 6,322,532 B1 | 11/2001 | D'Sa | |
| 6,325,540 B1 | 12/2001 | Lounsberry et al. | |
| 6,325,758 B1 | 12/2001 | Carol et al. | |
| 6,325,769 B1 | 12/2001 | Klopotek | |
| 6,325,798 B1 | 12/2001 | Edwards et al. | |
| 6,350,276 B1 | 2/2002 | Knowlton | |
| 6,356,780 B1 | 3/2002 | Licato et al. | |
| 6,361,531 B1 | 3/2002 | Hissong | |
| 6,370,411 B1 | 4/2002 | Osadchy et al. | |
| 6,375,672 B1 | 4/2002 | Aksan | |
| 6,377,854 B1 | 4/2002 | Knowlton | |
| 6,377,855 B1 | 4/2002 | Knowlton | |
| 6,381,497 B1 | 4/2002 | Knowlton | |
| 6,381,498 B1 | 4/2002 | Knowlton | |
| 6,387,380 B1 | 5/2002 | Knowlton | |
| 6,390,982 B1 | 5/2002 | Bova et al. | |
| 6,405,090 B1 | 6/2002 | Knowlton | |
| 6,409,720 B1 | 6/2002 | Hissong | |
| 6,413,216 B1 | 7/2002 | Cain et al. | |
| 6,413,253 B1 | 7/2002 | Koop | |
| 6,413,254 B1 | 7/2002 | Hissong | |
| 6,419,648 B1 | 7/2002 | Vitek | |
| 6,423,007 B2 | 7/2002 | Lizzi et al. | |
| 6,425,865 B1 | 7/2002 | Salcudean | |
| 6,425,867 B1 | 7/2002 | Vaezy | |
| 6,425,912 B1 | 7/2002 | Knowlton | |
| 6,428,477 B1 | 8/2002 | Mason | |
| 6,428,532 B1 | 8/2002 | Doukas | |
| 6,430,446 B1 | 8/2002 | Knowlton | |
| 6,432,057 B1 | 8/2002 | Mazess et al. | |
| 6,432,067 B1 | 8/2002 | Martin | |
| 6,432,101 B1 | 8/2002 | Weber | |
| 6,436,061 B1 | 8/2002 | Costantino | |
| 6,438,424 B1 | 8/2002 | Knowlton | |
| 6,440,071 B1 | 8/2002 | Slayton | |
| 6,440,121 B1 | 8/2002 | Weber | |
| 6,443,914 B1 | 9/2002 | Costantino | |
| 6,447,443 B1 | 9/2002 | Keogh et al. | |
| 6,451,013 B1 | 9/2002 | Bays et al. | |
| 6,453,202 B1 | 9/2002 | Knowlton | |
| 6,461,304 B1 | 10/2002 | Tanaka et al. | |
| 6,461,378 B1 | 10/2002 | Knowlton | |
| 6,470,216 B1 | 10/2002 | Knowlton | |
| 6,338,716 B1 | 11/2002 | Hossack et al. | |
| 6,488,626 B1 | 12/2002 | Lizzi | |
| 6,491,657 B2 | 12/2002 | Rowe | |
| 6,500,121 B1 | 12/2002 | Slayton | |
| 6,500,141 B1 | 12/2002 | Irion | |
| 6,506,171 B1 | 1/2003 | Vitek et al. | |
| 6,508,774 B1 | 1/2003 | Acker | |
| 6,511,427 B1 | 1/2003 | Sliwa, Jr. et al. | |
| 6,511,428 B1 | 1/2003 | Azuma | |

(56) References Cited

U.S. PATENT DOCUMENTS

| | | |
|---|---|---|
| 6,514,244 B2 | 2/2003 | Pope |
| 6,517,484 B1 | 2/2003 | Wilk |
| 6,524,250 B1 | 2/2003 | Weber |
| 6,666,835 B2 | 3/2003 | Martin |
| 6,540,679 B2 | 4/2003 | Slayton |
| 6,540,685 B1 | 4/2003 | Rhoads et al. |
| 6,540,700 B1 | 4/2003 | Fujimoto et al. |
| 6,547,788 B1 | 4/2003 | Maguire et al. |
| 6,554,771 B1 | 4/2003 | Buil et al. |
| 6,569,099 B1 | 5/2003 | Babaev |
| 6,569,108 B2 | 5/2003 | Sarvazyan et al. |
| 6,572,552 B2 | 6/2003 | Fukukita |
| 6,575,956 B1 | 6/2003 | Brisken et al. |
| 6,595,934 B1 | 7/2003 | Hissong |
| 6,599,256 B1 | 7/2003 | Acker |
| 6,605,080 B1 | 8/2003 | Altshuler et al. |
| 6,607,498 B2 | 8/2003 | Eshel |
| 6,618,620 B1 | 9/2003 | Freundlich et al. |
| 6,623,430 B1 | 9/2003 | Slayton |
| 6,626,854 B2 | 9/2003 | Friedman |
| 6,626,855 B1 | 9/2003 | Weng |
| 6,638,226 B2 | 10/2003 | He et al. |
| 6,645,150 B2 | 11/2003 | Angelsen et al. |
| 6,645,162 B2 | 11/2003 | Friedman |
| 6,662,054 B2 | 12/2003 | Kreindel |
| 6,663,627 B2 | 12/2003 | Francischelli |
| 6,665,806 B1 | 12/2003 | Shimizu |
| 6,669,638 B1 | 12/2003 | Miller |
| 6,685,639 B1 | 2/2004 | Wang et al. |
| 6,685,640 B1 | 2/2004 | Fry |
| 6,692,450 B1 | 2/2004 | Coleman |
| 6,699,237 B2 | 3/2004 | Weber |
| 6,716,184 B2 | 4/2004 | Vaezy et al. |
| 6,719,449 B1 | 4/2004 | Laughlin |
| 6,719,694 B2 | 4/2004 | Weng |
| 6,726,627 B1 | 4/2004 | Lizzi et al. |
| 6,733,449 B1 | 5/2004 | Krishnamurthy et al. |
| 6,749,624 B2 | 6/2004 | Knowlton |
| 6,772,490 B2 | 8/2004 | Toda |
| 6,773,409 B2 | 8/2004 | Truckai et al. |
| 6,775,404 B1 | 8/2004 | Pagoulatos et al. |
| 6,790,187 B2 | 9/2004 | Thompson et al. |
| 6,824,516 B2 | 11/2004 | Batten et al. |
| 6,825,176 B2 | 11/2004 | White et al. |
| 6,835,940 B2 | 12/2004 | Morikawa et al. |
| 6,846,290 B2 | 1/2005 | Lizzi et al. |
| 6,875,176 B2 | 4/2005 | Mourad et al. |
| 6,882,884 B1 | 4/2005 | Mosk et al. |
| 6,887,239 B2 | 5/2005 | Elstrom |
| 6,889,089 B2 | 5/2005 | Behl |
| 6,896,657 B2 | 5/2005 | Willis |
| 6,902,536 B2 | 6/2005 | Manna |
| 6,905,466 B2 | 6/2005 | Salgo |
| 6,918,907 B2 | 7/2005 | Kelly |
| 6,920,883 B2 | 7/2005 | Bessette |
| 6,921,371 B2 | 7/2005 | Wilson |
| 6,932,771 B2 | 8/2005 | Whitmore |
| 6,932,814 B2 | 8/2005 | Wood |
| 6,936,044 B2 | 8/2005 | McDaniel |
| 6,936,046 B2 | 8/2005 | Hissong |
| 6,945,937 B2 | 9/2005 | Culp et al. |
| 6,948,843 B2 | 9/2005 | Laugharn et al. |
| 6,953,941 B2 | 10/2005 | Nakano et al. |
| 6,958,043 B2 | 10/2005 | Hissong |
| 6,971,994 B1 | 12/2005 | Young et al. |
| 6,974,417 B2 | 12/2005 | Lockwood |
| 6,976,492 B2 | 12/2005 | Ingle |
| 6,992,305 B2 | 1/2006 | Maezawa et al. |
| 6,997,923 B2 | 2/2006 | Anderson |
| 7,006,874 B2 | 2/2006 | Knowlton |
| 7,020,528 B2 | 3/2006 | Neev |
| 7,022,089 B2 | 4/2006 | Ooba |
| 7,058,440 B2 | 6/2006 | Heuscher et al. |
| 7,063,666 B2 | 6/2006 | Weng |
| 7,070,565 B2 | 7/2006 | Vaezy et al. |
| 7,074,218 B2 | 7/2006 | Washington et al. |
| 7,094,252 B2 | 8/2006 | Koop |
| 7,108,663 B2 | 9/2006 | Talish et al. |
| 7,115,123 B2 | 10/2006 | Knowlton |
| 7,122,029 B2 | 10/2006 | Koop et al. |
| 7,142,905 B2 | 11/2006 | Slayton |
| 7,165,451 B1 | 1/2007 | Brooks et al. |
| 7,179,238 B2 | 2/2007 | Hissong |
| 7,189,230 B2 | 3/2007 | Knowlton |
| 7,229,411 B2 | 6/2007 | Slayton |
| 7,235,592 B2 | 6/2007 | Muratoglu |
| 7,258,674 B2 | 8/2007 | Cribbs |
| 7,273,459 B2 | 9/2007 | Desilets |
| 7,294,125 B2 | 11/2007 | Phalen et al. |
| 7,297,117 B2 | 11/2007 | Trucco |
| 7,303,555 B2 | 12/2007 | Makin et al. |
| 7,311,679 B2 | 12/2007 | Desilets et al. |
| 7,327,071 B2 | 2/2008 | Nishiyama et al. |
| 7,331,951 B2 | 2/2008 | Eshel et al. |
| 7,332,985 B2 | 2/2008 | Larson et al. |
| 7,338,434 B1 | 3/2008 | Haarstad et al. |
| 7,347,855 B2 | 3/2008 | Eshel |
| RE40,403 E | 6/2008 | Cho et al. |
| 7,393,325 B2 | 7/2008 | Barthe |
| 7,398,116 B2 | 7/2008 | Edwards |
| 7,399,279 B2 | 7/2008 | Abend et al. |
| 7,491,171 B2 | 2/2009 | Barthe et al. |
| 7,507,235 B2 | 3/2009 | Keogh et al. |
| 7,510,536 B2 | 3/2009 | Foley et al. |
| 7,517,315 B2 | 4/2009 | Willis |
| 7,530,356 B2 | 5/2009 | Slayton |
| 7,530,958 B2 | 5/2009 | Slayton |
| 7,532,201 B2 | 5/2009 | Quistgaard et al. |
| 7,571,336 B2 | 8/2009 | Barthe |
| 7,601,120 B2 | 10/2009 | Moilanen et al. |
| 7,615,015 B2 | 11/2009 | Coleman |
| 7,615,016 B2 | 11/2009 | Barthe |
| 7,631,611 B1 | 12/2009 | Dick et al. |
| 7,652,411 B2 | 1/2010 | Crunkilton et al. |
| 7,662,114 B2 | 2/2010 | Seip et al. |
| 7,674,257 B2 | 3/2010 | Pless et al. |
| 7,686,763 B2 | 3/2010 | Vaezy et al. |
| 7,713,203 B2 | 3/2010 | Lacoste et al. |
| 7,694,406 B2 | 4/2010 | Wildes et al. |
| 7,695,437 B2 | 4/2010 | Quistgaard et al. |
| 7,727,156 B2 | 6/2010 | Angelsen et al. |
| 7,758,524 B2 | 7/2010 | Barthe |
| 7,766,848 B2 | 8/2010 | Desilets et al. |
| 7,789,841 B2 | 9/2010 | Huckle et al. |
| 7,806,839 B2 | 10/2010 | Mast et al. |
| 7,815,570 B2 | 10/2010 | Eshel et al. |
| 7,819,826 B2 | 10/2010 | Diederich et al. |
| 7,828,734 B2 | 10/2010 | Azhari et al. |
| 7,824,348 B2 | 11/2010 | Barthe |
| 7,833,162 B2 | 11/2010 | Hasegawa et al. |
| 7,841,984 B2 | 11/2010 | Cribbs et al. |
| 7,846,096 B2 | 12/2010 | Mast et al. |
| 7,857,773 B2 | 12/2010 | Desilets et al. |
| 7,875,023 B2 | 1/2011 | Eshel et al. |
| 7,901,359 B2 | 3/2011 | Mandrusov et al. |
| 7,905,007 B2 | 3/2011 | Calisti et al. |
| 7,905,844 B2 | 3/2011 | Desilets et al. |
| 7,914,453 B2 | 3/2011 | Slayton et al. |
| 7,914,469 B2 | 3/2011 | Torbati |
| 7,955,281 B2 | 6/2011 | Pedersen et al. |
| 7,967,764 B2 | 6/2011 | Lidgren et al. |
| 7,967,839 B2 | 6/2011 | Flock et al. |
| 7,955,262 B2 | 7/2011 | Rosenberg |
| 7,993,289 B2 | 8/2011 | Quistgaard et al. |
| 8,057,465 B2 | 9/2011 | Sliwa, Jr. et al. |
| 8,057,389 B2 | 11/2011 | Barthe et al. |
| 8,066,641 B2 | 11/2011 | Barthe et al. |
| 8,123,707 B2 | 2/2012 | Huckle et al. |
| 8,128,618 B2 | 3/2012 | Gliklich et al. |
| 8,133,180 B2 | 3/2012 | Slayton et al. |
| 8,133,191 B2 | 3/2012 | Rosenberg et al. |
| 8,142,200 B2 | 3/2012 | Crunkilton et al. |
| 8,152,904 B2 | 4/2012 | Slobodzian et al. |
| 8,162,858 B2 | 4/2012 | Manna et al. |

(56) References Cited

U.S. PATENT DOCUMENTS

| | | |
|---|---|---|
| 8,166,332 B2 | 4/2012 | Barthe et al. |
| 8,182,428 B2 | 5/2012 | Angelsen et al. |
| 8,197,409 B2 | 6/2012 | Foley et al. |
| 8,206,299 B2 | 6/2012 | Foley et al. |
| 8,208,346 B2 | 6/2012 | Crunkilton |
| 8,211,017 B2 | 7/2012 | Foley et al. |
| 8,262,591 B2 | 9/2012 | Pedersen et al. |
| 8,262,650 B2 | 9/2012 | Zanelli et al. |
| 8,264,126 B2 | 9/2012 | Toda et al. |
| 8,273,037 B2 | 9/2012 | Kreindel et al. |
| 8,282,554 B2 | 10/2012 | Makin et al. |
| 8,292,835 B1 | 10/2012 | Cimino |
| 8,298,163 B1 | 10/2012 | Cimino |
| 8,333,700 B1 | 12/2012 | Barthe et al. |
| 8,334,637 B2 | 12/2012 | Crunkilton et al. |
| 8,337,407 B2 | 12/2012 | Quistgaard et al. |
| 8,343,051 B2 | 1/2013 | Desilets et al. |
| 8,454,540 B2 | 1/2013 | Eshel et al. |
| 8,366,622 B2 | 2/2013 | Slayton et al. |
| 8,398,549 B2 | 3/2013 | Palmeri et al. |
| 8,409,097 B2 | 4/2013 | Slayton et al. |
| 8,425,435 B2 | 4/2013 | Wing et al. |
| 8,388,535 B2 | 5/2013 | Weng et al. |
| 8,444,562 B2 | 5/2013 | Barthe et al. |
| 8,460,193 B2 | 6/2013 | Barthe et al. |
| 8,480,585 B2 | 7/2013 | Slayton et al. |
| 8,506,486 B2 | 8/2013 | Slayton et al. |
| 8,512,250 B2 | 8/2013 | Quistgaard et al. |
| 8,523,775 B2 | 9/2013 | Barthe et al. |
| 8,535,228 B2 | 9/2013 | Slayton et al. |
| 8,570,837 B2 | 10/2013 | Toda et al. |
| 8,573,392 B2 | 11/2013 | Bennett et al. |
| 8,583,211 B2 | 11/2013 | Salomir et al. |
| 8,585,618 B2 | 11/2013 | Hunziker et al. |
| 8,604,672 B2 | 12/2013 | Toda et al. |
| 8,622,937 B2 | 1/2014 | Weng et al. |
| 8,636,665 B2 | 1/2014 | Slayton et al. |
| 8,640,193 B2 | 1/2014 | Shigeeda |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,708,935 B2 | 4/2014 | Barthe et al. |
| 8,715,186 B2 | 5/2014 | Slayton et al. |
| 8,726,781 B2 | 5/2014 | Eckhoff et al. |
| 8,728,071 B2 | 5/2014 | Lischinsky et al. |
| 8,753,295 B2 | 6/2014 | Thierman |
| 8,758,253 B2 | 6/2014 | Sano et al. |
| 8,836,203 B2 | 9/2014 | Nobles et al. |
| 8,857,438 B2 | 10/2014 | Barthe et al. |
| 8,858,471 B2 | 10/2014 | Barthe et al. |
| 8,915,853 B2 | 12/2014 | Barthe et al. |
| 8,915,854 B2 | 12/2014 | Slayton et al. |
| 8,915,870 B2 | 12/2014 | Barthe et al. |
| 8,920,320 B2 | 12/2014 | Stecco et al. |
| 8,920,324 B2 | 12/2014 | Slayton et al. |
| 8,926,533 B2 | 1/2015 | Bockenstedt et al. |
| 8,932,224 B2 | 1/2015 | Barthe et al. |
| 8,932,238 B2 | 1/2015 | Wing et al. |
| 8,968,205 B2 | 3/2015 | Zeng et al. |
| 9,011,336 B2 | 4/2015 | Slayton et al. |
| 9,039,617 B2 | 5/2015 | Slayton et al. |
| 9,039,619 B2 | 5/2015 | Barthe et al. |
| 9,095,697 B2 | 8/2015 | Barthe et al. |
| 9,114,247 B2 | 8/2015 | Barthe et al. |
| 9,216,276 B2 | 12/2015 | Slayton et al. |
| 9,272,162 B2 | 3/2016 | Slayton et al. |
| 9,283,409 B2 | 3/2016 | Slayton et al. |
| 9,283,410 B2 | 3/2016 | Slayton et al. |
| 9,320,537 B2 | 4/2016 | Slayton et al. |
| 9,421,029 B2 | 8/2016 | Barthe et al. |
| 9,427,600 B2 | 8/2016 | Barthe et al. |
| 9,427,601 B2 | 8/2016 | Barthe et al. |
| 9,440,096 B2 | 9/2016 | Barthe et al. |
| 9,510,802 B2 | 12/2016 | Barthe et al. |
| 9,522,290 B2 | 12/2016 | Slayton et al. |
| 9,533,175 B2 | 1/2017 | Slayton et al. |
| 9,694,211 B2 | 7/2017 | Barthe et al. |
| 9,694,212 B2 | 7/2017 | Barthe et al. |
| 9,707,412 B2 | 7/2017 | Slayton et al. |
| 9,713,731 B2 | 7/2017 | Slayton et al. |
| 9,802,063 B2 | 10/2017 | Barthe et al. |
| 9,827,449 B2 | 11/2017 | Barthe et al. |
| 9,827,450 B2 | 11/2017 | Slayton et al. |
| 9,833,639 B2 | 12/2017 | Slayton et al. |
| 9,833,640 B2 | 12/2017 | Barthe et al. |
| 2001/0009997 A1 | 7/2001 | Pope |
| 2001/0009999 A1 | 7/2001 | Kaufman et al. |
| 2001/0014780 A1 | 8/2001 | Martin |
| 2001/0014819 A1 | 8/2001 | Ingle |
| 2001/0031922 A1* | 10/2001 | Weng ............... A61B 17/0057 600/439 |
| 2001/0039380 A1 | 11/2001 | Larson et al. |
| 2001/0041880 A1 | 11/2001 | Brisken |
| 2002/0000763 A1 | 1/2002 | Jones |
| 2002/0002345 A1 | 1/2002 | Marlinghaus |
| 2002/0040199 A1 | 4/2002 | Klopotek |
| 2002/0040442 A1 | 4/2002 | Ishidera |
| 2002/0055702 A1 | 5/2002 | Atala |
| 2002/0062077 A1 | 5/2002 | Emmenegger |
| 2002/0062142 A1 | 5/2002 | Knowlton |
| 2002/0072691 A1 | 6/2002 | Thompson et al. |
| 2002/0082528 A1 | 6/2002 | Friedman |
| 2002/0082529 A1 | 6/2002 | Suorsa et al. |
| 2002/0082589 A1 | 6/2002 | Friedman |
| 2002/0087080 A1 | 7/2002 | Slayton |
| 2002/0095143 A1 | 7/2002 | Key |
| 2002/0099094 A1 | 7/2002 | Anderson |
| 2002/0115917 A1 | 8/2002 | Honda et al. |
| 2002/0128639 A1 | 8/2002 | Pless et al. |
| 2002/0128648 A1 | 9/2002 | Weber |
| 2002/0143252 A1 | 10/2002 | Dunne et al. |
| 2002/0156400 A1 | 10/2002 | Babaev |
| 2002/0161357 A1 | 10/2002 | Anderson |
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1 | 11/2002 | Neev |
| 2002/0173721 A1 | 11/2002 | Grunwald et al. |
| 2002/0193784 A1 | 12/2002 | McHale et al. |
| 2002/0193831 A1 | 12/2002 | Smith |
| 2003/0009153 A1 | 1/2003 | Brisken et al. |
| 2003/0014039 A1 | 1/2003 | Barzell et al. |
| 2003/0018255 A1 | 1/2003 | Martin |
| 2003/0018270 A1 | 1/2003 | Makin et al. |
| 2003/0023283 A1* | 1/2003 | McDaniel ............... A61K 8/02 607/88 |
| 2003/0028111 A1 | 2/2003 | Vaezy et al. |
| 2003/0028113 A1 | 2/2003 | Gilbert et al. |
| 2003/0032900 A1 | 2/2003 | Ella |
| 2003/0036706 A1 | 2/2003 | Slayton et al. |
| 2003/0040739 A1 | 2/2003 | Koop |
| 2003/0050678 A1 | 3/2003 | Sierra |
| 2003/0055308 A1 | 3/2003 | Friemel et al. |
| 2003/0055417 A1 | 3/2003 | Truckai et al. |
| 2003/0060736 A1 | 3/2003 | Martin et al. |
| 2003/0065313 A1 | 4/2003 | Koop |
| 2003/0066708 A1 | 4/2003 | Allison et al. |
| 2003/0073907 A1 | 4/2003 | Taylor |
| 2003/0074023 A1 | 4/2003 | Kaplan |
| 2003/0083536 A1 | 5/2003 | Eshel |
| 2003/0092988 A1 | 5/2003 | Makin |
| 2003/0097071 A1 | 5/2003 | Halmann et al. |
| 2003/0099383 A1 | 5/2003 | Lefebvre |
| 2003/0125629 A1 | 7/2003 | Ustuner |
| 2003/0135135 A1 | 7/2003 | Miwa et al. |
| 2003/0139790 A1 | 7/2003 | Ingle et al. |
| 2003/0149366 A1 | 8/2003 | Stringer et al. |
| 2003/0153961 A1 | 8/2003 | Babaev |
| 2003/0171678 A1 | 9/2003 | Batten et al. |
| 2003/0171701 A1 | 9/2003 | Babaev |
| 2003/0176790 A1 | 9/2003 | Slayton |

(56) References Cited

U.S. PATENT DOCUMENTS

| | | |
|---|---|---|
| 2003/0191396 A1 | 10/2003 | Sanghvi |
| 2003/0199794 A1 | 10/2003 | Sakurai et al. |
| 2003/0200481 A1 | 10/2003 | Stanley |
| 2003/0212129 A1 | 11/2003 | Liu et al. |
| 2003/0212351 A1 | 11/2003 | Hissong |
| 2003/0212393 A1 | 11/2003 | Knowlton |
| 2003/0216648 A1 | 11/2003 | Lizzi et al. |
| 2003/0216795 A1 | 11/2003 | Harth |
| 2003/0220536 A1 | 11/2003 | Hissong |
| 2003/0220585 A1 | 11/2003 | Hissong |
| 2003/0229331 A1 | 12/2003 | Brisken et al. |
| 2003/0233085 A1 | 12/2003 | Giammarusti |
| 2003/0236487 A1 | 12/2003 | Knowlton |
| 2004/0000316 A1 | 1/2004 | Knowlton |
| 2004/0001809 A1 | 1/2004 | Brisken |
| 2004/0002658 A1 | 1/2004 | Marian, Jr. |
| 2004/0002705 A1 | 1/2004 | Knowlton |
| 2004/0010222 A1 | 1/2004 | Nunomura et al. |
| 2004/0015079 A1 | 1/2004 | Berger et al. |
| 2004/0015106 A1 | 1/2004 | Coleman |
| 2004/0030227 A1 | 2/2004 | Littrup |
| 2004/0039312 A1 | 2/2004 | Hillstead |
| 2004/0039418 A1 | 2/2004 | Elstrom |
| 2004/0041563 A1 | 3/2004 | Lewin et al. |
| 2004/0041880 A1 | 3/2004 | Ikeda et al. |
| 2004/0042168 A1 | 3/2004 | Yang et al. |
| 2004/0044375 A1 | 3/2004 | Diederich et al. |
| 2004/0049134 A1 | 3/2004 | Tosaya et al. |
| 2004/0049734 A1 | 3/2004 | Tosaya et al. |
| 2004/0059266 A1 | 3/2004 | Fry |
| 2004/0068186 A1 | 4/2004 | Ishida et al. |
| 2004/0073079 A1 | 4/2004 | Altshuler et al. |
| 2004/0073113 A1 | 4/2004 | Salgo |
| 2004/0073115 A1 | 4/2004 | Horzewski et al. |
| 2004/0073116 A1 | 4/2004 | Smith |
| 2004/0073204 A1 | 4/2004 | Ryan et al. |
| 2004/0077977 A1 | 4/2004 | Ella et al. |
| 2004/0082857 A1 | 4/2004 | Schonenberger |
| 2004/0082859 A1 | 4/2004 | Schaer |
| 2004/0102697 A1 | 5/2004 | Evron |
| 2004/0105559 A1 | 6/2004 | Aylward et al. |
| 2004/0106867 A1 | 6/2004 | Eshel et al. |
| 2004/0122323 A1 | 6/2004 | Vortman et al. |
| 2004/0122493 A1 | 6/2004 | Ishibashi et al. |
| 2004/0143297 A1 | 7/2004 | Ramsey |
| 2004/0152982 A1 | 8/2004 | Hwang et al. |
| 2004/0158150 A1 | 8/2004 | Rabiner et al. |
| 2004/0186535 A1 | 9/2004 | Knowlton |
| 2004/0189155 A1 | 9/2004 | Funakubo |
| 2004/0206365 A1 | 10/2004 | Knowlton |
| 2004/0210214 A1 | 10/2004 | Knowlton |
| 2004/0217675 A1 | 11/2004 | Desilets |
| 2004/0249318 A1 | 12/2004 | Tanaka |
| 2004/0254620 A1 | 12/2004 | Lacoste |
| 2004/0267252 A1 | 12/2004 | Washington et al. |
| 2005/0033201 A1 | 2/2005 | Takahashi |
| 2005/0033316 A1 | 2/2005 | Kertz |
| 2005/0038340 A1 | 2/2005 | Vaezy et al. |
| 2005/0055018 A1 | 3/2005 | Kreindel |
| 2005/0055073 A1 | 3/2005 | Weber |
| 2005/0061834 A1 | 3/2005 | Garcia et al. |
| 2005/0070961 A1 | 3/2005 | Maki |
| 2005/0074407 A1 | 4/2005 | Smith |
| 2005/0080469 A1 | 4/2005 | Larson |
| 2005/0085731 A1 | 4/2005 | Miller et al. |
| 2005/0091770 A1 | 5/2005 | Mourad et al. |
| 2005/0096542 A1 | 5/2005 | Weng |
| 2005/0104690 A1 | 5/2005 | Larson et al. |
| 2005/0113689 A1 | 5/2005 | Gritzky |
| 2005/0131302 A1 | 6/2005 | Poland |
| 2005/0137656 A1 | 6/2005 | Malak |
| 2005/0143677 A1 | 6/2005 | Young et al. |
| 2005/0154313 A1 | 7/2005 | Desilets |
| 2005/0154314 A1 | 7/2005 | Quistgaard |
| 2005/0154332 A1 | 7/2005 | Zanelli |
| 2005/0154431 A1 | 7/2005 | Quistgaard |
| 2005/0187495 A1 | 8/2005 | Quistgaard |
| 2005/0191252 A1 | 9/2005 | Mitsui |
| 2005/0193451 A1 | 9/2005 | Quistgaard |
| 2005/0193820 A1 | 9/2005 | Sheljaskow et al. |
| 2005/0197681 A1 | 9/2005 | Barolet et al. |
| 2005/0228281 A1 | 10/2005 | Nefos |
| 2005/0240127 A1 | 10/2005 | Seip et al. |
| 2005/0240170 A1 | 10/2005 | Zhang et al. |
| 2005/0251120 A1 | 11/2005 | Anderson et al. |
| 2005/0251125 A1 | 11/2005 | Pless et al. |
| 2005/0256406 A1 | 11/2005 | Barthe |
| 2005/0261584 A1 | 11/2005 | Eshel |
| 2005/0261585 A1 | 11/2005 | Makin et al. |
| 2005/0267454 A1 | 12/2005 | Hissong |
| 2005/0288748 A1 | 12/2005 | Li et al. |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058671 A1 | 3/2006 | Vitek et al. |
| 2006/0058707 A1 | 3/2006 | Barthe |
| 2006/0058712 A1 | 3/2006 | Altshuler et al. |
| 2006/0074309 A1 | 4/2006 | Bonnefous |
| 2006/0074313 A1 | 4/2006 | Slayton et al. |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin |
| 2006/0084891 A1 | 4/2006 | Barthe |
| 2006/0089632 A1 | 4/2006 | Barthe |
| 2006/0089688 A1 | 4/2006 | Panescu |
| 2006/0094988 A1 | 5/2006 | Tosaya |
| 2006/0111744 A1 | 5/2006 | Makin |
| 2006/0116583 A1 | 6/2006 | Ogasawara et al. |
| 2006/0116671 A1 | 6/2006 | Slayton |
| 2006/0122508 A1 | 6/2006 | Slayton |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0189972 A1 | 8/2006 | Grossman |
| 2006/0206105 A1 | 9/2006 | Chopra |
| 2006/0224090 A1 | 10/2006 | Ostrovsky et al. |
| 2006/0229514 A1 | 10/2006 | Wiener |
| 2006/0241440 A1 | 10/2006 | Eshel |
| 2006/0241442 A1 | 10/2006 | Barthe |
| 2006/0241470 A1 | 10/2006 | Novak et al. |
| 2006/0241576 A1 | 10/2006 | Diederich et al. |
| 2006/0250046 A1 | 11/2006 | Koizumi et al. |
| 2006/0282691 A1 | 12/2006 | Barthe |
| 2006/0291710 A1 | 12/2006 | Wang et al. |
| 2007/0016039 A1 | 1/2007 | Vortman et al. |
| 2007/0032784 A1 | 2/2007 | Gliklich et al. |
| 2007/0035201 A1 | 2/2007 | Desilets |
| 2007/0055154 A1 | 3/2007 | Torbati |
| 2007/0055155 A1 | 3/2007 | Owen et al. |
| 2007/0055156 A1 | 3/2007 | Desilets et al. |
| 2007/0065420 A1 | 3/2007 | Johnson |
| 2007/0083120 A1 | 4/2007 | Cain et al. |
| 2007/0087060 A1 | 4/2007 | Dietrich |
| 2007/0088245 A1 | 4/2007 | Babaev et al. |
| 2007/0088346 A1 | 4/2007 | Mirizzi et al. |
| 2007/0161902 A1 | 7/2007 | Dan |
| 2007/0166357 A1 | 7/2007 | Shaffer et al. |
| 2007/0167709 A1 | 7/2007 | Slayton |
| 2007/0208253 A1 | 9/2007 | Slayton |
| 2007/0219604 A1 | 9/2007 | Yaroslavsky et al. |
| 2007/0219605 A1 | 9/2007 | Yaroslavsky et al. |
| 2007/0238994 A1 | 10/2007 | Stecco et al. |
| 2007/0239075 A1 | 10/2007 | Rosenberg |
| 2007/0239077 A1 | 10/2007 | Azhari et al. |
| 2007/0239079 A1 | 10/2007 | Manstein et al. |
| 2007/0239142 A1 | 10/2007 | Altshuler |
| 2008/0015435 A1 | 1/2008 | Cribbs et al. |
| 2008/0027328 A1 | 1/2008 | Klopotek |
| 2008/0039724 A1 | 2/2008 | Seip et al. |
| 2008/0071255 A1 | 3/2008 | Barthe |

(56) References Cited

U.S. PATENT DOCUMENTS

| | | |
|---|---|---|
| 2008/0086054 A1 | 4/2008 | Slayton |
| 2008/0086056 A1 | 4/2008 | Chang et al. |
| 2008/0097214 A1 | 4/2008 | Meyers et al. |
| 2008/0097253 A1 | 4/2008 | Pedersen et al. |
| 2008/0114251 A1 | 5/2008 | Weymer et al. |
| 2008/0139974 A1 | 6/2008 | Da Silva |
| 2008/0146970 A1 | 6/2008 | Litman et al. |
| 2008/0167556 A1 | 7/2008 | Thompson |
| 2008/0183077 A1 | 7/2008 | Moreau-Gobard et al. |
| 2008/0183110 A1 | 7/2008 | Davenport et al. |
| 2008/0188745 A1 | 8/2008 | Chen et al. |
| 2008/0194964 A1 | 8/2008 | Randall et al. |
| 2008/0195000 A1 | 8/2008 | Spooner et al. |
| 2008/0200810 A1 | 8/2008 | Buchalter |
| 2008/0200813 A1 | 8/2008 | Quistgaard |
| 2008/0214966 A1 | 9/2008 | Slayton |
| 2008/0214988 A1 | 9/2008 | Altshuler et al. |
| 2008/0221491 A1 | 9/2008 | Slayton |
| 2008/0223379 A1 | 9/2008 | Stuker et al. |
| 2008/0242991 A1 | 10/2008 | Moon et al. |
| 2008/0243035 A1 | 10/2008 | Crunkilton |
| 2008/0269608 A1 | 10/2008 | Anderson et al. |
| 2008/0275342 A1 | 11/2008 | Barthe |
| 2008/0281206 A1 | 11/2008 | Bartlett et al. |
| 2008/0281236 A1 | 11/2008 | Eshel et al. |
| 2008/0281237 A1 | 11/2008 | Slayton |
| 2008/0281255 A1 | 11/2008 | Slayton |
| 2008/0294073 A1 | 11/2008 | Barthe |
| 2008/0319356 A1 | 12/2008 | Cain |
| 2009/0005680 A1 | 1/2009 | Jones et al. |
| 2009/0012394 A1 | 1/2009 | Hobelsberger et al. |
| 2009/0043198 A1 | 2/2009 | Milner et al. |
| 2009/0043293 A1 | 2/2009 | Pankratov et al. |
| 2009/0048514 A1 | 2/2009 | Azhari et al. |
| 2009/0069677 A1 | 3/2009 | Chen et al. |
| 2009/0093737 A1 | 4/2009 | Chomas et al. |
| 2009/0156969 A1 | 6/2009 | Santangelo |
| 2009/0163807 A1 | 6/2009 | Sliwa |
| 2009/0171252 A1 | 7/2009 | Bockenstedt et al. |
| 2009/0177122 A1 | 7/2009 | Peterson |
| 2009/0177123 A1 | 7/2009 | Peterson |
| 2009/0182231 A1 | 7/2009 | Barthe et al. |
| 2009/0198157 A1 | 8/2009 | Babaev et al. |
| 2009/0216159 A1 | 8/2009 | Slayton et al. |
| 2009/0226424 A1 | 9/2009 | Hsu |
| 2009/0227910 A1 | 9/2009 | Pedersen et al. |
| 2009/0230823 A1 | 9/2009 | Kushculey et al. |
| 2009/0253988 A1 | 10/2009 | Slayton et al. |
| 2009/0281463 A1 | 11/2009 | Chapelon et al. |
| 2009/0312693 A1 | 12/2009 | Thapliyal et al. |
| 2009/0318909 A1 | 12/2009 | Debenedictis et al. |
| 2009/0326420 A1 | 12/2009 | Moonen et al. |
| 2010/0011236 A1 | 1/2010 | Barthe et al. |
| 2010/0022919 A1 | 1/2010 | Peterson |
| 2010/0022921 A1 | 1/2010 | Seip et al. |
| 2010/0022922 A1 | 1/2010 | Barthe et al. |
| 2010/0030076 A1 | 2/2010 | Vortman et al. |
| 2010/0042020 A1 | 2/2010 | Ben-Ezra |
| 2010/0049178 A1 | 2/2010 | Deem et al. |
| 2010/0056925 A1 | 3/2010 | Zhang et al. |
| 2010/0100014 A1 | 4/2010 | Eshel et al. |
| 2010/0113983 A1 | 5/2010 | Heckerman et al. |
| 2010/0130891 A1 | 5/2010 | Taggart et al. |
| 2010/0160782 A1 | 6/2010 | Slayton et al. |
| 2010/0160837 A1 | 6/2010 | Hunziker et al. |
| 2010/0168576 A1 | 7/2010 | Poland et al. |
| 2010/0191120 A1 | 7/2010 | Kraus et al. |
| 2010/0241035 A1 | 9/2010 | Barthe et al. |
| 2010/0249602 A1 | 9/2010 | Buckley et al. |
| 2010/0249669 A1 | 9/2010 | Ulric et al. |
| 2010/0256489 A1 | 10/2010 | Pedersen et al. |
| 2010/0274161 A1 | 10/2010 | Azhari et al. |
| 2010/0280420 A1 | 11/2010 | Barthe et al. |
| 2010/0286518 A1 | 11/2010 | Lee et al. |
| 2010/0312150 A1 | 12/2010 | Douglas et al. |
| 2011/0040171 A1 | 2/2011 | Foley et al. |
| 2011/0040190 A1 | 2/2011 | Jahnke et al. |
| 2011/0040213 A1 | 2/2011 | Dietz et al. |
| 2011/0040214 A1 | 2/2011 | Foley et al. |
| 2011/0066084 A1 | 3/2011 | Desilets et al. |
| 2011/0087099 A1 | 4/2011 | Eshel et al. |
| 2011/0087255 A1 | 4/2011 | McCormack et al. |
| 2011/0112405 A1 | 5/2011 | Barthe et al. |
| 2011/0144490 A1 | 6/2011 | Davis et al. |
| 2011/0178444 A1 | 7/2011 | Slayton et al. |
| 2011/0178541 A1 | 7/2011 | Azhari |
| 2011/0190745 A1 | 8/2011 | Uebelhoer et al. |
| 2011/0201976 A1 | 8/2011 | Sanghvi et al. |
| 2011/0251524 A1 | 10/2011 | Azhari et al. |
| 2011/0251527 A1 | 10/2011 | Kushculey et al. |
| 2011/0270137 A1 | 11/2011 | Goren et al. |
| 2011/0319793 A1 | 12/2011 | Henrik et al. |
| 2011/0319794 A1 | 12/2011 | Gertner |
| 2012/0004549 A1 | 1/2012 | Barthe et al. |
| 2012/0016239 A1 | 1/2012 | Barthe et al. |
| 2012/0029353 A1 | 2/2012 | Slayton et al. |
| 2012/0035473 A1 | 2/2012 | Sanghvi et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0059288 A1 | 3/2012 | Barthe et al. |
| 2012/0111339 A1 | 5/2012 | Barthe et al. |
| 2012/0123304 A1 | 5/2012 | Rybyanets et al. |
| 2012/0136280 A1 | 5/2012 | Rosenberg et al. |
| 2012/0136282 A1 | 5/2012 | Rosenberg et al. |
| 2012/0143056 A1 | 6/2012 | Slayton et al. |
| 2012/0143100 A1 | 6/2012 | Jeong et al. |
| 2012/0165668 A1 | 6/2012 | Slayton et al. |
| 2012/0165848 A1 | 6/2012 | Slayton et al. |
| 2012/0191019 A1 | 7/2012 | Desilets et al. |
| 2012/0191020 A1 | 7/2012 | Vitek et al. |
| 2012/0197120 A1 | 8/2012 | Makin et al. |
| 2012/0197121 A1 | 8/2012 | Slayton et al. |
| 2012/0209150 A1 | 8/2012 | Zeng et al. |
| 2012/0215105 A1 | 8/2012 | Slayton et al. |
| 2012/0271202 A1 | 10/2012 | Wisdom |
| 2012/0271294 A1 | 10/2012 | Barthe et al. |
| 2012/0296240 A1 | 11/2012 | Azhari et al. |
| 2012/0302883 A1 | 11/2012 | Kong et al. |
| 2012/0316426 A1 | 12/2012 | Foley et al. |
| 2012/0330197 A1 | 12/2012 | Makin et al. |
| 2012/0330222 A1 | 12/2012 | Makin et al. |
| 2012/0330223 A1 | 12/2012 | Makin et al. |
| 2012/0330283 A1 | 12/2012 | Hyde et al. |
| 2012/0330284 A1 | 12/2012 | Hyde et al. |
| 2013/0012755 A1 | 1/2013 | Slayton |
| 2013/0012816 A1 | 1/2013 | Slayton et al. |
| 2013/0012838 A1 | 1/2013 | Jaeger et al. |
| 2013/0012842 A1 | 1/2013 | Barthe |
| 2013/0018285 A1 | 1/2013 | Park et al. |
| 2013/0018286 A1 | 1/2013 | Slayton et al. |
| 2013/0046209 A1 | 2/2013 | Slayton et al. |
| 2013/0051178 A1 | 2/2013 | Rybyanets |
| 2013/0060170 A1 | 3/2013 | Lee et al. |
| 2013/0066208 A1 | 3/2013 | Barthe et al. |
| 2013/0066237 A1 | 3/2013 | Smotrich et al. |
| 2013/0072826 A1 | 3/2013 | Slayton et al. |
| 2013/0096471 A1 | 4/2013 | Slayton et al. |
| 2013/0190659 A1 | 7/2013 | Slayton et al. |
| 2013/0211293 A1 | 8/2013 | Auboiroux et al. |
| 2013/0225994 A1 | 8/2013 | Hsu et al. |
| 2013/0268032 A1 | 10/2013 | Neev |
| 2013/0274603 A1 | 10/2013 | Barthe et al. |
| 2013/0281853 A1 | 10/2013 | Slayton et al. |
| 2013/0281891 A1 | 10/2013 | Slayton et al. |
| 2013/0296697 A1 | 11/2013 | Slayton et al. |
| 2013/0296700 A1 | 11/2013 | Slayton et al. |
| 2013/0296743 A1 | 11/2013 | Lee et al. |
| 2013/0303904 A1 | 11/2013 | Barthe et al. |
| 2013/0303905 A1 | 11/2013 | Barthe et al. |
| 2013/0310714 A1 | 11/2013 | Eshel et al. |
| 2013/0310863 A1 | 11/2013 | Makin et al. |
| 2013/0345562 A1 | 12/2013 | Barthe et al. |

(56) References Cited

U.S. PATENT DOCUMENTS

| | | | |
|---|---|---|---|
| 2014/0024974 A1 | 1/2014 | Slayton et al. |
| 2014/0050054 A1 | 2/2014 | Toda et al. |
| 2014/0081300 A1 | 3/2014 | Melodelima et al. |
| 2014/0082907 A1 | 3/2014 | Barthe et al. |
| 2014/0117814 A1 | 5/2014 | Toda et al. |
| 2014/0142430 A1 | 5/2014 | Slayton et al. |
| 2014/0148834 A1 | 5/2014 | Barthe et al. |
| 2014/0180174 A1 | 6/2014 | Slayton et al. |
| 2014/0187944 A1 | 7/2014 | Slayton et al. |
| 2014/0188015 A1 | 7/2014 | Slayton et al. |
| 2014/0188145 A1 | 7/2014 | Slayton et al. |
| 2014/0194723 A1 | 7/2014 | Herzog et al. |
| 2014/0208856 A1 | 7/2014 | Schmid |
| 2014/0221823 A1 | 8/2014 | Keogh et al. |
| 2014/0236049 A1 | 8/2014 | Barthe et al. |
| 2014/0236061 A1 | 8/2014 | Lee et al. |
| 2014/0243713 A1 | 8/2014 | Slayton et al. |
| 2014/0257145 A1 | 9/2014 | Emery |
| 2014/0276055 A1 | 9/2014 | Barthe et al. |
| 2015/0000674 A1 | 1/2015 | Barthe et al. |
| 2015/0080723 A1 | 3/2015 | Barthe et al. |
| 2015/0080771 A1 | 3/2015 | Barthe et al. |
| 2015/0080874 A1 | 3/2015 | Slayton et al. |
| 2015/0088182 A1 | 3/2015 | Slayton et al. |
| 2015/0164734 A1 | 6/2015 | Slayton et al. |
| 2015/0165238 A1 | 6/2015 | Slayton et al. |
| 2015/0165243 A1 | 6/2015 | Slayton et al. |
| 2015/0174388 A1 | 6/2015 | Slayton |
| 2015/0202468 A1 | 7/2015 | Slayton et al. |
| 2015/0217141 A1 | 8/2015 | Barthe et al. |
| 2015/0360058 A1 | 12/2015 | Barthe et al. |
| 2015/0374333 A1 | 12/2015 | Barthe et al. |
| 2015/0375014 A1 | 12/2015 | Slayton et al. |
| 2016/0027994 A1 | 1/2016 | Toda et al. |
| 2016/0151618 A1 | 6/2016 | Powers et al. |
| 2016/0175619 A1 | 6/2016 | Lee et al. |
| 2016/0206335 A1 | 7/2016 | Slayton |
| 2016/0206341 A1 | 7/2016 | Slayton |
| 2016/0256675 A1 | 9/2016 | Slayton |
| 2016/0296769 A1 | 10/2016 | Barthe et al. |
| 2016/0361572 A1 | 12/2016 | Slayton |
| 2017/0028227 A1 | 2/2017 | Emery et al. |

FOREIGN PATENT DOCUMENTS

| | | |
|---|---|---|
| DE | 10140064 | 3/2003 |
| DE | 10219297 | 11/2003 |
| DE | 10219217 | 12/2004 |
| DE | 20314479 | 12/2004 |
| EP | 0142215 | 5/1984 |
| EP | 0344773 | 12/1989 |
| EP | 1479412 | 11/1991 |
| EP | 0473553 | 4/1992 |
| EP | 670147 | 2/1995 |
| EP | 0661029 | 7/1995 |
| EP | 724894 | 2/1996 |
| EP | 763371 | 11/1996 |
| EP | 1044038 | 10/2000 |
| EP | 1050322 | 11/2000 |
| EP | 1234566 | 8/2002 |
| EP | 1262160 | 12/2002 |
| EP | 0659387 | 4/2003 |
| EP | 1374944 | 1/2004 |
| EP | 1028660 | 1/2008 |
| EP | 1874241 | 1/2008 |
| EP | 1362223 | 5/2008 |
| EP | 1750804 | 7/2008 |
| EP | 1283690 | 11/2008 |
| EP | 1811901 | 4/2009 |
| EP | 1785164 | 8/2009 |
| EP | 2230904 | 9/2010 |
| EP | 1501331 | 6/2011 |
| EP | 2066405 | 11/2011 |
| EP | 2474050 | 7/2012 |
| FR | 2532851 | 9/1983 |
| FR | 2685872 | 1/1992 |
| FR | 2672486 | 8/1992 |
| FR | 2703254 | 3/1994 |
| GB | 2113099 | 8/1983 |
| IL | 102516 | 1/1996 |
| IL | 112369 | 8/1999 |
| IL | 120079 | 3/2001 |
| JP | 63036171 | 2/1988 |
| JP | 03048299 | 3/1991 |
| JP | 3123559 | 5/1991 |
| JP | 03136642 | 6/1991 |
| JP | 4089058 | 3/1992 |
| JP | 04150847 | 5/1992 |
| JP | 7080087 | 3/1995 |
| JP | 07505793 | 6/1995 |
| JP | 7184907 | 7/1995 |
| JP | 7222782 | 8/1995 |
| JP | 09047458 | 2/1997 |
| JP | 9108288 | 4/1997 |
| JP | 9503926 | 4/1997 |
| JP | 11123226 | 5/1999 |
| JP | 11505440 | 5/1999 |
| JP | 11506636 | 6/1999 |
| JP | 10248850 | 9/1999 |
| JP | 2000126310 | 5/2000 |
| JP | 2000166940 | 6/2000 |
| JP | 2000233009 | 8/2000 |
| JP | 2001170068 | 6/2001 |
| JP | 2002505596 | 2/2002 |
| JP | 2002078764 | 3/2002 |
| JP | 2002515786 | 5/2002 |
| JP | 2002521118 | 7/2002 |
| JP | 2002537939 | 11/2002 |
| JP | 2003050298 | 7/2003 |
| JP | 2003204982 | 7/2003 |
| JP | 2004-504898 | 2/2004 |
| JP | 2004-507280 | 3/2004 |
| JP | 2004-509671 | 4/2004 |
| JP | 2004-512856 | 4/2004 |
| JP | 2004147719 | 5/2004 |
| JP | 2005503388 | 2/2005 |
| JP | 2005527336 | 9/2005 |
| JP | 2005323213 | 11/2005 |
| JP | 2006520247 | 9/2006 |
| JP | 2008515559 | 5/2008 |
| JP | 2009518126 | 5/2009 |
| JP | 2010517695 | 5/2010 |
| KR | 1020010024871 | 3/2001 |
| KR | 100400870 | 10/2003 |
| KR | 20060121267 | 11/2006 |
| KR | 1020060113930 | 11/2006 |
| KR | 1020070065332 | 6/2007 |
| KR | 1020070070161 | 7/2007 |
| KR | 1020070098856 | 10/2007 |
| KR | 1020070104878 | 10/2007 |
| KR | 1020070114105 | 11/2007 |
| KR | 1020000059516 | 4/2012 |
| KR | 10-2013-0124598 | 11/2013 |
| KR | 10-1365946 | 2/2014 |
| TW | 386883 | 9/2000 |
| TW | 201208734 A | 3/2012 |
| WO | WO9312742 | 7/1993 |
| WO | WO9524159 | 9/1995 |
| WO | WO9625888 | 8/1996 |
| WO | WO9634568 | 11/1996 |
| WO | WO9639079 | 12/1996 |
| WO | WO9735518 | 10/1997 |
| WO | WO9832379 | 7/1998 |
| WO | WO9852465 | 11/1998 |
| WO | WO9933520 | 7/1999 |
| WO | WO9949788 | 10/1999 |
| WO | WO200006032 | 2/2000 |
| WO | WO0015300 | 3/2000 |
| WO | WO0021612 | 4/2000 |
| WO | WO0053113 | 9/2000 |
| WO | WO0128623 | 4/2001 |
| WO | WO01045550 | 6/2001 |
| WO | WO0182777 | 11/2001 |
| WO | WO0182778 | 11/2001 |

(56) References Cited

FOREIGN PATENT DOCUMENTS

| | | |
|---|---|---|
| WO | WO0187161 | 11/2001 |
| WO | WO01080709 | 11/2001 |
| WO | WO2001087161 | 11/2001 |
| WO | WO 02/09812 | 2/2002 |
| WO | WO0209813 | 2/2002 |
| WO | WO02015768 | 2/2002 |
| WO | WO0224050 | 3/2002 |
| WO | WO2002054018 | 7/2002 |
| WO | WO02092168 | 11/2002 |
| WO | WO03053266 | 7/2003 |
| WO | WO03065347 | 8/2003 |
| WO | WO03070105 | 8/2003 |
| WO | WO03077833 | 9/2003 |
| WO | WO03086215 | 10/2003 |
| WO | WO03096883 | 11/2003 |
| WO | WO03099177 | 12/2003 |
| WO | WO03099382 | 12/2003 |
| WO | WO03101530 | 12/2003 |
| WO | WO2004000116 | 12/2003 |
| WO | WO2004080147 | 9/2004 |
| WO | WO2004110558 | 12/2004 |
| WO | WO2005/011804 | 2/2005 |
| WO | WO2005065408 | 7/2005 |
| WO | WO2005065409 | 7/2005 |
| WO | WO2005090978 | 9/2005 |
| WO | WO2005113068 | 12/2005 |
| WO | WO2006/042163 | 4/2006 |
| WO | WO2006036870 | 4/2006 |
| WO | WO2006042168 | 4/2006 |
| WO | WO2006042201 | 4/2006 |
| WO | WO2006065671 | 6/2006 |
| WO | WO2006082573 | 8/2006 |
| WO | WO2006104568 | 10/2006 |
| WO | WO2007067563 | 6/2007 |
| WO | WO2008036479 | 3/2008 |
| WO | WO2008036622 | 3/2008 |
| WO | WO2008144274 | 11/2008 |
| WO | WO2009013729 | 1/2009 |
| WO | WO2009149390 | 10/2009 |
| WO | WO2012134645 | 10/2012 |
| WO | WO2013048912 | 4/2013 |
| WO | WO2014045216 | 3/2014 |
| WO | WO2014055708 | 4/2014 |
| WO | WO2014057388 | 4/2014 |
| WO | WO2014127091 | 8/2014 |
| WO | WO2015160708 | 10/2015 |
| WO | WO2018035012 | 2/2018 |

OTHER PUBLICATIONS

Dermafocus Exhibit 2027, DermaFocus Oral Proceeding Demonstrative Slides (filed Oct. 2, 2017 in re IPR2016-01459).

PTAB Record of Oral Hearing held Oct. 4, 2017 in Re U.S. Pat. No. 6,113,559; IPR2016-01459; 67 pages (PTAB Document sent to Ulthera on Nov. 1, 2017).

A Validated Photonumeric Cellulite Severity Scale; Hexsel et al; J Eur Acad Dermatol Venereol. May 2009;23(5):523-8, 6 pages.

Agren, Magnus S. et al., Collagenase in Wound Healing: Effect of Wound Age and Type. The Journal of Investigative Dermatology, vol. 99/No. 6, (Dec. 1992).

Alam, M., "The future of noninvasive procedural dermatology". Semin Cutan Med Surg. Mar. 2013; 32(1):59-61.

Alam, M., et al., "Ultrasound tightening of facial and neck skin: a rater-blinded prospective cohort study". J Am Acad Dermatol, 2010. 62(2): p. 262-9.

Alexiades-Armenakas, M., "Ultrasound Technologies for Dermatologic Techniques". J Drugs Derm. 2014. 12 (11): p. 1305.

Alster, T.S., et. al., "Noninvasive lifting of arm, thigh, and knee skin with transcutaneousintense focused ultrasound". Dermatol Surg, 2012. 38(5): p. 754-9.

Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.

Arosarena, O., "Options and Challenges for Facial Rejuvenation in Patients With Higher Fitzpatrick Skin Phototypes". JAMA Facial Plastic Surgery, 2015.

Arthur et al., "Non-invasive estimation of hyperthermia temperatures with ultrasound," Int. J. Hyperthermia, Sep. 2005, 21(6), pp. 589-600.

Barthe et al., "Ultrasound therapy system and ablation results utilizing miniature imaging/therapy arrays," Ultrasonics Symposium, 2004 IEEE, Aug. 23, 2004, pp. 1792-1795, vol. 3.

Bozec, Laurent et al., Thermal Denaturation Studies of Collagen by Microthermal Analysis and Atomic Force Microscopy, Biophysical Journal, vol. 101, pp. 228-236. (Jul. 2001).

Brobst, R.W., et. al., "Noninvasive Treatment of the Neck". Facial Plast Surg Clin North Am, 2014. 22(2): p. 191-202.

Brobst, R.W., et., al., "Ulthera: initial and six month results". Facial Plast Surg Clin North Am, 2012. 20(2): p. 163-76.

Calderhead et al., "One Mechanism Behind LED Photo-Therapy for Wound Healing and Skin Rejuvenation: Key Role of the Mast Cell" Laser Therapy 17.3: 141-148 (2008).

Casabona, G., et. al., "Microfocused Ultrasound With Visualization and Fillers for Increased Neocollagenesis: Clinical and Histological Evaluation". Dermatol Surg 2014;40:S194-S198.

Chan, N.P., et al., "Safety study of transcutaneous focused ultrasound for non-invasive skin tightening in Asians". Lasers Surg Med, 2011. 43(5): p. 366-75.

Chapelon et al., "Effects of Cavitation in the High Intensity Therapeutic Ultrasound", Ultrasonics Symposium—1357 (1991).

Chapelon, et al., "Thresholds for Tissue Ablation by Focused Ultrasound" (1990).

Chen, L. et al., "Effect of Blood Perfusion on the ablation of liver parenchyma with high intensity focused ultrasound," Phys. Med. Biol; 38:1661-1673; 1993b.

Coon, Joshua et al., "Protein identification using sequential ion/ion reactions and tandem mass spectrometry" Proceedings of the National Academy of Sciences of the USA, vol. 102, No. 27, Jul. 27, 2005, pp. 9463-9468.

Corry, Peter M., et al., "Human Cancer Treatment with Ultrasound", IEEE Transactions on Sonics and Ultrasonics, vol. SU-31, No. 5, Sep. 1984, pp. 444, 456.

Damianou et al., "Application of the Thermal Dose Concept for Predicting the Necrosed Tissue Volume During Ultrasound Surgery," 1993 IEEE Ultrasound Symposium, pp. 1199-1202.

Daum et al., Design and Evaluation of a Feedback Based Phased Array System for Ultrasound Surgery, IEEE Transactions on Ultrasonics, Ferroelectrics, and Frequency Control, vol. 45, No. 2, Mar. 1998, pp. 431-438.

Davis, Brian J., et al., "An Acoustic Phase Shift Technique for the Non-Invasive Measurement of Temperature Changes in Tissues", 1985 Ultrasonics Symposium, pp. 921-924.

Dayan, S.H., et al., "Prospective, Multi-Center, Pivotal Trial Evaluating the Safety and Effectiveness of Micro-Focused Ultrasound with Visualization (MFU-V) for Improvement in Lines and Wrinkles of the Décolletage". Plast Reconstr Surg. Oct. 2014; 134(4 Suppl 1):123-4.

Decision of the Korean Intellectual Property Tribunal dated Jun. 28, 2013 regarding Korean Patent No. 10-1142108, which is related to the pending application and/or an application identified in the Table on pp. 1-4 of the Information Disclosure Statement herein (English translation, English translation certification, and Korean decision included).

Delon Martin, C., et al, "Venous Thrombosis Generation by Means of High-Intensity Focused Ultrasound" Ultrasound in Med. & Biol., vol. 21, No. 1, pp. 113-119 (1995).

Dierickx, Christine C., "The Role of Deep Heating for Noninvasive Skin Rejuvenation" Lasers in Surgery and Medicine 38:799-807 (2006).

Dobke, M.K., et al., "Tissue restructuring by energy-based surgical tools". Clin Plast Surg, 2012. 39(4): p. 399-408.

Dong, Yuan-Lin et al., "Effect of Ibuprofen on the Inflammatory Response to Surgical Wounds" The Journal of Trauma, vol. 35, No. 3. (1993).

(56) References Cited

OTHER PUBLICATIONS

Dvivedi, Sanjay, et al. "Effect of Ibuprofen and diclofenac sodium on experimental wound healing" Indian Journal of Experimental Biology, vol. 35, pp. 1243-1245. (Nov. 1997).
Fabi, S.G., "Microfocused Ultrasound With Visualization for Skin Tightening and Lifting: My Experience and a Review of the Literature". Dermatol Surg. Dec. 2014; 40 Suppl 12:S164-7.
Fabi, S.G., "Noninvasive skin tightening: focus on new ultrasound techniques". Clin Cosmet Investig Dermatol. Feb. 5, 2015; 8:47-52.
Fabi, S.G., et. al., "A prospective multicenter pilot study of the safety and efficacy of microfocused ultrasound with visualization for improving lines and wrinkles of the décolleté". Dermatol Surg. Mar. 2015; 41(3):327-35.
Fabi, S.G., et. al., "Evaluation of microfocused ultrasound with visualization for lifting, tightening, and wrinkle reduction of the decolletage". J Am Acad Dermatol, 2013. 69(6): p. 965-71.
Fabi, S.G., et. al., "Future directions in cutaneous laser surgery". Dermatol Clin, 2014. 32(1): p. 61-9.
Fabi, S.G., et. al., "Retrospective Evaluation of Micro-focused Ultrasound for Lifting and Tightening the Face and Neck". Dermatol Surg, 2014.
Friedmann D.P., "Comments on evaluation of microfocused ultrasound system for improving skin laxity and tightening in the lower face". Aesthet Surg J. Mar. 2015;35(3):NP81-2.
Friedmann, D.P., et. al., "Combination of intense pulsed light, Sculptra, and Ultherapy for treatment of the aging face". J Cosmet Dermatol, 2014. 13(2): p. 109-18.
Fry, W.J. et al., "Production of Focal Destructive Lesions in the Central Nervous System with Ultrasound," J. Neurosurg., 11:471-478; 1954.
Fujimoto, et al., "A New Cavitation Suppression Technique for Local Ablation Using High-Intensity Focused Ultrasound" Ultrasonics Symposium—1629 (1995).
Gliklich et al., Clinical Pilot Study of Intense Ultrasound therapy to Deep Dermal Facial Skin and Subcutaneous Tissues, Arch Facial Plastic Surgery, Mar. 1, 2007, vol. 9, No. 1.
Gold, M.H., et. al., "Use of Micro-Focused Ultrasound with Visualization to Lift and Tighten Lax Knee Skin". J Cosmet Laser Ther, 2014: p. 1-15.
Goldberg, D.J., et. al., "Safety and Efficacy of Microfocused Ultrasound to Lift, Tighten, and Smooth the Buttocks". Dermatol Surg 2014; 40:1113-1117.
Greene, R.M., et al., "Skin tightening technologies". Facial Plast Surg. Feb. 2014; 30(1):62-7.
Greenhalgh, David G., "Wound healing and diabetes mellitus" Clinics in Plastic Surgery 30; 37-45. (2003).
Guo, S. et al., "Factors Affecting Wound Healing" Critical Reviews in Oral Biology & Medicine, J Dent Res 89(3), pp. 219-229. (2010).
Haar, G.R. et al., "Tissue Destruction with Focused Ultrasound in Vivo," Eur. Urol. 23 (suppl. 1):8-11; 1993.
Hantash, Basil M. et al., "Bipolar Fractional Radiofrequency Treatment Induces Neoelastogenesis and Neocollagenesis" Lasers in Surgery and Medicine 41:1-9 (2009).
Hantash, Basil M. et al., "In Vivo Histological Evaluation of a Novel Ablative Fractional Resurfacing Device" Lasers in Surgery and Medicine 39:96-107 (2007).
Harris, M.O., "Safety of Microfocused Ultrasound With Visualization in Patients With Fitzpatrick Skin Phototypes III to VI". JAMA Facial Plast. Surg, 2015.
Hart, et. al., "Current Concepts in the Use of PLLA:Clinical Synergy Noted with Combined Use of Microfocused Ultrasound and Poly-l-Lactic Acid on the Face, Neck, and Décolletage". Amer. Soc. Plast. Surg. 2015. 136; 180-187S.
Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.
Hassan et al., "Structure and Morphology of Freeze/Thawed PVA Hydrogels," Macromolecules, Mar. 11, 2000, pp. 2472-2479, vol. 33, No. 7.
Hitchcock, T.M. et. al., "Review of the safety profile for microfocused ultrasound with Visualization". Journal of Cosmetic Dermatology, 13, 329-335. (2014).
Husseini et al, "The Role of Cavitation in Acoustically Activated Drug Delivery," J. Control Release, Oct. 3, 2005, pp. 253-261, vol. 107(2).
Husseini et al. "Investigating the mechanism of acoustically activated uptake of drugs from Pluronic micelles," BMD Cancer 2002, 2:20k, Aug. 30, 2002, pp. 1-6.
Hynynen et al., Temperature Distributions During Local Ultrasound Induced Hyperthermia In Vivo, Ultrasonics Symposium—745 (1982).
Jeffers et al., "Evaluation of the Effect of Cavitation Activity on Drug-Ultrasound Synergisms," 1993 IEEE Ultrasonics Symposium, pp. 925-928.
Jenne, J., et al., "Temperature Mapping for High Energy US-Therapy", 1994 Ultrasonics Symposium, pp. 1879-1882.
Jeong, K.H., et al., "Neurologic complication associated with intense focused ultrasound". J Cosmet Laser Ther, 2013.
Johnson, S.A., et al., "Non-Intrusive Measurement of Microwave and Ultrasound-Induced Hyperthermia by Acoustic Temperature Tomography", Ultrasonics Symposium Proceedings, pp. 977-982. (1977).
Kim, H.J. et al., "Coagulation and ablation patterns of high-intensity focused ultrasound on a tissue mimicking phantom and cadaveric skin". Laser Med Sci. Sep. 4, 2015.
Kornstein, A.N., "Ulthera for silicone lip correction". Plast Reconstr Surg, 2012. 129(6): p. 1014e-1015e.
Kornstein, A.N., "Ultherapy shrinks nasal skin after rhinoplasty following failure of conservative measures". Plast Reconstr Surg, 2013. 131(4): p. 664e-6e.
Krischak, G.D., et al., "The effects of non-steroidal anti-inflammatory drug application on incisional wound healing in rats" Journal of Wound Care, vol. 6, No. 2, (Feb. 2007).
Laubach, H.J., et. al., "Confined Thermal Damage with Intense Ultrasound (IUS)" [abstr.] American Society for Laser Medicine and Surgery Abstracts, p. 15 #43 (Apr. 2006).
Laubach, H.J., et. al., "Intense focused ultrasound: evaluation of a new treatment modality for precise microcoagulation within the skin". Dermatol Surg, 2008. 34(5): p. 727-34.
Lee, H.J. et. al., "The efficacy and safety of intense focused ultrasound in the treatment of enlarged facial pores in Asian skin". J Dermatolog Treat, 2014.
Lee, H.S., et. al., "Multiple Pass Ultrasound Tightening of Skin Laxity of the Lower Face and Neck". Dermatol Surg, 2011.
Lin, Sung-Jan, et al., "Monitoring the thermally induced structural transitions of collagen by use of second-harmonic generation microscopy" Optics Letters, vol. 30, No. 6, (Mar. 15, 2005).
Macgregor J.L., et. al., "Microfocused Ultrasound for Skin Tightening". Semin Cutan Med Surg 32:18-25. (2013).
Madersbacher, S. et al., "Tissue Ablation in Benign Prostatic Hyperplasia with High Intensity Focused Ultrasound," Dur. Urol., 23 (suppl. 1):39-43; 1993.
Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.
Makin et al, "Confirmed Bulk Ablation and Therapy Monitoring Using Intracorporeal Image-Treat Ultrasound Arrays," 4th International Symposium on Therapeutic Ultrasound, Sep. 19, 2004.
Makin et al., "Miniaturized Ultrasound Arrays for Interstitial Ablation and Imaging," UltraSound Med. Biol. 2005, Nov. 1, 2005, pp. 1539-1550, vol. 31(11).
Manohar et al, "Photoacoustic mammography laboratory prototype: imaging of breast tissue phantoms," Journal of Biomedical Optics, Nov./Dec. 2004, pp. 1172-1181, vol. 9, No. 6.
Mast et al, "Bulk Ablation of Soft Tissue with Intense Ultrasound; Modeling and Experiments," J. Acoust. Soc. Am., Oct. 1, 2005, pp. 2715-2724, vol. 118(4).
Meshkinpour, Azin, et al., "Treatment of Hypertrophic Scars and Keloids With a Radiofrequency Device: A Study of Collagen Effects" Lasers in Surgery and Medicine 37:343-349 (2005).

(56) References Cited

OTHER PUBLICATIONS

Microfocused Ultrasound with Visualization and Calcium Hydroxylapatite for Improving Skin Laxity and Cellulite Appearance; Casabona et al.; Plast Reconstr Surg Glob Open. Jul. 25, 2017;5(7):e1388, 8 pages.

Microfocused Ultrasound With Visualization and Fillers for Increased Neocollagenesis: Clinical and Histological Evaluation;I Casabona et al.; Dermatol Surg. Dec. 2014; 40 Suppl 12:S194-8, 5 pages.

Minkis, K., et. al., "Ultrasound skin tightening". Dermatol Clin, 2014. 32(1): p. 71-7.

Mitragotri, S., "Healing sound: the use of ultrasound in drug delivery and other therapeutic applications," Nature Reviews; Drug Delivery, pp. 255-260, vol. 4 (Mar. 2005).

Mosser, David M. et al., "Exploring the full spectrum of macrophage activation" Nat Rev Immunol; 8(12): 958-969. (Dec. 2008).

Murota, Sei-Itsu, et al., "Stimulatory Effect of Prostaglandins on the Production of Hexosamine-Containing Substances by Cultured Fibroblasts (3) Induction of Hyaluronic Acid Synthetase by Prostaglandin" Department of Pharmacology, Tokyo Metropolitan Institute of Gerontology, Itabashiku, Tokyo-173, Japan. (Nov. 1977, vol. 14, No. 5).

Murota, Sei-Itsu, et al., "The Stimulatory Effect of Prostaglandins on Production of Hexosamine-Containing Substances by Cultured Fibroblasts" Department of Pharmacology, Tokyo Metropolitan Institute of Gerontology, Itabashiku, Tokyo-173, Japan. (Aug. 1976, vol. 12, No. 2).

Nestor, M.S. et. al., "Safety and Efficacy of Micro-focused Ultrasound Plus Visualization for the Treatment of Axillary Hyperhidrosis". J Clin Aesthet Dermatol, 2014. 7(4): p. 14-21.

Oni, G., et. al. "Response to 'comments on evaluation of microfocused ultrasound system for improving skin laxity and tightening in the lower face'". Aesthet Surg J. Mar. 2015;35(3):NP83-4.

Oni, G., et. al., "Evaluation of a Microfocused Ultrasound System for Improving Skin Laxity and Tightening in the Lower Face". Aesthet Surg J, 2014. 38:861-868.

Pak, C.S. et. al., "Safety and Efficacy of Ulthera in the Rejuvenation of Aging Lower Eyelids: A Pivotal Clinical Trial". Aesthetic Plast Surg, 2014.

Paradossi et al., "Poly(vinyl alcohol) as versatile biomaterial for potential biomedical applications," Journal of Materials Science: Materials in Medicine, 2003, pp. 687-691, vol. 14.

Pritzker, R.N., et. al, "Updates in noninvasive and minimally invasive skin tightening". Semin Cutan Med Surg. Dec. 2014;33(4):182-7.

Pritzker, R.N., et. al., "Comparison of different technologies for noninvasive skin tightening". Journal of Cosmetic Dermatology, 13, 315-323. (2014).

Rappolee, Daniel A., et al., "Wound Macrophages Express Tgf and Other Growth Factors in Vivo: Analysis by mRNA Phenotyping" Science, vol. 241, No. 4866 (Aug. 1988).

Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.

Righetti et al, "Elastographic Characterization of HIFU-Induced Lesions in Canine Livers," 1999, Ultrasound in Med & Bio, vol. 25, No. 7, pp. 1099-1113.

Rokhsar, C., et. al., "Safety and efficacy of microfocused ultrasound in tightening of lax elbow skin". Dermatol Surg. 2015; 41(7):821-6.

Rosenberg, Carol S. "Wound Healing in the Patient with Diabetes Mellitus" Nursing Clinics of North America, vol. 25, No. 1, (Mar. 1990).

Saad et al., "Ultrasound-Enhanced Effects of Adriamycin Against Murine Tumors," Ultrasound in Med. & Biol. vol. 18, No. 8, pp. 715-723 (1992).

Sabet-Peyman, E.J. et. al., "Complications Using Intense Ultrasound Therapy to TreatDeep Dermal Facial Skin and Subcutaneous Tissues". Dermatol Surg 2014; 40:1108-1112.

Sandulache, Vlad C. et al., "Prostaglandin E2 inhibition of keloid fibroblast migration, contraction, and transforming growth factor (TGF)-B1-induced collagen synthesis" Wound Rep Reg 15 122-133, 2007. (2007).

Sanghvi, N.T., et al., "Transrectal Ablation of Prostate Tissue Using Focused Ultrasound," 1993 Ultrasonics Symposium, IEEE, pp. 1207-1210.

Sasaki, G.H. et. al., "Clinical Efficacy and Safety of Focused-Image Ultrasonography: A 2-Year Experience". Aesthet Surg J, 2012.

Sasaki, G.H. et. al., "Microfocused Ultrasound for Nonablative Skin and Subdermal Tightening to the Periorbitum and Body Sites: Preliminary Report on Eighty-Two Patients". Journal of Cosmetics, Dermatological Sciences and Applications, 2012, 2, 108-116.

Sassen, Sander, "ATI's R520 architecture, the new king of the hill?" http://www.hardwareanalysis.com/content/article/1813, Sep. 16, 2005, 2 pages.

Seip, Ralf, et al., "Noninvasive Detection of Thermal Effects Due to Highly Focused Ultrasonic Fields," IEEE Symposium, pp. 1229-1232, vol. 2, Oct. 3-Nov. 1993.

Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.

Simon et al., "Applications of Lipid-Coated Microbubble Ultrasonic Contrast to Tumor Therapy," Ultrasound in Med. & Biol. vol. 19, No. 2, pp. 123-125 (1993).

Sklar, L.R. et. al., "Use of transcutaneous ultrasound for lipolysis and skin tightening: a review". Aesthetic Plast Surg, 2014. 38(2): p. 429-41.

Smith, Nadine Barrie, et al., "Non-invasive In Vivo Temperature Mapping of Ultrasound Heating Using Magnetic Resonance Techniques", 1994 Ultrasonics Symposium, pp. 1829-1832, vol. 3.

Suh, D.H., et. al., "A intense-focused ultrasound tightening for the treatment of infraorbital laxity". J Cosmet Laser Ther, 2012. 14(6): p. 290-5.

Suh, D.H., et. al., "Comparative histometric analysis of the effects of high-intensity focused ultrasound and radiofrequency on skin". J Cosmet Laser Ther. Mar. 2015 24:1-7.

Suh, D.H., et. al., "Intense Focused Ultrasound Tightening in Asian Skin: Clinical and Pathological Results" American Society for Dermatologic Surgery, Inc.; 37:1595-1602. (2011).

Su, D.H., et. al., "Intense focused ultrasound tightening in asian skin: clinical and pathologic results". Dermatol Surg, 2011. 37(11): p. 1595-602.

Surry et al., "Poly(vinyl alcohol) cryogel phantoms for use in ultrasound and MR imaging," Phys. Med. Biol., Dec. 6, 2004, pp. 5529-5546, vol. 49.

Syka J. E. P. et al., "Peptide and Protein Sequence Analysis by Electron Transfer Dissociation Mass Spectrometry," Proceedings of the National Academy of Sciences of USA, National Academy of Science, Washington, DC, vol. 101, No. 26, Jun. 29, 2004, pp. 9528-9533.

Talbert, D. G., "An Add-On Modification for Linear Array Real-Time Ultrasound Scanners to Produce 3D Displays," UTS Int'l 1977 Brighton, England (Jun. 28-30, 1977) pp. 57-67.

Tata et al., "Interaction of Ultrasound and Model Membrane Systems: Analyses and Predictions," American Chemical Society, Phys. Chem. 1992, 96, pp. 3548-3555.

Ueno, S., et al., "Ultrasound Thermometry in Hyperthermia", 1990 Ultrasonic Symposium, pp. 1645-1652.

Verhofstad, Michiel H.J. et al., "Collagen Synthesis in rat skin and ileum fibroblasts is affected differently by diabetes-related factors" Int. J. Exp. Path. (1998), 79, 321-328.

Wang, H., et al., "Limits on Focused Ultrasound for Deep Hyperthermia", 1994 Ultrasonic Symposium, Nov. 1-4, 1994, pp. 1869-1872, vol. 3.

Wasson, Scott, "NVIDIA's GeForce 7800 GTX graphics processor Power MADD," http://techreport.com/reviews/2005q2/geforce-7800gtx/index.x?pg=1, Jun. 22, 2005, 4 pages.

Weiss, M., "Commentary: noninvasive skin tightening: ultrasound and other technologies: where are we in 2011?" Dermatol Surg, 2012. 38(1): p. 28-30.

(56) References Cited

OTHER PUBLICATIONS

White et al "Selective Creating of Thermal Injury Zones in the Superficial Musculoaponeurotic System Using Intense Ultrasound Therapy," Arch Facial Plastic Surgery, Jan./Feb. 2007, vol. 9, No. 1 (pp. 22-29).
White, W. M., et al., "Selective Transcutaneous Delivery of Energy to Facial Subdermal Tissues Using the Ultrasound Therapy System" [abstr]. American Society for Laser Medicine and Surgery Abstracts, p. 37 #113 (Apr. 2006).
White, W. Matthew, et al., "Selective Transcutaneous Delivery of Energy to Porcine Soft Tissues Using Intense Ultrasound (IUS)" Lasers in Surgery and Medicine 40:67-75 (2008).
Woodward, J.A., et. al. "Safety and Efficacy of Combining Microfocused Ultrasound With Fractional $CO_2$ Laser Resurfacing for Lifting and Tightening the Face and Neck". Dermatol Surg, Dec. 2014 40:S190-S193.
Zelickson, Brian D. et al., "Histological and Ultrastructural Evaluation of the Effects of a Radiofrequency-Based Nonablative Dermal Remodeling Device, a Pilot Study" Arch Dermatol, vol. 140, (Feb. 2004).
Ulthera, Inc., Petition for Inter Partes Review filed Jul. 19, 2016 in Re U.S. Pat. No. 6,113,559; IPR2016-01459; 63 pages (Filed Jul. 19, 2016).
Ulthera Exhibit 1001, U.S. Pat. No. 6,113,559 to Klopotek, filed Jul. 19, 2016 in re IPR2016-01459.
Ulthera Exhibit 1002, Patent file history of U.S. Pat. No. 6,113,559 Klopotek filed Jul. 19, 2016 in re IPR2016-01459.
Ulthera Exhibit 1003, Declaration of Expert Witness Mark E. Schafer, Ph.D. filed Jul. 19, 2016 in re IPR2016-01459.
Ulthera Exhibit 1004, Curriculum Vitae of Mark E. Schafer, Ph.D. filed Jul. 19, 2016 in re IPR2016-01459.
Ulthera Exhibit 1005, International PCT Publication WO96/34568 Knowlton filed Jul. 19, 2016 in re IPR2016-01459.
Ulthera Exhibit 1006, French U.S. Pat. No. 2,672,486, Technomed patent filed Jul. 19, 2016 in re IPR2016-01459.
Ulthera Exhibit 1007, English translation of French U.S. Pat. No. 2,672,486, Technomed filed Jul. 19, 2016 in re IPR2016-01459.
Ulthera Exhibit 1008, International PCT Publication WO93/12742, Technomed PCT filed Jul. 19, 2016 in re IPR2016-01459.
Ulthera Exhibit 1009, English translation of International PCT Publication WO93/12742, Technomed PCT filed Jul. 19, 2016 in re IPR2016-01459.
Ulthera Exhibit 1010, U.S. Pat. No. 5,601,526, which claims priority to Technomed PCT filed Jul. 19, 2016 in re IPR2016-01459.
Ulthera Exhibit 1011, Patent file history for European Patent Application No. 98964890.2, Klopotek filed Jul. 19, 2016 in re IPR2016-01459.
Ulthera Exhibit 1012, Translator Declaration filed Jul. 19, 2016 in re IPR2016-01459.
Ulthera Exhibit 1013, U.S. Pat. No. 5,230,334 to Klopotek filed Jul. 19, 2016 in re IPR2016-01459.
Ulthera Exhibit 1014, U.S. Pat. No. 5,755,753 to Knowlton filed Jul. 19, 2016 in re IPR2016-01459.
Ulthera Exhibit 1015, Excerpts from the American Medical Association Encyclopedia of Medicine (1989) filed Jul. 19, 2016 in re IPR2016-01459.
Ulthera Exhibit 1016, The Simultaneous Study of Light Emissions and Shock Waves Produced by Cavitation Bubbles, G. Gimenez, J. Acoust. Soc. Am. 71(4), Apr. 1982, pp. 839-847 (filed Jul. 19, 2016 in re IPR2016-01459).
Ulthera Exhibit 1017, Excerpts from Gray's Anatomy (1995) (filed Jul. 19, 2016 in re IPR2016-01459).
Ulthera Exhibit 1018, Anatomy of the Superficial Venous System, Comjen G.M., Dermatol. Surg., 1995; 21:35-45 (filed Jul. 19, 2016 in re IPR2016-01459).
Ulthera Exhibit 1019, Section 2.6 from Ultrasonics Theory and Application, by G.L. Gooberman (Hart Publishing Co., 1969) (filed Jul. 19, 2016 in re IPR2016-01459).
Ulthera Exhibit 1020, Deep Local Hyperthermia for Cancer Therapy: External Electromagnetic and Ultrasound Techniques, A.Y. Cheung and A. Neyzari, Cancer Research (Suppl.), vol. 44, pp. 4736-4744 (1984) (filed Jul. 19, 2016 in re IPR2016-01459).
Decision on Institution of Inter Partes Review in Re U.S. Pat. No. 6,113,559; IPR2016-01459; 20 pages [011] (Dated Jan. 23, 2017).
Dermafocus Response to Institution of Inter Partes Review in Re U.S. Pat. No. 6,113,559; IPR2016-01459; 73 pages [018] (Dated Apr. 26, 2017).
Dermafocus Exhibit List in Re U.S. Pat. No. 6,113,559; IPR2016-01459; 5 pages [019] (Dated Apr. 26, 2017).
Dermafocus Exhibit 2002, Declaration of Mark Palmeri, in Re U.S. Pat. No. 6,113,559; IPR2016-01459; 136 pages (Filed Apr. 26, 2017).
Dermafocus Exhibit 2003, Deposition of Dr. Mark Schafer, in Re U.S. Pat. No. 6,113,559; IPR2016-01459; 327 pages (Filed Apr. 26, 2017).
Dermafocus Exhibit 2004, Amendment No. 4 to Ulthera Form S-1, in Re U.S. Pat. No. 6,113,559; IPR2016-01459; 308 pages (Filed Apr. 26, 2017).
Dermafocus Exhibit 2005, Excerpt from Churchill Livingstone, Gray's Anatomy (38th ed. 1995), in Re U.S. Pat. No. 6,113,559; IPR2016-01459; 7 pages (Filed Apr. 26, 2017).
Dermafocus Exhibit 2006, Bo Eklof et al., "Revision of the CEAP Classification for Chronic Venous Disorders: Consensus Statement," ACTA FAC MED NAISS, vol. 25, No. 1 (2008), 3-10 in Re U.S. Pat. No. 6,113,559; IPR2016-01459; 7 pages (Filed Apr. 26, 2017).
Dermafocus Exhibit 2007, WebMD, "Varicose Veins and Spider Veins" downloaded from http://www.webmd.com/skin-problems-andtreatments/guide/varicose-spider-veins#1 in Re U.S. Pat. No. 6,113,559; IPR2016-01459; 3 pages (Filed Apr. 26, 2017).
Dermafocus Exhibit 2008, John M. Porter et al, "Reporting Standards in Venous Disease: An Update," Journal of Vascular Surgery, vol. 21, No. 4 (1995), 635-645 in Re U.S. Pat. No. 6,113,559; IPR2016-01459; 11 pages (Filed Apr. 26, 2017).
Dermafocus Exhibit 2009, Kullervo Hynynen, "Review of Ultrasound Therapy," 1997 Ultrasonics Symposium (1997), 1305-1313, in Re U.S. Pat. No. 6,113,559; IPR2016-01459; 9 pages (Filed Apr. 26, 2017).
Dermafocus Exhibit 2010, A.G. Visioli et al, "Preliminary Results of a Phase I Dose Escalation Clinical Trial Using Focused Ultrasound in the Treatment of Localised Tumours," European Journal of Ultrasound, vol. 9 (1999), 11-18, in Re U.S. Pat. No. 6,113,559; IPR2016-01459; 8 pages (Filed Apr. 26, 2017).
Dermafocus Exhibit 2011, U.S. Pat. No. 5,143,063, issued on Sep. 1,1992, Fellner, in Re U.S. Pat. No. 6,113,559; IPR2016-01459; 6 pages (Filed Apr. 26, 2017).
Dermafocus Exhibit 2012, Hugh G. Beebe et al, "Consensus Statement: Classification and Grading of Chronic Venous Disease in the Lower Limbs," European Journal of Vascular and Endovascular Surgery, vol. 12 (1996), 487-492, in Re U.S. Pat. No. 6,113,559; IPR2016-01459; 6 pages (Filed Apr. 26, 2017).
Dermafocus Exhibit 2013, Excerpt from Mosby's Medical Dictionary (3rd ed. 1990), in Re U.S. Pat. No. 6,113,559; IPR2016-01459; 4 pages (Filed Apr. 26, 2017).
Dermafocus Exhibit 2014, Excerpt from Miller-Keane Encyclopedia & Dictionary of Medicine, Nursing, & Allied Health (5th ed. 1992), in Re U.S. Pat. No. 6,113,559; IPR2016-01459; 6 pages (Filed Apr. 26, 2017).
Dermafocus Exhibit 2015, David J. Tibbs et al, Varicose Veins, Venous Disorders, and Lymphatic Problems in the Lower Limbs (1997), Chapter 4: Clinical Patterns of Venous Disorder I, 47-67, in Re U.S. Pat. No. 6,113,559; IPR2016-01459; 24 pages (Filed Apr. 26, 2017).
Dermafocus Exhibit 2016, Mitchel P. Goldman et al, Varicose Veins and Telangiectasias (2nd ed. 1999), Chapter 22: Treatment of Leg Telangiectasias with Laser and High-Intensity Pulsed Light, 470-497, in Re U.S. Pat. No. 6,113,559; IPR2016-01459; 31 pages (Filed Apr. 26, 2017).
Dermafocus Exhibit 2017, Email from Anderson to Klopotek dated May 25, 2004, in Re U.S. Pat. No. 6,113,559; IPR2016-01459; 1 page (Filed Apr. 26, 2017).
Dermafocus Exhibit 2018, List of Klopotek Patents, in Re U.S. Pat. No. 6,113,559; IPR2016-01459; 411 pages (Filed Apr. 26, 2017).

(56) References Cited

OTHER PUBLICATIONS

Dermafocus Exhibit 2019, Declaration of Peter Klopotek Civil Action 15-cv-654-SLR, dated Nov. 2, 2016, in Re U.S. Pat. No. 6,113,559; IPR2016-01459; 1 page (Filed Apr. 26, 2017).
Dermafocus Exhibit 2020, "Our Technology," downloaded from http://jobs.ulthera.com/about on Apr. 10, 2017, in Re U.S. Pat. No. 6,113,559; IPR2016-01459; 4 pages (Filed Apr. 26, 2017).
Dermafocus Exhibit 2021, C. Damianou and K. Hynynen, "Focal Spacing and Near-Field Heating During Pulsed High Temperature Ultrasound Therapy," Ultrasound in Medicine & Biology, vol. 19, No. 9 (1993), 777-787, in Re U.S. Pat. No. 6,113,559; IPR2016-01459; 11 pages (Filed Apr. 26, 2017).
Dermafocus Exhibit 2022, Excerpt from Mosby's Medical Dictionary (5th ed. 1997), in Re U.S. Pat. No. 6,113,559; IPR2016-01459; 5 pages (Filed Apr. 26, 2017).
Dermafocus Exhibit 2023, Excerpt from Miller-Keane Encyclopedia & Dictionary of Medicine, Nursing, & Allied Health (6th ed. 1997), in Re U.S. Pat. No. 6,113,559; IPR2016-01459; 7 pages (Filed Apr. 26, 2017).
Dermafocus Exhibit 2024, Excerpt from Stedman's Concise Medical Dictionary (3 rd ed. 1997), in Re U.S. Pat. No. 6,113,559; IPR2016-01459; 4 pages (Filed Apr. 26, 2017).
Dermafocus Exhibit 2025, Excerpt from Taber's Cyclopedic Medical Dictionary (18th ed. 1997), in Re U.S. Pat. No. 6,113,559; IPR2016-01459; 9 pages (Filed Apr. 26, 2017).
Dermafocus Exhibit 2026, Bo Eklof et al, "Revision of the CEAP Classification for Chronic Venous Disorders: Consensus Statement," Journal ofVascular Surgery, vol. 40, No. 6 (2004), 1248-1252.el, in Re U.S. Pat. No. 6,113,559; IPR2016-01459; 6 pages (Filed Apr. 26, 2017).
Ulthera, Inc., Reply in Support of Petition for Inter Partes Review in Re U.S. Pat. No. 6,113,559; IPR2016-01459; 33 pages (Filed Aug. 2, 2017).
Ulthera Exhibit 1022, Use of the Argon and Carbon Dioxide Lasers for Treatment of Superficial Venous Varicosities of the Lower Extremity, D. Apfelberg et al., Lasers in Surgery and Medicine, vol. 4.3, pp. 221-231 (1984) (filed Aug. 2, 2017 in re IPR2016-01459).
Ulthera Exhibit 1023, 532-Nanometer Green Laser Beam Treatment of Superficial Varicosities of the Lower Extremities, T. Smith et al., Lasers in Surgery and Medicine, vol. 8.2, pp. 130-134 (1988) (filed Aug. 2, 2017 in re IPR2016-01459).
Ulthera Exhibit 1024, Deposition Transcript of Dr. Mark Palmeri on Jul. 11, 2017 (filed Aug. 2, 2017 in re IPR2016-01459).
Carruthers et al., "Consensus Recommendations for Combined Aesthetic Interventions in the Face Using Botulinum Toxin, Fillers,and Energy-Based Devices" Dermatol Surg 2016 (pp. 1-12).
Final Written Decision of Inter Partes Review in Re U.S. Pat. No. 6,113,559; IPR2016-01459; 37 pages [030] (Entered Jan. 19, 2018).

* cited by examiner

ULTRASOUND PROBE FOR TREATING SKIN LAXITY

INCORPORATION BY REFERENCE TO ANY PRIORITY APPLICATIONS

This application is a continuation of U.S. patent application Ser. No. 15/625,700, issued at U.S. Pat. No. 9,827,449, which is a continuation of U.S. patent application Ser. No. 15/248,407, issued as U.S. Pat. No. 9,694,211, which is a continuation of U.S. patent application Ser. No. 14/692,114, issued as U.S. Pat. No. 9,427,600, which is a continuation of U.S. patent application Ser. No. 14/169,709, issued as U.S. Pat. No. 9,039,619, which is a continuation of U.S. patent application Ser. No. 13/230,498, issued as U.S. Pat. No. 8,641,622, which is a continuation of U.S. patent application Ser. No. 11/163,150, issued as U.S. Pat. No. 8,066,641, which claims the benefit of priority to U.S. Provisional Application No. 60/617,295, each of which is incorporated in its entirety by reference herein. Any and all applications for which a foreign or domestic priority claim is identified in the Application Data Sheet as filed with the present application are hereby incorporated by reference under 37 CFR 1.57.

BACKGROUND

The present invention relates to ultrasound therapy and imaging systems, and in particular to a method and system for treating photoaged tissue.

Photoaging of human skin is a complex response due to inflammation, oxidative injury, cellular and extracellular changes induced by decades of sunlight exposure. UV wavelengths are thought to be mainly responsible. Both of the primary skin layers, epidermis and dermis, are affected. Epidermal photoaging includes pigmentary lesions called ephilides (freckles) and solar lentigines (larger pigmented spots), plus precancerous clonal lesions of keratinocytes called actinic keratoses. Thermal destruction of part or all of the epidermis, the outermost cellular layer of skin about 0.1 mm thick, is an effective treatment for epidermal photoaging. For example, lasers that vaporize epidermis are highly effective in a treatment called laser resurfacing. However laser resurfacing creates a significant skin wound with risk of infection, and prolonged healing. Dermal changes of photoaging include solar elastosis (an accumulation of abnormally-formed elastin fibers in the upper reticular layer of the dermis), laxity, loss of elasticity, fine and coarse wrinkles. Laser resurfacing to a depth below the dermoepidermal junction can be highly effective for improving dermal photoaging, through a process of stimulated wound healing. Deep chemical peels, dermabrasion and other methods of destruction of epidermis and/or dermis are also effective, and also produce a significant open skin wound with risk of infection and delayed healing.

Patterns of stimulated thermal damage to epidermis and/or dermis are also effective for treatment of photoaging. Recently, "fractional photothermolysis" using mid-infrared lasers to produce a microscopic array of thermal injury zones that include both epidermis and dermis was reported to be effective and well-tolerated for treatment of photoaging (D. Manstein et al. "Fractional Photothermolysis: a new concept for cutaneous remodeling using microscopic patterns of thermal injury." Lasers Surg Med 34:426-438, 2004). A primary advantage of fractional photothermolysis is that each zone of thermal injury is smaller than can be easily seen with the unaided eye, and surrounded by a zone of healthy tissue that initiates a rapid healing response. As described Manstein, the epidermis is stimulated to heal rapidly and without creating an open wound. The microscopic zones of thermally injured epidermis slough harmlessly from the skin surface after several days to several weeks, leaving a rejuvenated epidermis with less photoaging changes. Repeat treatments, which are well tolerated, can be performed until a desired result is obtained. The microscopic zones of thermal injury with fractional photothermolysis extend well into the dermis, as well. Dermis does not heal as rapidly as epidermis, in general. Over weeks to months following treatment, some of the abnormal dermis due to photoaging is remodeled, however, leading to improvement in laxity, wrinkles and skin texture.

Fractional photothermolysis (FP) is intrinsically limited to regions of approximately the upper 1-millimeter of skin. The basic concept of producing well-controlled arrays of thermal injury is therefore limited with fractional photothermolysis, to superficial aspects of photoaging. Aging, which also causes laxity of the skin, and photoaging involve deeper layers of the dermis. Solar elastosis can extend throughout the dermis, to approximately 3 mm deep or more. Laxity and loss of elasticity due to aging are bulk problems of the dermis.

A fundamental requirement for producing arrays of small thermal injury zones using a source of radiant energy that propagates and is absorbed within tissue, is that the source of radiant energy be capable of being adequately delivered to the tissue depth for which the array is desired. Near the skin surface, light can be used, as in fractional photothermolysis. However, light that propagates more than about 1 mm through skin has been multiplied scattered, and can no longer be focused or delivered.

SUMMARY

A method and system for ultrasound treatment of photoaged tissue are provided. An exemplary method and system are configured for first, ultrasound imaging of the region of interest for localization of the treatment area, second, delivery of ultrasound energy at a depth and pattern to achieve the desired therapeutic effects, and third to monitor the treatment area during and after therapy to assess the results and/or provide feedback. The exemplary treatment method and system can be configured for producing arrays of sub-millimeter and larger zones of thermal ablation to treat the epidermal, superficial dermal, mid-dermal and deep dermal components of photoaged tissue.

In accordance with an exemplary embodiment, the treatment method and system use focused, unfocused, and/or defocused ultrasound for treatment of epidermal, superficial dermal, dermal, mid-dermal, and/or deep dermal components of photoaged tissue by adjusting the strength, depth, and/or type of focusing, energy levels and timing cadence. For example, focused ultrasound can be used to create precise arrays of microscopic thermal damage much deeper into the skin or even into subcutaneous structures. Detection of changes in the reflection of ultrasound can be used for feedback control to detect a desired effect on the tissue and used to control the exposure intensity, time, and/or position.

In accordance with an exemplary embodiment, an exemplary treatment system comprises an imaging/therapy probe, a control system and display system. The imaging/therapy probe can comprise various probe and/or transducer configurations. For example, the probe can be configured for a combined dual-mode imaging/therapy transducer, coupled or co-housed imaging/therapy transducers, a separate therapy probe and imaging probe, or a single therapy probe. The control system and display system can also comprise various configurations for controlling probe and system functionality, including for example a microprocessor with software and a plurality of input/output and communication devices, a system for controlling electronic and/or mechanical scanning and/or multiplexing of transducers, a system for power delivery, systems for monitoring, systems for sensing the spatial position of the probe and/or temporal parameters of the transducers, and systems for handling user input and recording treatment input and results, among others.

BRIEF DESCRIPTION OF THE DRAWINGS

The subject matter of the invention is particularly pointed out in the concluding portion of the specification. The invention, however, both as to organization and method of operation, may best be understood by reference to the following description taken in conjunction with the accompanying drawing figures, in which like parts may be referred to by like numerals.

DETAILED DESCRIPTION

Figure 1:
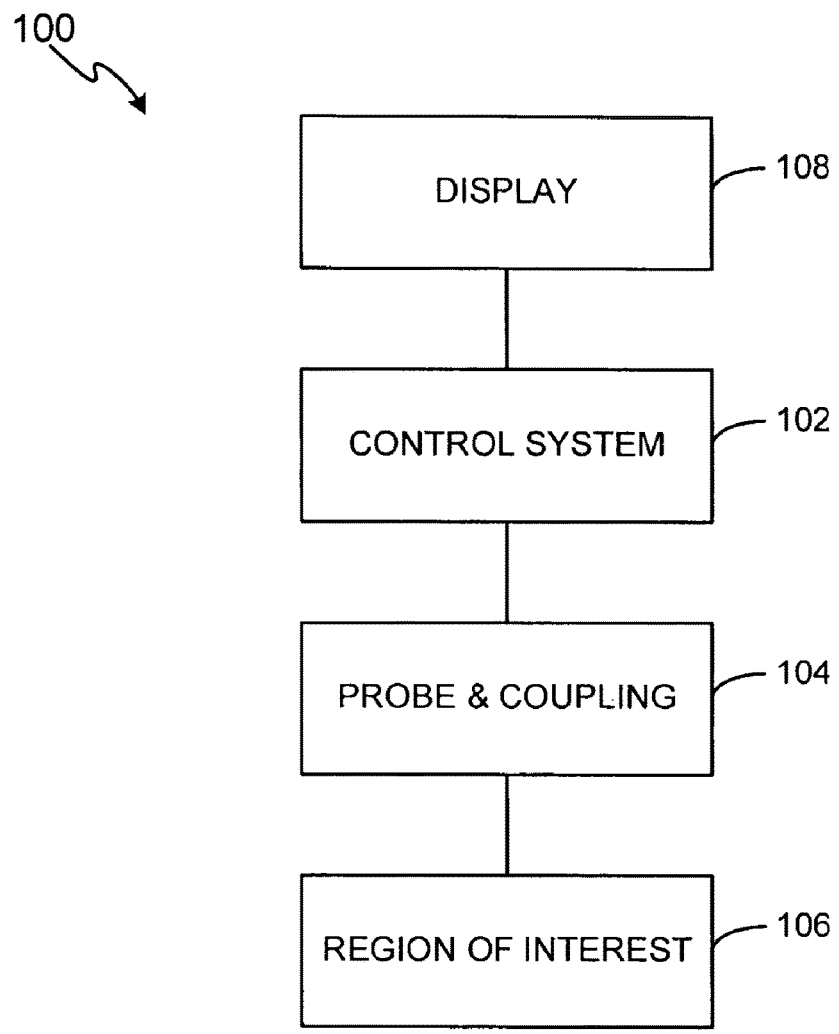
FIG. 1 illustrates a block diagram of a treatment system in accordance with an exemplary embodiment of the present invention.

The present invention may be described herein in terms of various functional components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical contexts and that the exemplary embodiments relating to a method and system for treating photoaged tissue as described herein are merely indicative of exemplary applications for the invention. For example, the principles, features and methods discussed may be applied to any medical application. Further, various aspects of the present invention may be suitably applied to other applications.

In accordance with various aspects of the present invention, a method and system for treating photoaged tissue are provided. For example, in accordance with an exemplary embodiment, with reference to FIG. 1, an exemplary treatment system 100 configured to treat a region of interest (ROI) 106 comprises a control system 102, an imaging/therapy probe with acoustic coupling 104, and a display system 108. Control system 102 and display 108 can comprise various configurations for controlling functionality of probe 104 and system 100, including for example a microprocessor with software and a plurality of input/output and communication devices, a system for controlling electronic and/or mechanical scanning and/or multiplexing of transducers, a system for power delivery, systems for monitoring, systems for sensing the spatial position of the probe and/or temporal parameters of the transducers, and/or systems for handling user input and recording treatment input and results, among others. Imaging/therapy probe 104 can comprise various probe and/or transducer configurations. For example, probe 104 can be configured for a combined dual-mode imaging/therapy transducer, coupled or co-housed imaging/therapy transducers, a separate therapy probe and separate imaging probe, or a single therapy probe. In accordance with exemplary embodiments, imaging transducers may operate at frequencies from approximately 2 to 75 MHz or more, while therapy energy can be delivered at frequencies from approximately 2 to 50 MHz, with 2 MHz to 25 MHz being typical.

For the treatment of photoaged tissue, it is desirable to be able to produce well controlled arrays of microscopic zones of thermal injury not only near the surface of skin, but in the mid-dermis, and/or in the deep dermis. Thermal ablation of dermis at temperatures greater than about 60° C., capable of producing denaturation of tissue, is also desirable in such arrays of thermal lesions. Shrinkage of dermis due to thermal action results from tightening of the skin.

In contrast to optical or RF approaches, ultrasound energy propagates as a wave with relatively little scattering, over depths up to many centimeters in tissue depending on the ultrasound frequency. The focal spot size achievable with any propagating wave energy, depends on wavelength. Ultrasound wavelength is equal to the acoustic velocity divided by the ultrasound frequency. Attenuation (absorption, mainly) of ultrasound by tissue also depends on frequency.

In accordance with an exemplary embodiment, the use of focused, unfocused, or defocused ultrasound for treatment of epidermal, superficial dermal, dermal, middermal, and deep dermal components of photoaged tissue through adjustment of the strength, depth, and type of focusing, energy levels and timing cadence. For example, focused ultrasound can be used to create precise arrays of microscopic thermal ablation zones which have several advantages over fractional photothermolysis (FP). At high frequency and with superficial focusing or diffraction pattern, ultrasound ablation can mimic FP but utilize a simpler ablation device. Unlike fractional photothermolysis, ultrasound can produce an array of ablation zones much deeper into the skin or even into subcutaneous structures. Detection of changes in the reflection of ultrasound can be used for feedback control to detect a desired effect on the tissue and used to control the exposure intensity, time, and/or position.

Figure 2A:
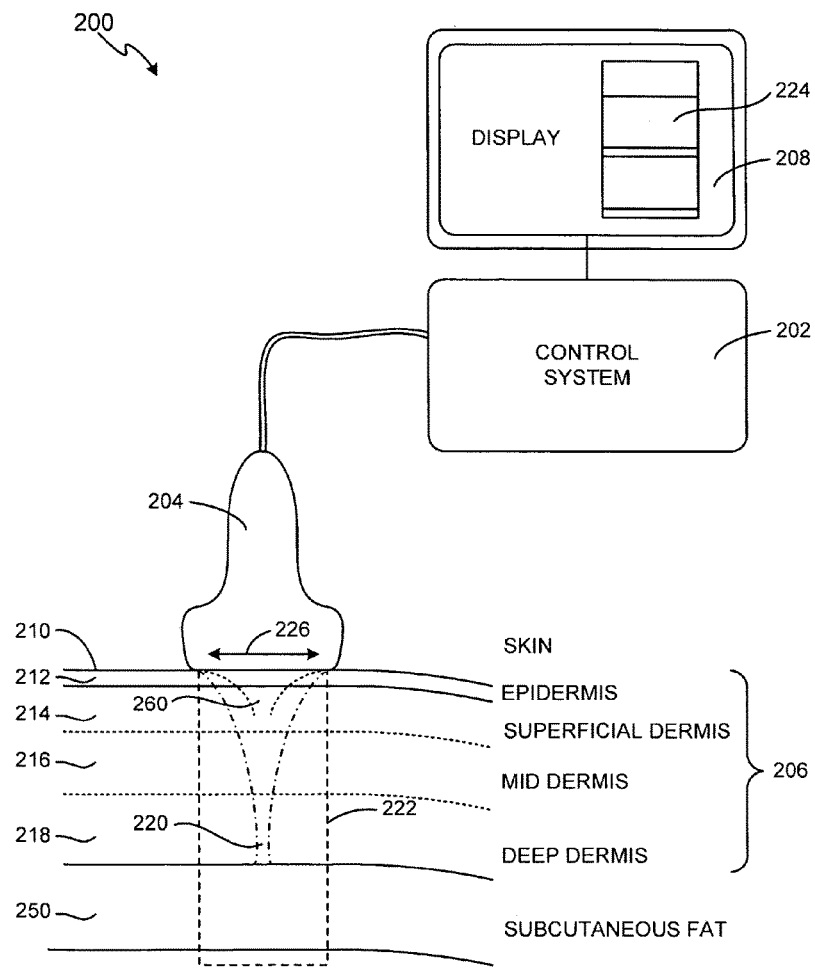
FIGS. 2A-2D illustrates a schematic diagram of an ultrasound treatment system including therapy, imaging and/or monitoring and treating photoaged tissue in accordance with various exemplary embodiments of the present invention.

To further illustrate the use of ultrasound for the treatment of photoaged tissue, with reference to FIG. 2A, an exemplary method and system are configured for initially imaging a region 222 of a region of interest 206 and displaying that region 224 during the localization of the treatment area and surrounding structures. After localization, delivery of ultrasound energy 220 at a depth, distribution, timing, and energy level to achieve the desired therapeutic effect of thermal ablation to treat an epidermis layer 212, superficial dermis layer 214, mid-dermis layer 216, and/or deep dermis layer 218 can be provided. Before, during, and after therapy, i.e., before, during, and after the delivery of ultrasound energy 220, exemplary method and system 200 can suitably monitor the treatment area and surrounding structures to plan and assess the results and/or provide feedback to control system 202 and/or a system user.

While an imaging function may be configured within control system 202 to facilitate imaging a region of interest, in accordance with another exemplary embodiment, an exemplary treatment system 200 may also be configured for therapy only or therapy and monitoring, without imaging functions. In such a case prior known depth of the region of interest, approximately 0 to 5 mm or less, is employed to achieve treatment zones in photoaged skin.

Probe 204 and/or transducers within can be mechanically and/or electronically scanned in a direction 226 to place treatment zones 260 over an extended area, such as a line to generate a matrix of closely spaced treatment spots. Treatment depth 220 can be adjusted between a range of approximately 0 to 5 mm, or otherwise until the depth of the deep dermis. Treatment may be confined to a fixed depth or a few discrete depths, or can be adjustment limited to a fine range, e.g. from approximately between 0 to 5 mm or the greatest depth of the deep dermis, or can be dynamically adjusted during treatment, to the treat region of interest 206 that lies above subcutaneous fat region 250.

Figure 2B:
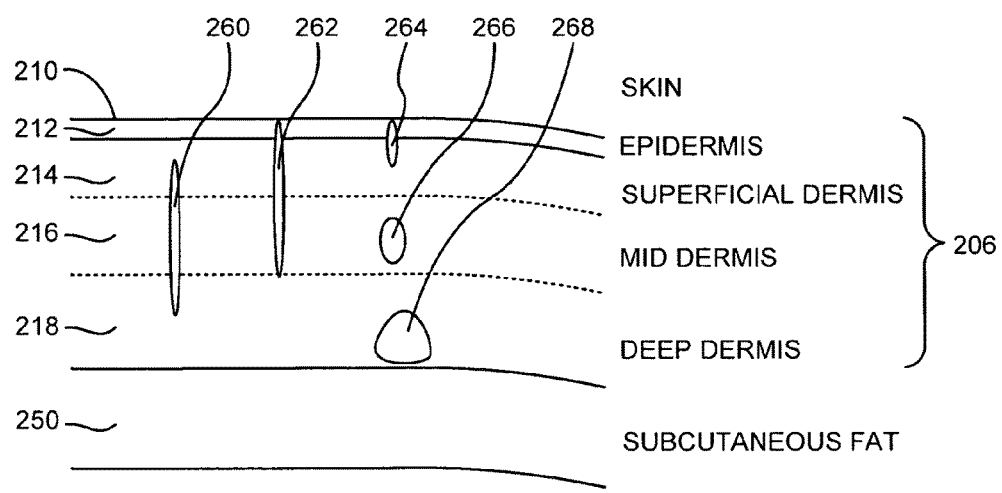

In accordance with another exemplary embodiment of the present invention, with reference to FIG. 2B, a treated zone 260 may extend throughout regions of the dermis, and may even extend to the epidermis, 262. In addition, as a treated zone increases in depth its cross section may increase from small size 264 (sub millimeter) in a shallow region near or at the epidermis, to medium size 266 (sub millimeter to millimeter sized) in a middle zone near or at the mid dermis, to large size 268 (millimeter sized) in deep zones near or at the deep dermis. Furthermore a single treated zone can have a shape expanding in cross section with depth, and/or be composed of the fusion of several smaller treatment zones. Spacing of treatment zones can be on the order of the treatment zone size. The ultrasound beam can be spatially and/or temporally controlled by changing the position of the transducer, its frequency, treatment depth, drive amplitude, and timing via the control system. For example, the ultrasound beam can be controlled as set forth in U.S. patent application Ser. No. 11/163,148, filed Oct. 6, 2005, and entitled METHOD AND SYSTEM FOR CONTROLLED THERMAL INJURY OF HUMAN SUPERFICIAL TISSUE, and hereby incorporated by reference.

Figure 2C:
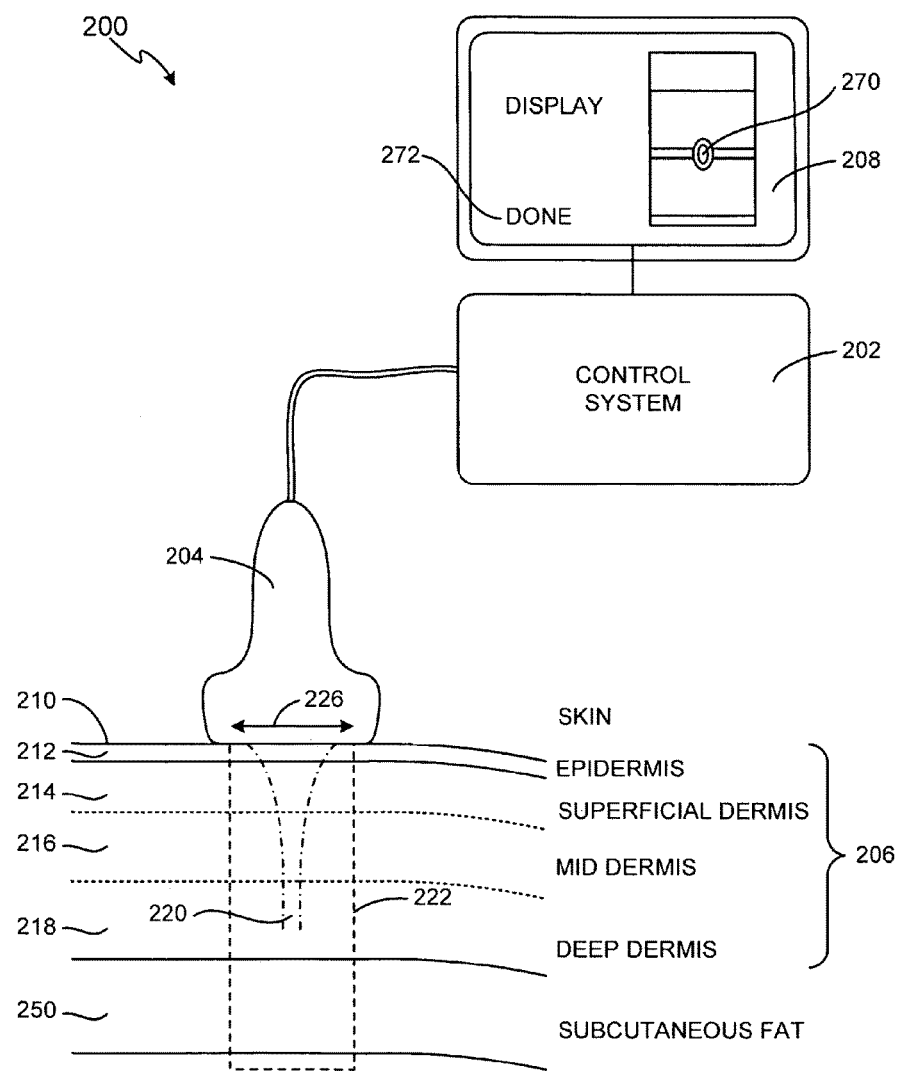
Figure 2D:
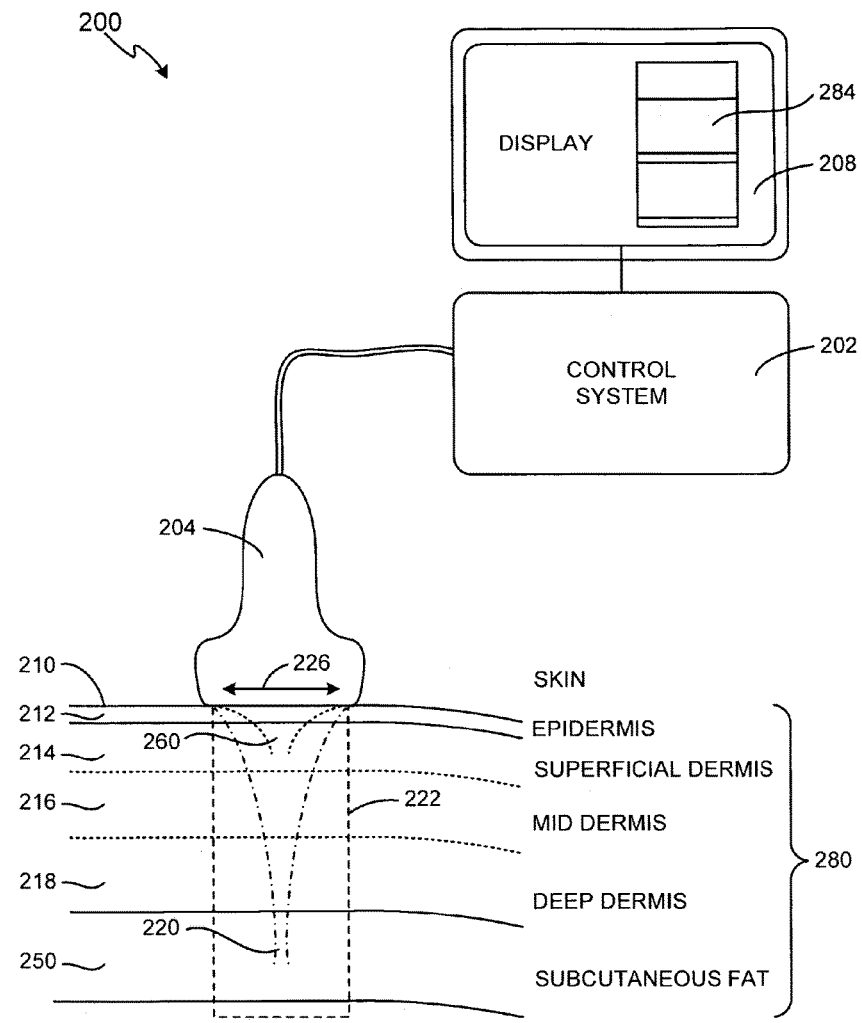

In accordance with another exemplary embodiment of the present invention, with reference to FIG. 2C, an exemplary treatment method and system 200 may be configured to monitor the temperature profile or other tissue parameters of region of interest 206, such as attenuation or speed of sound of the treatment region and suitably adjust the spatial and/or temporal characteristics and energy levels of the ultrasound therapy transducer. The results of such monitoring techniques may be indicated on display 208, such as through display of one-, two-, or three-dimensional images of monitoring results 270, or may comprise an indicator 272, such as a success, fail and/or completed/done type of indication, or combinations thereof. Additional treatment monitoring methods may be based on one or more of temperature, video, profilometry, strain imaging and/or gauges or any other suitable sensing method.

In accordance with another exemplary embodiment, with reference to FIG. 2O, an expanded region of interest 280 can suitably include a combination of tissues, such as subcutaneous fat/adipose tissue 250. A combination of such tissues includes at least one of epidermis 212, superficial dermis 214, mid dermis 216, or deep dermis 218, in combination with at least one of muscle tissue, adipose tissue, or other tissues useful for treatment. For example, treatment 260 of superficial dermis may be performed in combination with treatment 220 of subcutaneous fat 250 by suitable adjustment of the spatial and temporal parameters of transducers in probe 204.

Figure 3A:
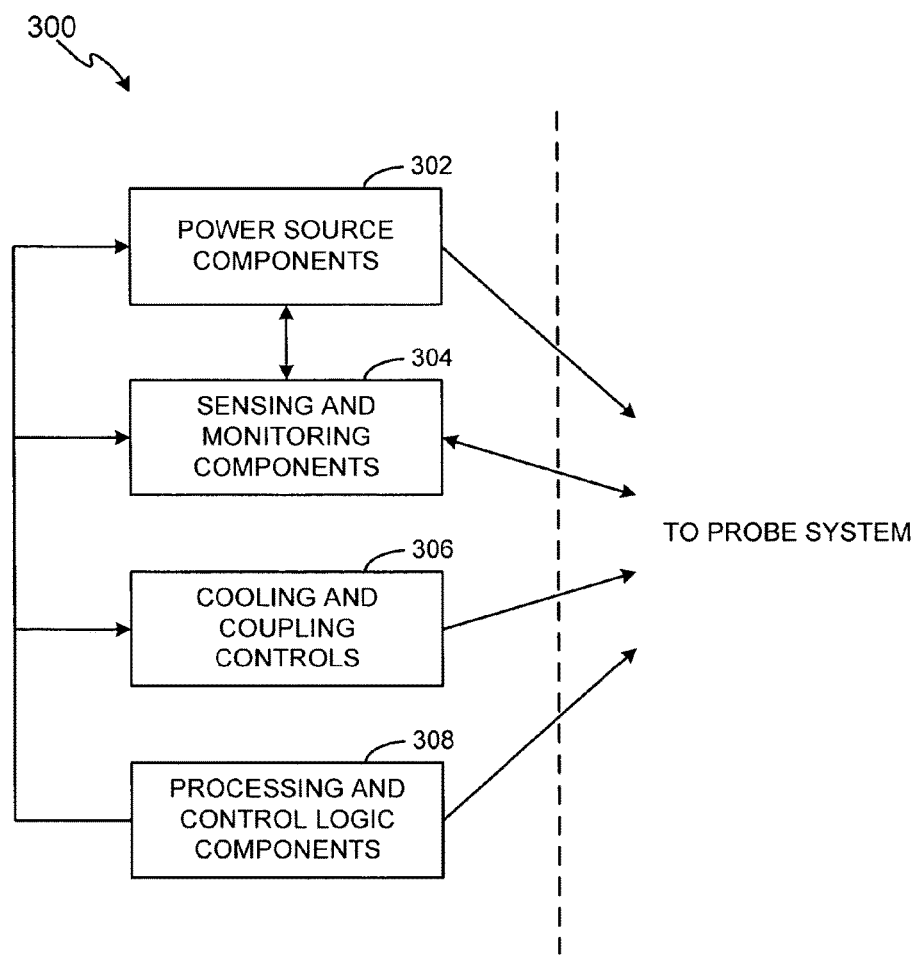
FIGS. 3A and 3B illustrate block diagrams of an exemplary control system in accordance with exemplary embodiments of the present invention.
Figure 3B:
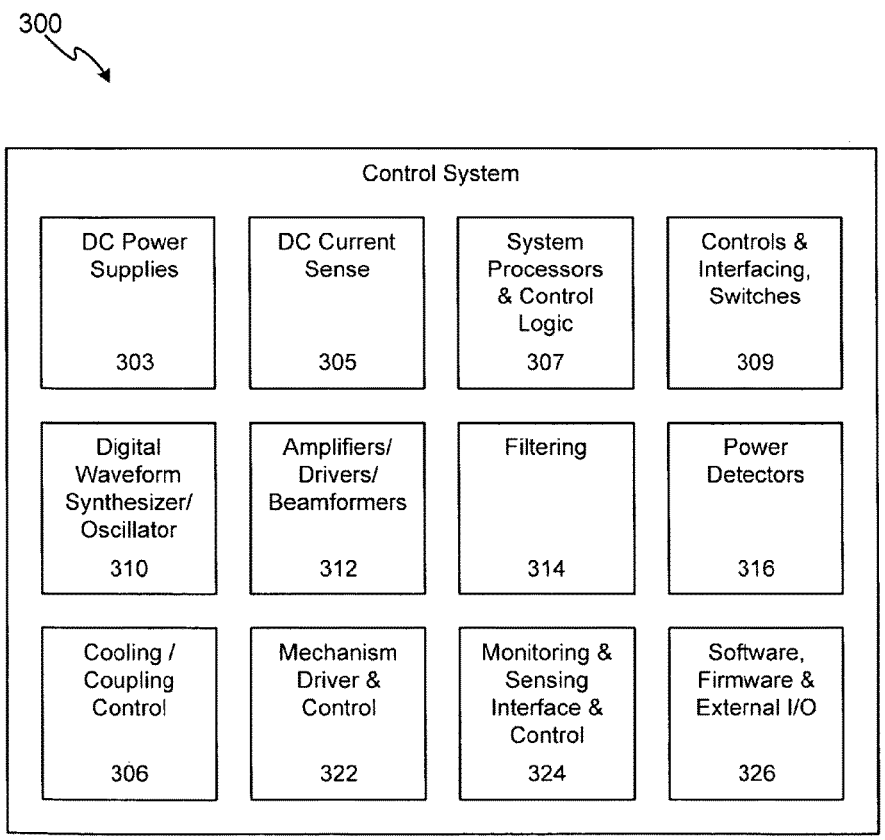

An exemplary control system 202 and display system 208 may be configured in various manners for controlling probe and system functionality for providing the various exemplary treatment methods illustrated above. For example, with reference to FIGS. 3A and 3B, in accordance with exemplary embodiments, an exemplary control system 300 can be configured for coordination and control of the entire therapeutic treatment process for producing arrays of sub-millimeter and larger zones of thermal ablation to treat the epidermal, superficial dermal, mid-dermal and deep dermal components of photoaged tissue. For example, control system 300 can suitably comprise power source components 302, sensing and monitoring components 304, cooling and coupling controls 306, and/or processing and control logic components 308. Control system 300 can be configured and optimized in a variety of ways with more or less subsystems and components to implement the therapeutic system for controlled thermal injury of photoaged tissue, and the embodiments in FIGS. 3A and 3B are merely for illustration purposes.

For example, for power sourcing components 302, control system 300 can comprise one or more direct current (DC) power supplies 303 configured to provide electrical energy for entire control system 300, including power required by a transducer electronic amplifier/driver 312. A DC current sense device 305 can also be provided to confirm the level of power going into amplifiers/drivers 312 for safety and monitoring purposes.

Amplifiers/drivers 312 can comprise multi-channel or single channel power amplifiers and/or drivers. In accordance with an exemplary embodiment for transducer array configurations, amplifiers/drivers 312 can also be configured with a beamformer to facilitate array focusing. An exemplary beamformer can be electrically excited by an oscillator/digitally controlled waveform synthesizer 310 with related switching logic.

The power sourcing components can also include various filtering configurations 314. For example, switchable harmonic filters and/or matching may be used at the output of amplifier/driver 312 to increase the drive efficiency and effectiveness. Power detection components 316 may also be included to confirm appropriate operation and calibration. For example, electric power and other energy detection components 316 may be used to monitor the amount of power going to an exemplary probe system.

Various sensing and monitoring components 304 may also be suitably implemented within control system 300. For example, in accordance with an exemplary embodiment, monitoring, sensing and interface control components 324 may be configured to operate with various motion detection systems implemented within transducer probe 204 to receive and process information such as acoustic or other spatial and temporal information from a region of interest. Sensing and monitoring components can also include various controls, interfacing and switches 309 and/or power detectors 316. Such sensing and monitoring components 304 can facilitate open-loop and/or closed-loop feedback systems within treatment system 200.

Cooling/coupling control systems 306 may be provided to remove waste heat from an exemplary probe 204, provide a controlled temperature at the superficial tissue interface and deeper into tissue, and/or provide acoustic coupling from transducer probe 204 to region-of-interest 206. Such cooling/coupling control systems 306 can also be configured to operate in both open-loop and/or closed-loop feedback arrangements with various coupling and feedback components.

Processing and control logic components 308 can comprise various system processors and digital control logic 307, such as one or more of microcontrollers, microprocessors, field-programmable gate arrays (FPGAs), computer boards, and associated components, including firmware and control software 326, which interfaces to user controls and interfacing circuits as well as input/output circuits and systems for communications, displays, interfacing, storage, documentation, and other useful functions. System software and firmware 326 controls all initialization, timing, level setting, monitoring, safety monitoring, and all other system functions required to accomplish user-defined treatment objectives. Further, various control switches 308 can also be suitably configured to control operation.

An exemplary transducer probe 204 can also be configured in various manners and comprise a number of reusable and/or disposable components and parts in various embodiments to facilitate its operation. For example, transducer probe 204 can be configured within any type of transducer probe housing or arrangement for facilitating the coupling of transducer to a tissue interface, with such housing comprising various shapes, contours and configurations. Transducer probe 204 can comprise any type of matching, such as for example, electric matching, which may be electrically switchable; multiplexer circuits and/or aperture/element selection circuits; and/or probe identification devices, to certify probe handle, electric matching, transducer usage history and calibration, such as one or more serial EEPROM (memories). Transducer probe 204 may also comprise cables and connectors; motion mechanisms, motion sensors and encoders; thermal monitoring sensors; and/or user control and status related switches, and indicators such as LEDs. For example, a motion mechanism in probe 204 may be used to controllably create multiple lesions, or sensing of probe motion itself may be used to controllably create multiple lesions and/or stop creation of lesions, e.g. for safety reasons if probe 204 is suddenly jerked or is dropped. In addition, an external motion encoder arm may be used to hold the probe during use, whereby the spatial position and attitude of probe 104 is sent to the control system to help controllably create lesions. Furthermore, other sensing functionality such as profilometers or other imaging modalities may be integrated into the probe in accordance with various exemplary embodiments.

Figure 4A:
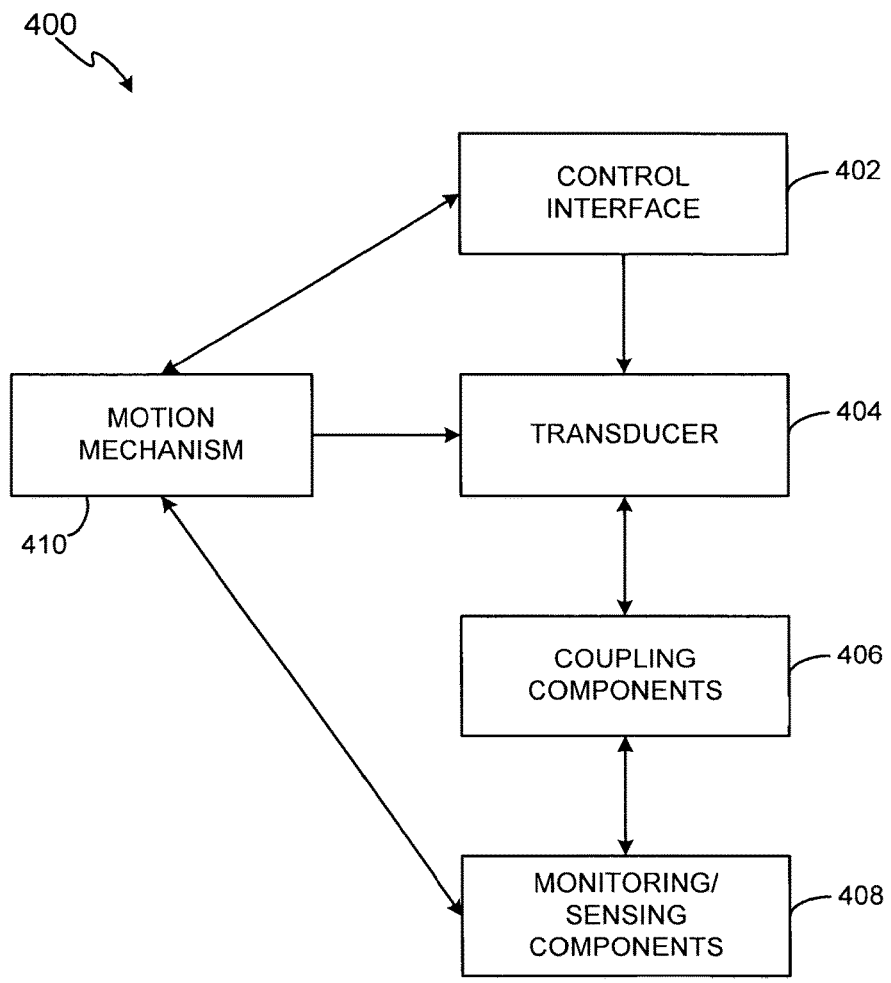
FIGS. 4A and 4B illustrate block diagrams of an exemplary probe system in accordance with exemplary embodiments of the present invention.
Figure 4B:
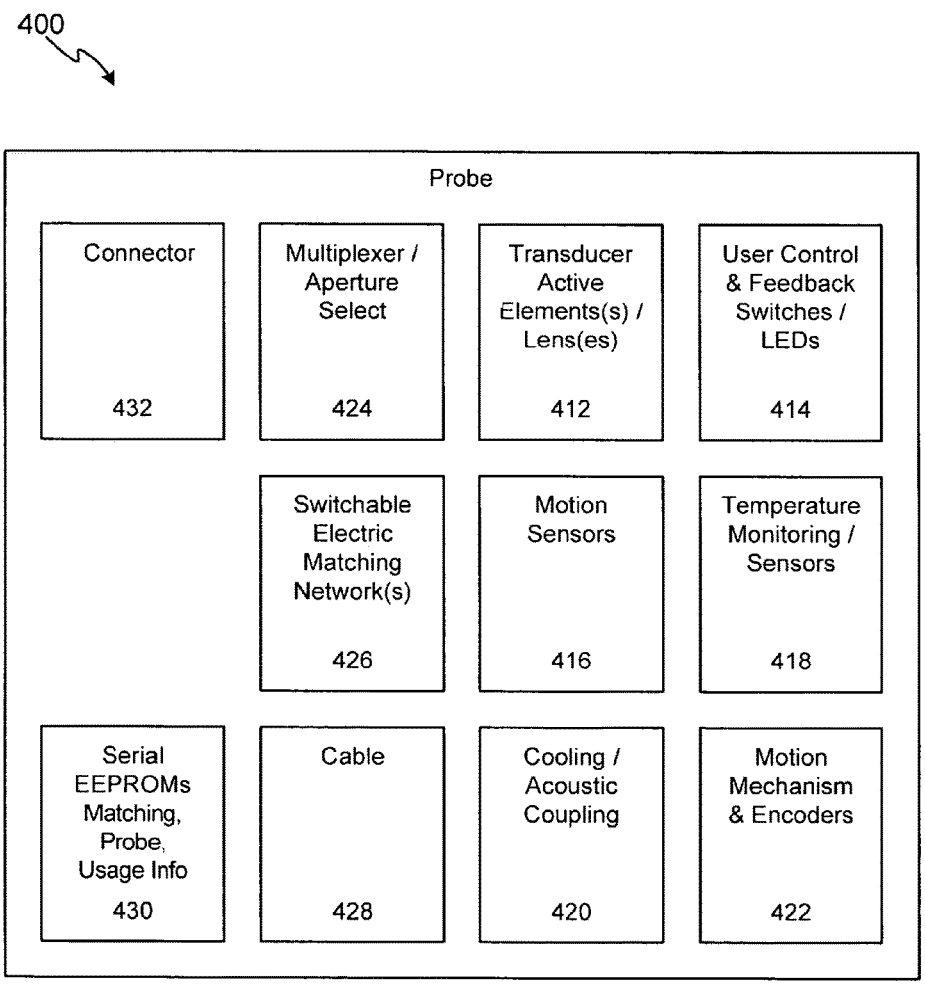

With reference to FIGS. 4A and 4B, in accordance with an exemplary embodiment, a transducer probe 400 can comprise a control interface 402, a transducer 404, coupling components 406, and monitoring/sensing components 408, and/or motion mechanism 410. However, transducer probe 400 can be configured and optimized in a variety of ways with more or less parts and components to provide ultrasound energy for controlled thermal injury of photoaged tissue, and the embodiments in FIGS. 4A and 4B are merely for illustration purposes.

Control interface 402 is configured for interfacing with control system 300 to facilitate control of transducer probe 400. Control interface components 402 can comprise multiplexer/aperture select 424, switchable electric matching networks 426, serial EEPROMs and/or other processing components and matching and probe usage information 430 and interface connectors 432.

Coupling components 406 can comprise various devices to facilitate coupling of transducer probe 400 to a region of interest. For example, coupling components 406 can comprise cooling and acoustic coupling system 420 configured for acoustic coupling of ultrasound energy and signals. Acoustic cooling/coupling system 420 with possible connections such as manifolds may be utilized to couple sound into the region-of-interest, control temperature at the interface and deeper into tissue, provide liquid-filled lens focusing, and/or to remove transducer waste heat. Coupling system 420 may facilitate such coupling through use of various coupling mediums, including air and other gases, water and other fluids, gels, solids, and/or any combination thereof, or any other medium that allows for signals to be transmitted between transducer active elements 412 and a region of interest. In addition to providing a coupling function, in accordance with an exemplary embodiment, coupling system 420 can also be configured for providing temperature control during the treatment application. For example, coupling system 420 can be configured for controlled cooling of an interface surface or deeper region between transducer probe 400 and a region of interest and beyond by suitably controlling the temperature of the coupling medium. The suitable temperature for such coupling medium can be achieved in various manners, and utilize various feedback systems, such as thermocouples, thermistors or any other device or system configured for temperature measurement of a coupling medium. Such controlled cooling can be configured to further facilitate spatial and/or thermal energy delivery control of transducer probe 400.

Figure 11:
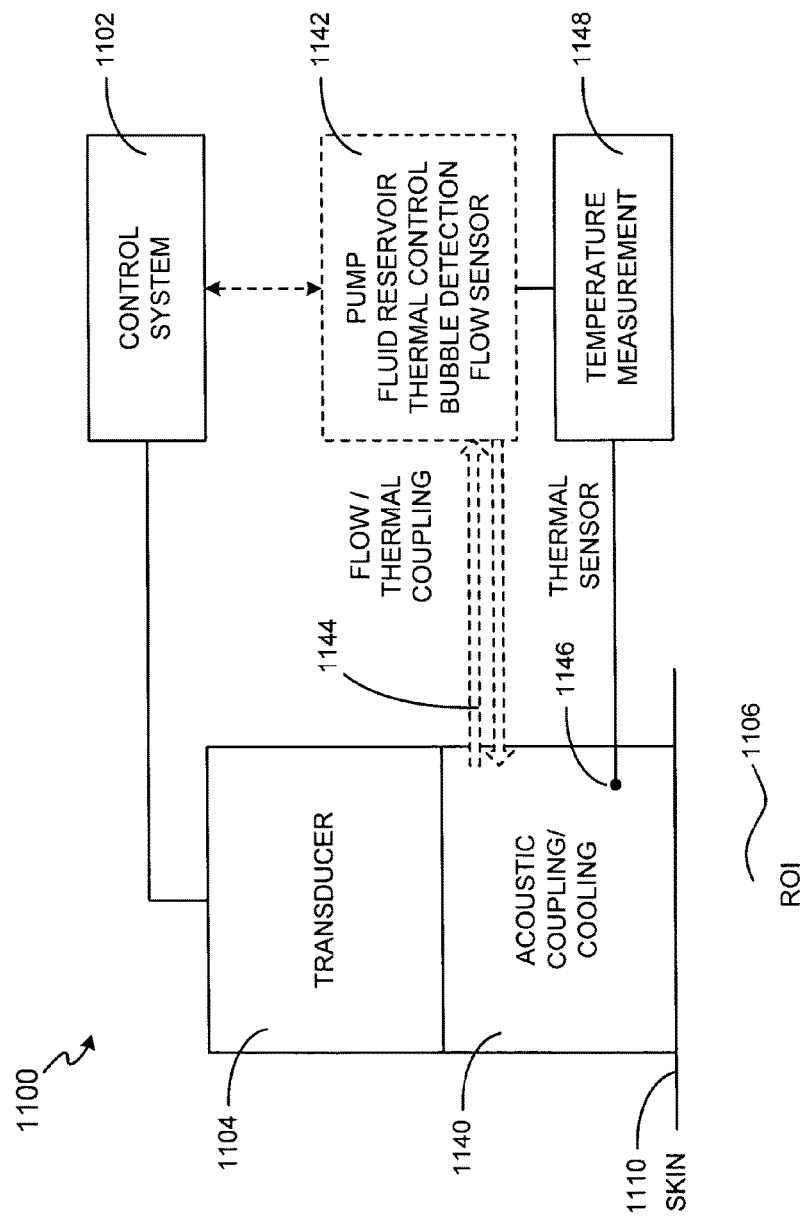
FIG. 11 illustrates a schematic diagram of an acoustic coupling and cooling system in accordance with an exemplary embodiment of the present invention.

In accordance with an exemplary embodiment, with additional reference to FIG. 11, acoustic coupling and cooling 1140 can be provided to acoustically couple energy and imaging signals from transducer probe 1104 to and from the region of interest 1102, to provide thermal control at the probe to region-of-interest interface 1110 and deeper into tissue, and to remove potential waste heat from the transducer probe at region 1144. Temperature monitoring can be provided at the coupling interface via a thermal sensor 1146 to provide a mechanism of temperature measurement 1148 and control via control system 1106 and a thermal control system 1142. Thermal control may consist of passive cooling such as via heat sinks or natural conduction and convection or via active cooling such as with peltier thermo-electric coolers, refrigerants, or fluid-based systems comprised of pump, fluid reservoir, bubble detection, flow sensor, flow channels/tubing 1144 and thermal control 1142.

With continued reference to FIG. 4, monitoring and sensing components 408 can comprise various motion and/or position sensors 416, temperature monitoring sensors 418, user control and feedback switches 414 and other like components for facilitating control by control system 300, e.g., to facilitate spatial and/or temporal control through open-loop and closed-loop feedback arrangements that monitor various spatial and temporal characteristics.

Motion mechanism 410 can comprise manual operation, mechanical arrangements, or some combination thereof. For example, a motion mechanism 422 can be suitably controlled by control system 300, such as through the use of accelerometers, encoders or other position/orientation devices 416 to determine and enable movement and positions of transducer probe 400. Linear, rotational or variable movement can be facilitated, e.g., those depending on the treatment application and tissue contour surface.

Transducer 404 can comprise one or more transducers configured for treating of SMAS layers and targeted regions. Transducer 404 can also comprise one or more transduction elements and/or lenses 412. The transduction elements can comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. In addition to, or instead of, a piezoelectrically active material, transducer 404 can comprise any other materials configured for generating radiation and/or acoustical energy. Transducer 404 can also comprise one or more matching layers configured along with the transduction element such as coupled to the piezoelectrically active material. Acoustic matching layers and/or damping may be employed as necessary to achieve the desired electroacoustic response.

In accordance with an exemplary embodiment, the thickness of the transduction element of transducer 404 can be configured to be uniform. That is, a transduction element 412 can be configured to have a thickness that is substantially the same throughout. In accordance with another exemplary embodiment, the thickness of a transduction element 412 can also be configured to be variable. For example, transduction element(s) 412 of transducer 404 can be configured to have a first thickness selected to provide a center operating frequency of approximately 2 kHz to 75 MHz, such as for imaging applications. Transduction element 412 can also be configured with a second thickness selected to provide a center operating frequency of approximately 2 to 50 MHz, and typically between 2 MHz and 25 MHz for therapy application. Transducer 404 can be configured as a single broadband transducer excited with at least two or more frequencies to provide an adequate output for generating a desired response. Transducer 404 can also be configured as two or more individual transducers, wherein each transducer comprises one or more transduction element. The thickness of the transduction elements can be configured to provide center-operating frequencies in a desired treatment range.

Figure 5:
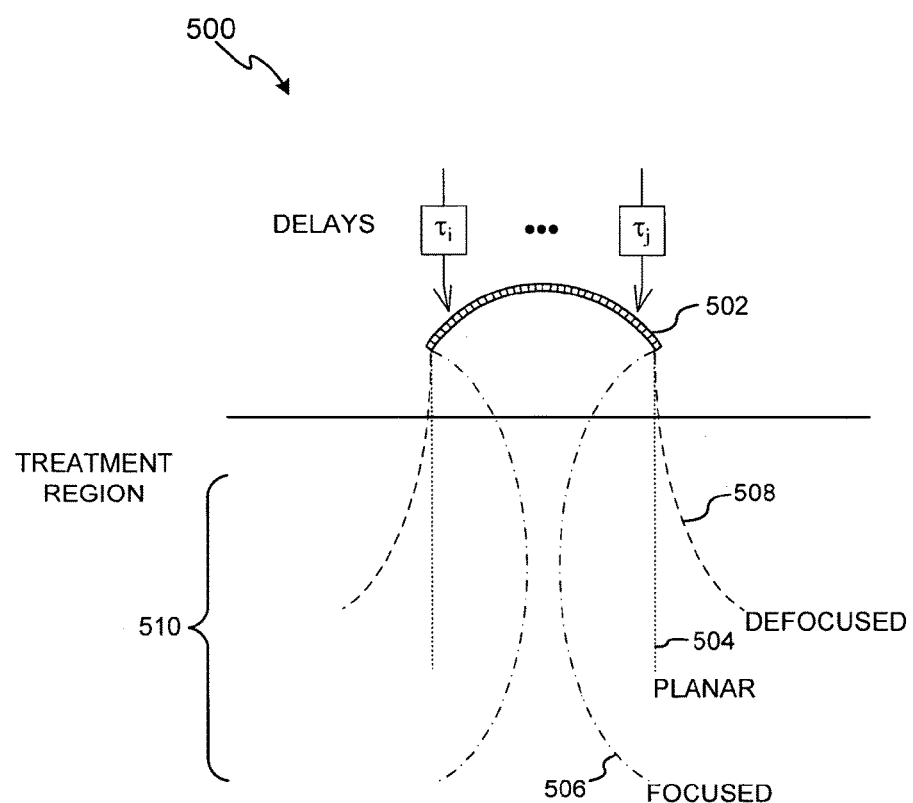
FIG. 5 illustrates a cross-sectional diagram of an exemplary transducer in accordance with an exemplary embodiment of the present invention.

Transducer 404 may be composed of one or more individual transducers in any combination of focused, planar, or unfocused single-element, multi-element, or array transducers, including 1-D, 2-D, and annular arrays; linear, curvilinear, sector, or spherical arrays; spherically, cylindrically, and/or electronically focused, defocused, and/or lensed sources. For example, with reference to an exemplary embodiment depicted in FIG. 5, transducer 500 can be configured as an acoustic array 502 to facilitate phase focusing. That is, transducer 500 can be configured as an array of electronic apertures that may be operated by a variety of phases via variable electronic time delays. By the term "operated," the electronic apertures of transducer 500 may be manipulated, driven, used, and/or configured to produce and/or deliver an energy beam corresponding to the phase variation caused by the electronic time delay. For example, these phase variations can be used to deliver defocused beams 508, planar beams 504, and/or focused beams 506, each of which may be used in combination to achieve different physiological effects in a region of interest 510. Transducer 500 may additionally comprise any software and/or other hardware for generating, producing and/or driving a phased aperture array with one or more electronic time delays.

Transducer 500 can also be configured to provide focused treatment to one or more regions of interest using various frequencies. In order to provide focused treatment, transducer 500 can be configured with one or more variable depth devices to facilitate treatment. For example, transducer 500 may be configured with variable depth devices disclosed in U.S. patent application Ser. No. 10/944,500, entitled "System and Method for Variable Depth Ultrasound", filed on Sep. 16, 2004, having at least one common inventor and a common Assignee as the present application, and incorporated herein by reference. In addition, transducer 500 can also be configured to treat one or more additional ROI 510 through the enabling of sub-harmonics or pulseecho imaging, as disclosed in U.S. patent application Ser. No. 10/944,499, entitled "Method and System for Ultrasound Treatment with a Multi-directional Transducer," filed on Sep. 16, 2004, having at least one common inventor and a common Assignee as the present application, and also incorporated herein by reference.

Moreover, any variety of mechanical lenses or variable focus lenses, e.g. liquid-filled lenses, may also be used to focus and/or defocus the sound field. For example, with reference to exemplary embodiments depicted in FIGS. 6A and 6B, transducer 600 may also be configured with an electronic focusing array 604 in combination with one or more transduction elements 606 to facilitate increased flexibility in treating ROI 610. Array 604 may be configured in a manner similar to transducer 502. That is, array 604 can be configured as an array of electronic apertures that may be operated by a variety of phases via variable electronic time delays, for example, T1, T2 . . . Tj. By the term "operated," the electronic apertures of array 604 may be manipulated, driven, used, and/or configured to produce and/or deliver energy in a manner corresponding to the phase variation caused by the electronic time delay. For example, these phase variations can be used to deliver defocused beams, planar beams, and/or focused beams, each of which may be used in combination to achieve different physiological effects in ROI 610.

Transduction elements 606 may be configured to be concave, convex, and/or planar. For example, in an exemplary embodiment depicted in FIG. 6A, transduction elements 606 are configured to be concave in order to provide focused energy for treatment of ROI 610. Additional embodiments are disclosed in U.S. patent application Ser. No. 10/944,500, entitled "Variable Depth Transducer System and Method", and again incorporated herein by reference.

Figure 6A:
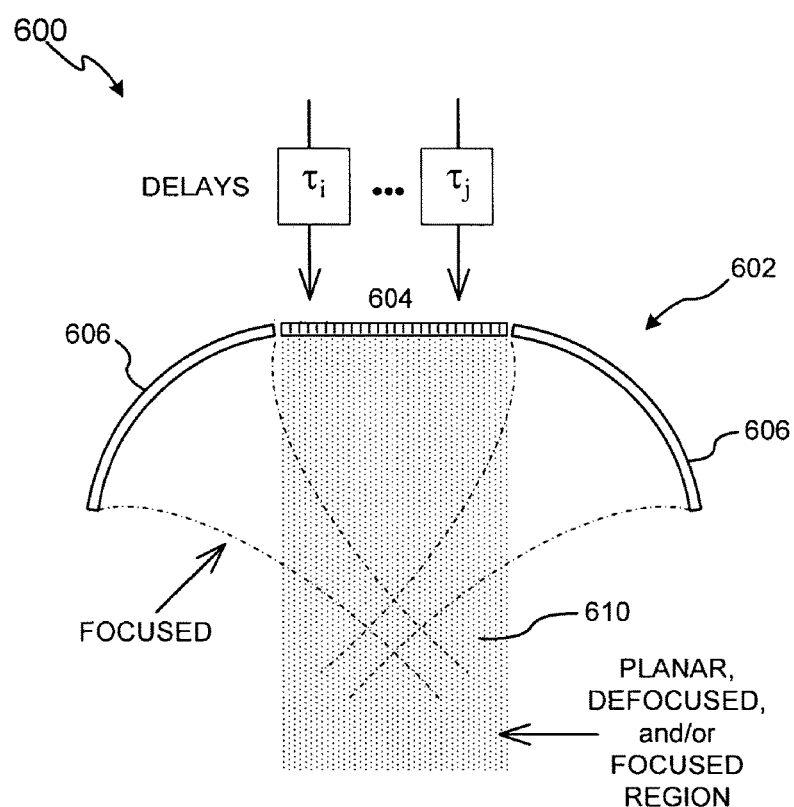
FIGS. 6A and 6B illustrate cross-sectional diagrams of an exemplary transducer in accordance with exemplary embodiments of the present invention.
Figure 6B:
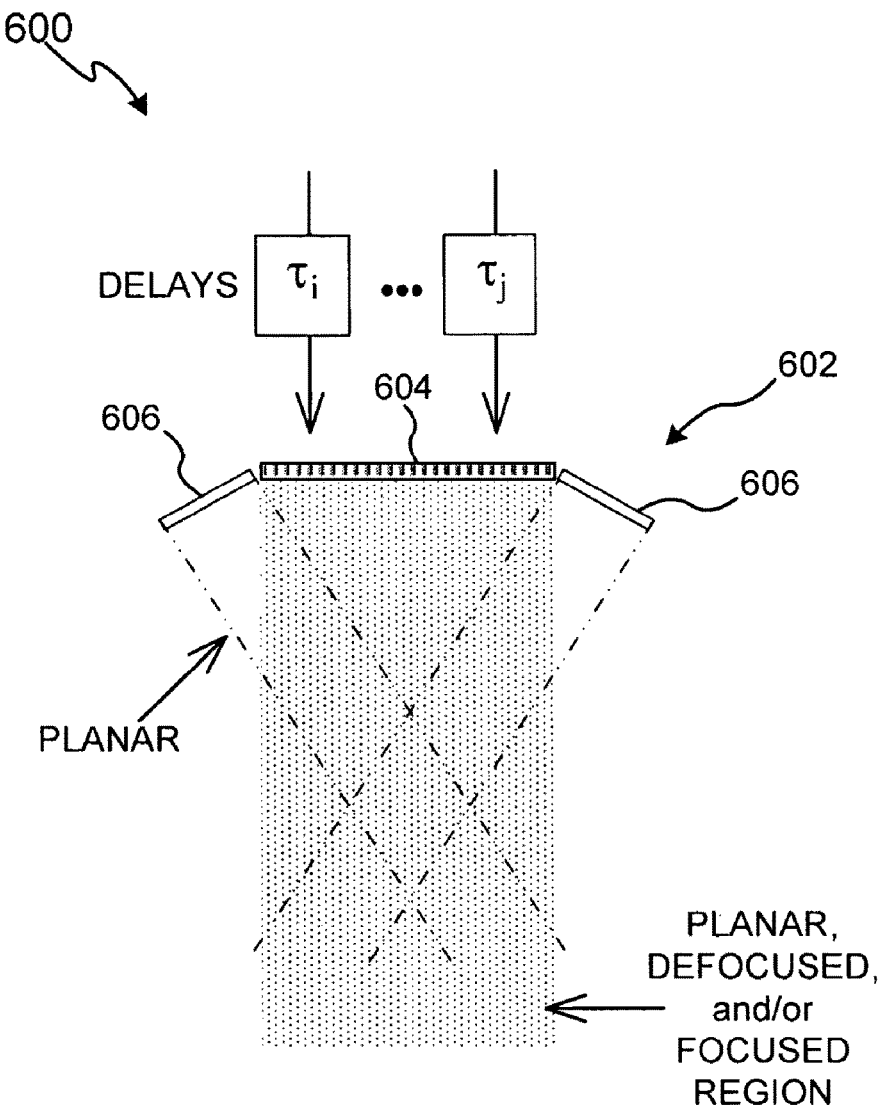

In another exemplary embodiment, depicted in FIG. 68, transduction elements 606 can be configured to be substantially flat in order to provide substantially uniform energy to ROI 610. While FIGS. 6A and 68 depict exemplary embodiments with transduction elements 604 configured as concave and substantially flat, respectively, transduction elements 604 can be configured to be concave, convex, and/or substantially flat. In addition, transduction elements 604 can be configured to be any combination of concave, convex, and/or substantially flat structures. For example, a first transduction element can be configured to be concave, while a second transduction element can be configured to be substantially flat.

Figure 8A:
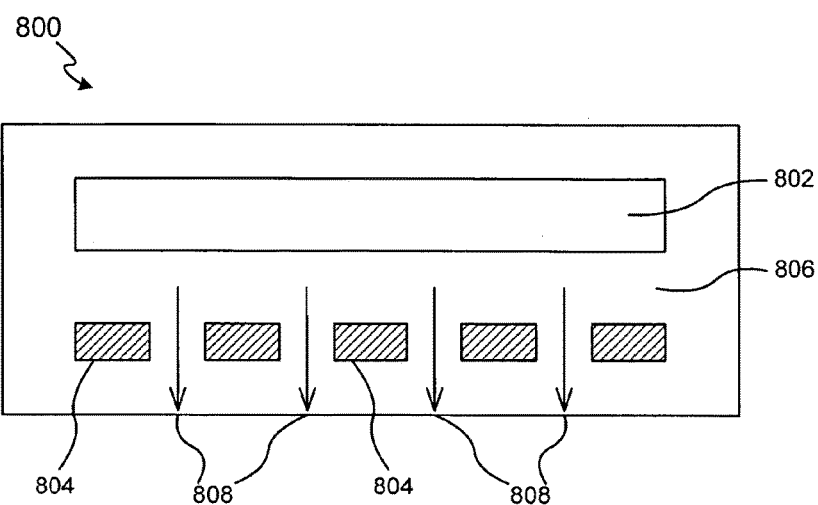
FIGS. 8A and 8B illustrate cross-sectional diagrams of an exemplary transducer in accordance with another exemplary embodiment of the present invention.
Figure 8B:
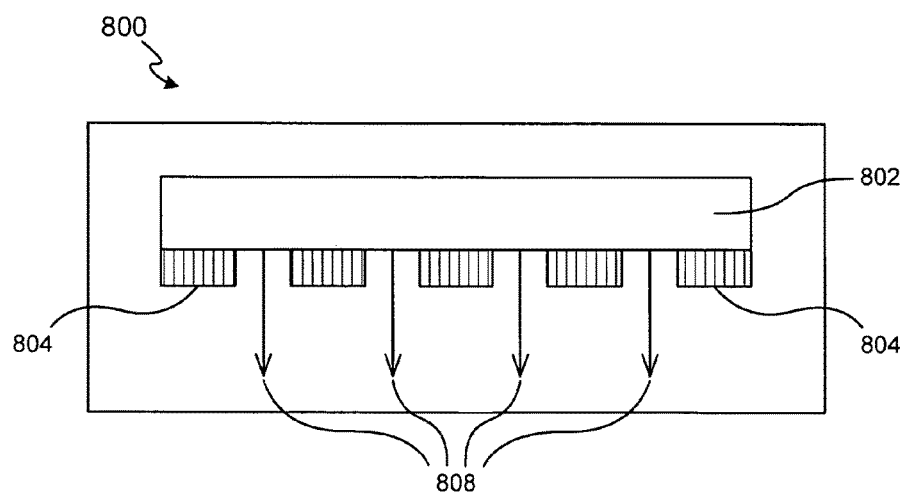

With reference to FIGS. 8A and 8B, transducer 404 can be configured as single-element arrays, wherein a single-element 802, e.g., a transduction element of various structures and materials, can be configured with a plurality of masks 804, such masks comprising ceramic, metal or any other material or structure for masking or altering energy distribution from element 802, creating an array of energy distributions 808. Masks 804 can be coupled directly to element 802 or separated by a standoff 806, such as any suitably solid or liquid material.

Figure 10A:
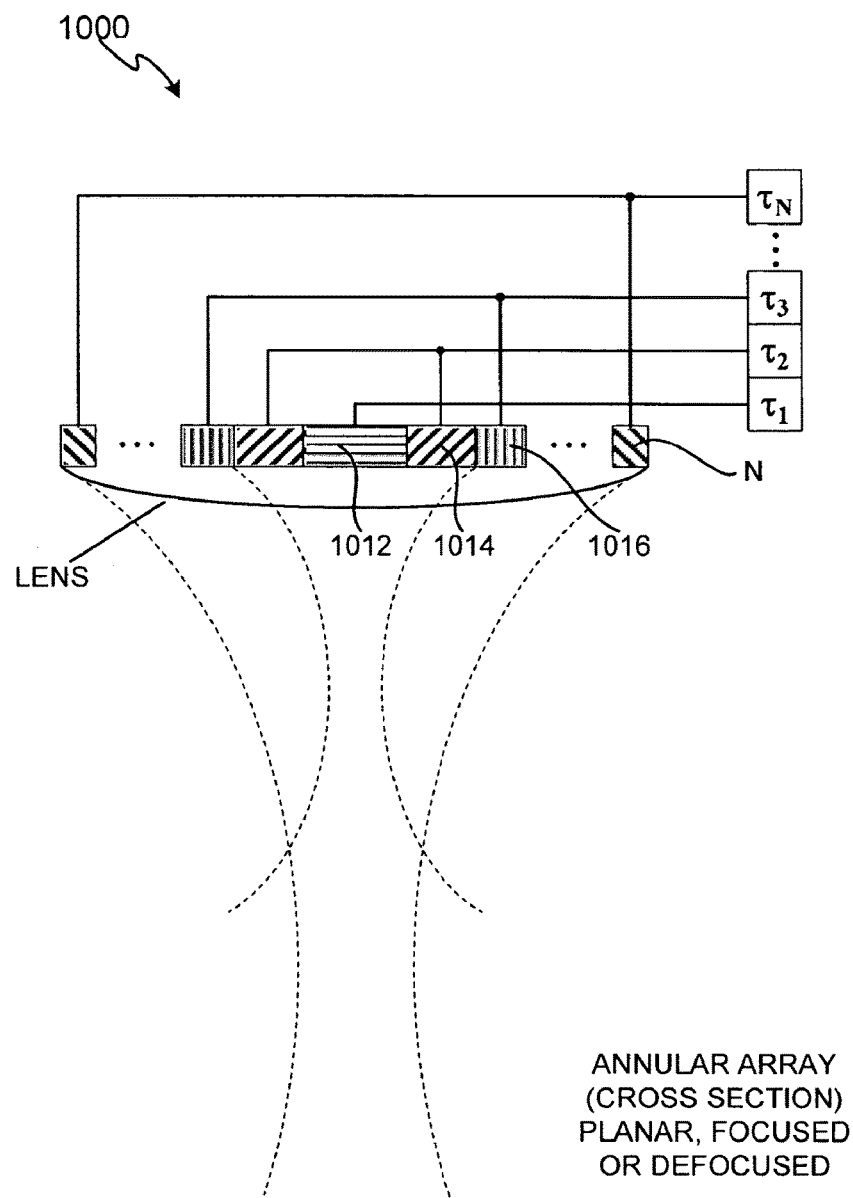
FIGS. 10A-10F illustrate cross-sectional diagrams of exemplary transducers in accordance with other exemplary embodiments of the present invention.
Figure 10B:
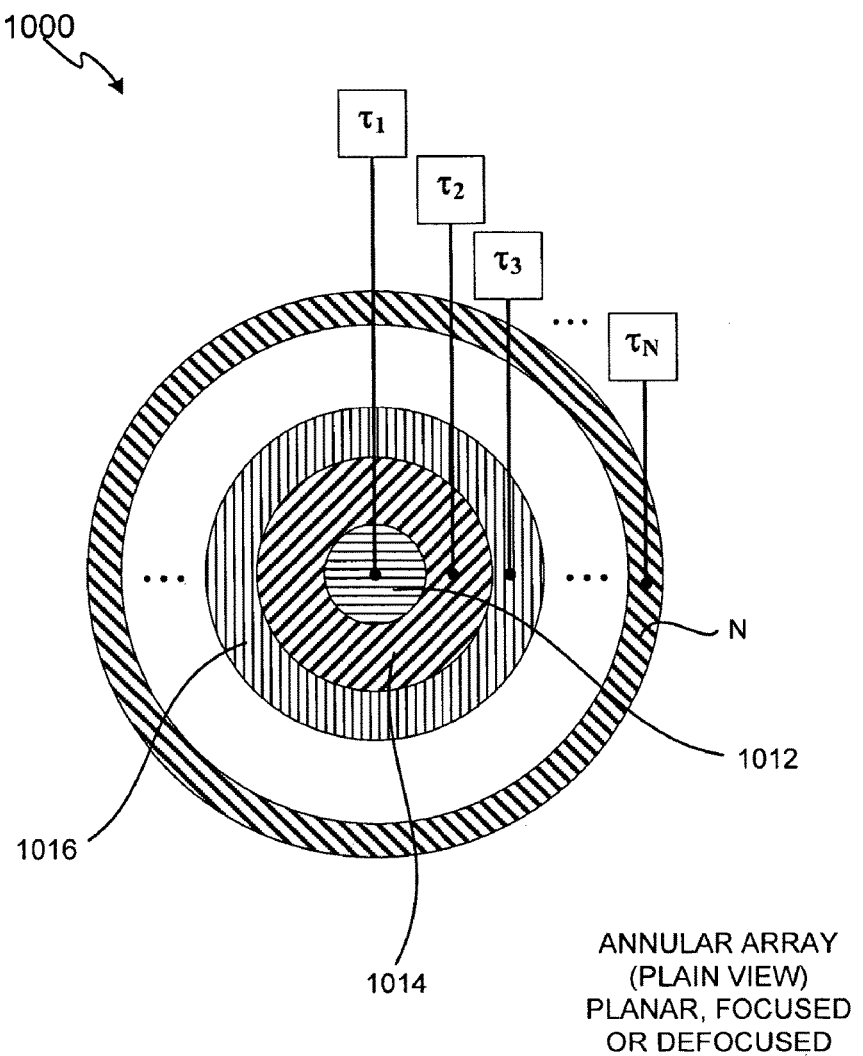
Figure 10C:
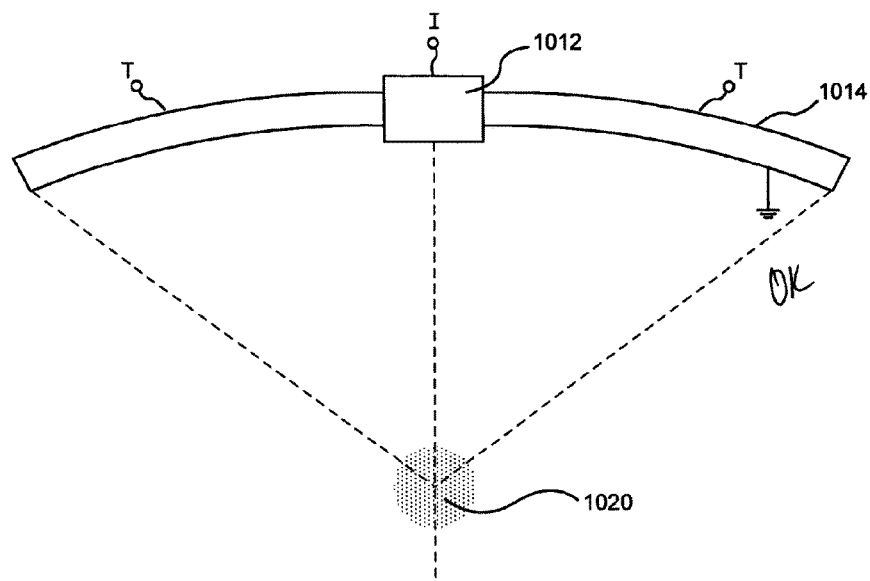
Figure 10D:
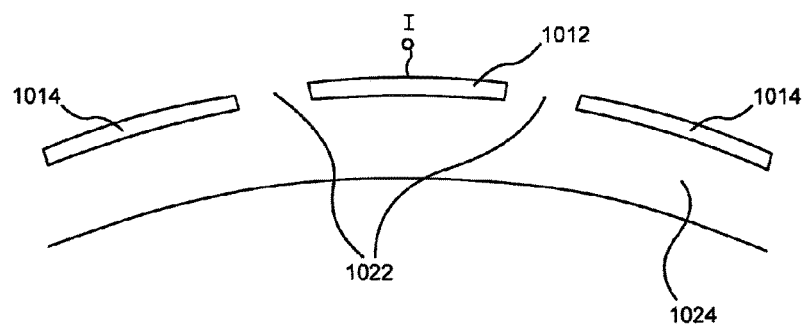
Figure 10E:
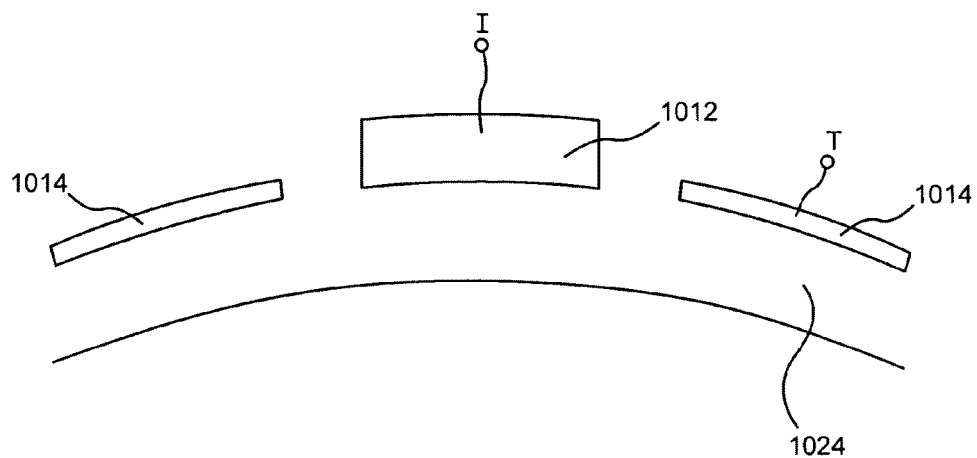

An exemplary transducer 404 can also be configured as an annular array to provide planar, focused and/or defocused acoustical energy. For example, with reference to FIGS. 10A and 10B, in accordance with an exemplary embodiment, an annular array 1000 can comprise a plurality of rings 1012, 1014, 1016 to N. Rings 1012, 1014, 1016 to N can be mechanically and electrically isolated into a set of individual elements, and can create planar, focused, or defocused waves. For example, such waves can be centered on-axis, such as by methods of adjusting corresponding transmit and/or receive delays, T1, T2, T3 . . . TN. An electronic focus can be suitably moved along various depth positions, and can enable variable strength or beam tightness, while an electronic defocus can have varying amounts of defocusing. In accordance with an exemplary embodiment, a lens and/or convex or concave shaped annular array 1000 can also be provided to aid focusing or defocusing such that any time differential delays can be reduced. Movement of annular array 800 in one, two or three-dimensions, or along any path, such as through use of probes and/or any conventional robotic arm mechanisms, may be implemented to scan and/or treat a volume or any corresponding space within a region of interest.

Transducer 404 can also be configured in other annular or non-array configurations for imaging/therapy functions. For example, with reference to FIGS. 10C-10F, a transducer can comprise an imaging element 1012 configured with therapy element(s) 1014. Elements 1012 and 1014 can comprise a single-transduction element, e.g., a combined imaging/transducer element, or separate elements, can be electrically isolated 1022 within the same transduction element or between separate imaging and therapy elements, and/or can comprise standoff 1024 or other matching layers, or any combination thereof. For example, with particular reference to FIG. 10F, a transducer can comprise an imaging element 1012 having a surface 1028 configured for focusing, defocusing or planar energy distribution, with therapy elements 1014 including a stepped-configuration lens configured for focusing, defocusing, or planar energy distribution.

In accordance with various exemplary embodiments of the present invention, transducer 404 may be configured to provide one, two and/or three-dimensional treatment applications for focusing acoustic energy to one or more regions of interest. For example, as discussed above, transducer 404 can be suitably diced to form a one-dimensional array, e.g., transducer 602 comprising a single array of sub-transduction elements.

Figure 9:
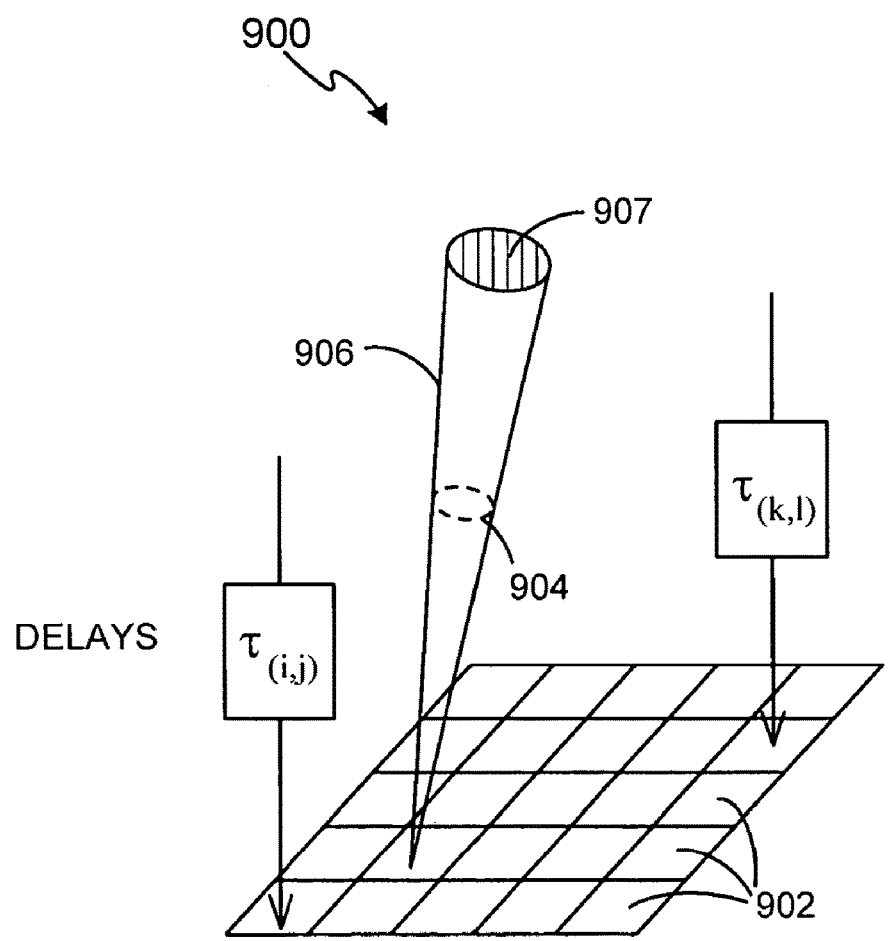
FIG. 9 illustrates an exemplary transducer configured as a two-dimensional, array for ultrasound treatment in accordance with an exemplary embodiment of the present invention.

In accordance with another exemplary embodiment, transducer 404 may be suitably diced in two-dimensions to form a two-dimensional array. For example, with reference to FIG. 9, an exemplary two-dimensional array 900 can be suitably diced into a plurality of two-dimensional portions 902. Two-dimensional portions 902 can be suitably configured to focus on the treatment region at a certain depth, and thus provide respective slices 904, 907 of the treatment region. As a result, the two-dimensional array 900 can provide a two-dimensional slicing of the image place of a treatment region, thus providing two-dimensional treatment.

In accordance with another exemplary embodiment, transducer 404 may be suitably configured to provide three-dimensional treatment. For example, to provide three-dimensional treatment of a region of interest, with reference again to FIG. 1, a three-dimensional system can comprise a transducer within probe 104 configured with an adaptive algorithm, such as, for example, one utilizing three-dimensional graphic software, contained in a control system, such as control system 102. The adaptive algorithm is suitably configured to receive two-dimensional imaging, temperature and/or treatment or other tissue parameter information relating to the region of interest, process the received information, and then provide corresponding three-dimensional imaging, temperature and/or treatment information.

In accordance with an exemplary embodiment, with reference again to FIG. 9, an exemplary three-dimensional system can comprise a two-dimensional array 900 configured with an adaptive algorithm to suitably receive 904 slices from different image planes of the treatment region, process the received information, and then provide volumetric information 906, e.g., three-dimensional imaging, temperature and/or treatment information. Moreover, after processing the received information with the adaptive algorithm, the two-dimensional array 900 may suitably provide therapeutic heating to the volumetric region 906 as desired.

In accordance with other exemplary embodiments, rather than utilizing an adaptive algorithm, such as three-dimensional software, to provide three-dimensional imaging and/or temperature information, an exemplary three-dimensional system can comprise a single transducer 404 configured within a probe arrangement to operate from various rotational and/or translational positions relative to a target region.

Figure 7:
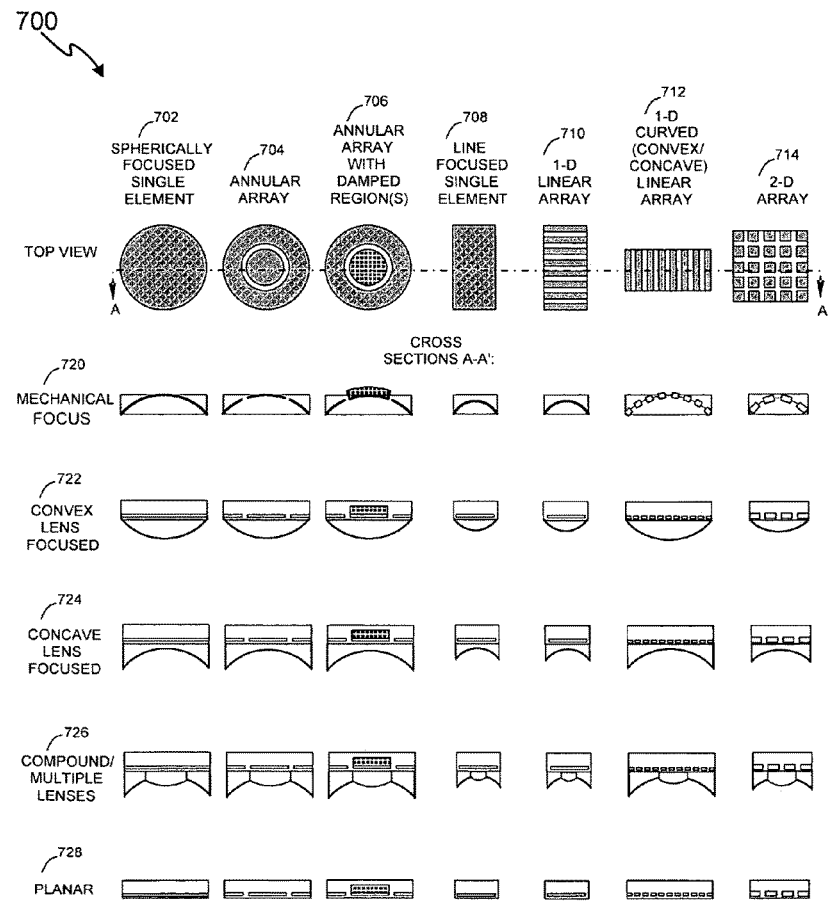
FIG. 7 illustrates exemplary transducer configurations for ultrasound treatment in accordance with various exemplary embodiments of the present invention.
Figure 10F:
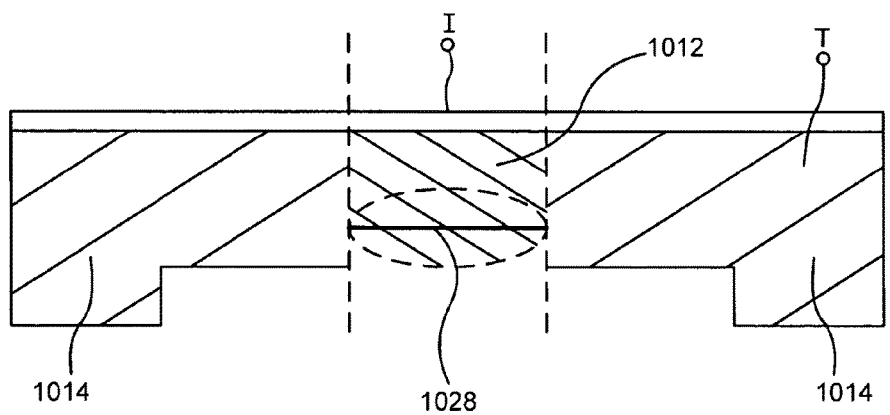

To further illustrate the various structures for transducer 404, with reference to FIG. 7, ultrasound therapy transducer 700 can be configured for a single focus, an array of foci, a locus of foci, a line focus, and/or diffraction patterns. Transducer 700 can also comprise single elements, multiple elements, annular arrays, one-, two-, or three-dimensional arrays, broadband transducers, and/or combinations thereof, with or without lenses, acoustic components, and mechanical and/or electronic focusing. Transducers configured as spherically focused single elements 702, annular arrays 704, annular arrays with damped regions 706, line focused single elements 708, 1-0 linear arrays 710, 1-0 curvilinear arrays in concave or convex form, with or without elevation focusing, 2-D arrays, and 3-D spatial arrangements of transducers may be used to perform therapy and/or imaging and acoustic monitoring functions. For any transducer configuration, focusing and/or defocusing may be in one plane or two planes via mechanical focus 720, convex lens 722, concave lens 724, compound or multiple lenses 726, planar form 728, or stepped form, such as illustrated in FIG. 10F. Any transducer or combination of transducers may be utilized for treatment. For example, an annular transducer may be used with an outer portion dedicated to therapy and the inner disk dedicated to broadband imaging wherein such imaging transducer and therapy transducer have different acoustic lenses and design, such as illustrated in FIG. 1 OC-1 OF.

Moreover, such transduction elements 700 may comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. Transduction elements 700 may also comprise one or more matching layers configured along with the piezoelectrically active material. In addition to or instead of piezoelectrically active material, transduction elements 700 can comprise any other materials configured for generating radiation and/or acoustical energy. A means of transferring energy to and from the transducer to the region of interest is provided.

Figure 12:
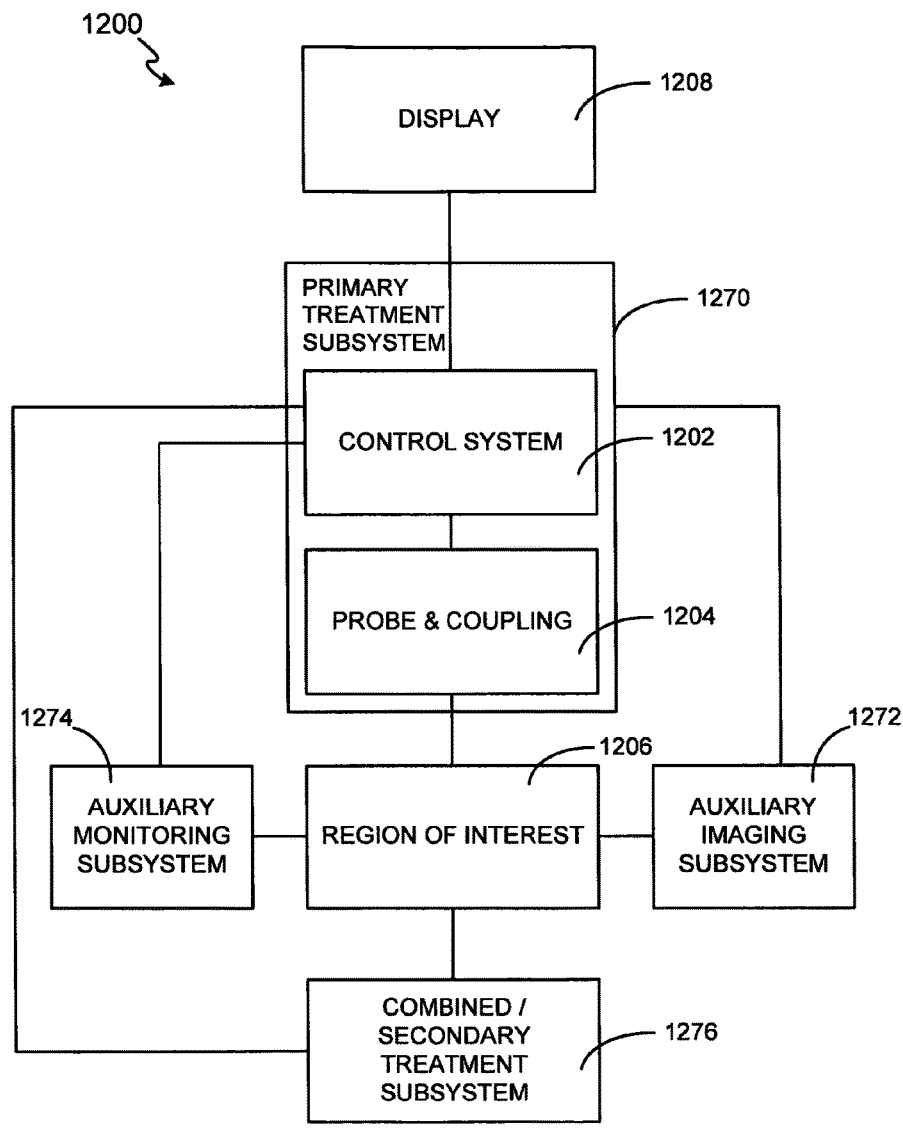
FIG. 12 illustrates a block diagram of an ultrasound treatment system combined with additional subsystems and methods of treatment monitoring and/or treatment imaging as well as a secondary treatment subsystem in accordance with an exemplary embodiment of the present invention.

In accordance with another exemplary embodiment, with reference to FIG. 12, an exemplary treatment system 200 can be configured with and/or combined with various auxiliary systems to provide additional functions. For example, an exemplary treatment system 1200 for treating a region of interest 1202 can comprise a control system 1206, a probe 1204, and a display 1208. Treatment system 1200 further comprises an auxiliary imaging modality 1272 and/or auxiliary monitoring modality 1274 may be based upon at least one of photography and other visual optical methods, magnetic resonance imaging (MRI), computed tomography (CT), optical coherence tomography (OCT), electromagnetic, microwave, or radio frequency (RF) methods, positron emission tomography (PET), infrared, ultrasound, acoustic, or any other suitable method of visualization, localization, or monitoring of epidermal, superficial dermal, mid-dermal and deep dermal components within the region-of-interest 1202, including imaging/monitoring enhancements. Such imaging/monitoring enhancement for ultrasound imaging via probe 1204 and control system 1206 could comprise M-mode, persistence, filtering, color, Doppler, and harmonic imaging among others; furthermore an ultrasound treatment system 1270, as a primary source of treatment, may be combined with a secondary source of treatment 1276, including radio frequency (RF), intense pulsed light (IPL), laser, infrared laser, microwave, or any other suitable energy source.

Figure 13:
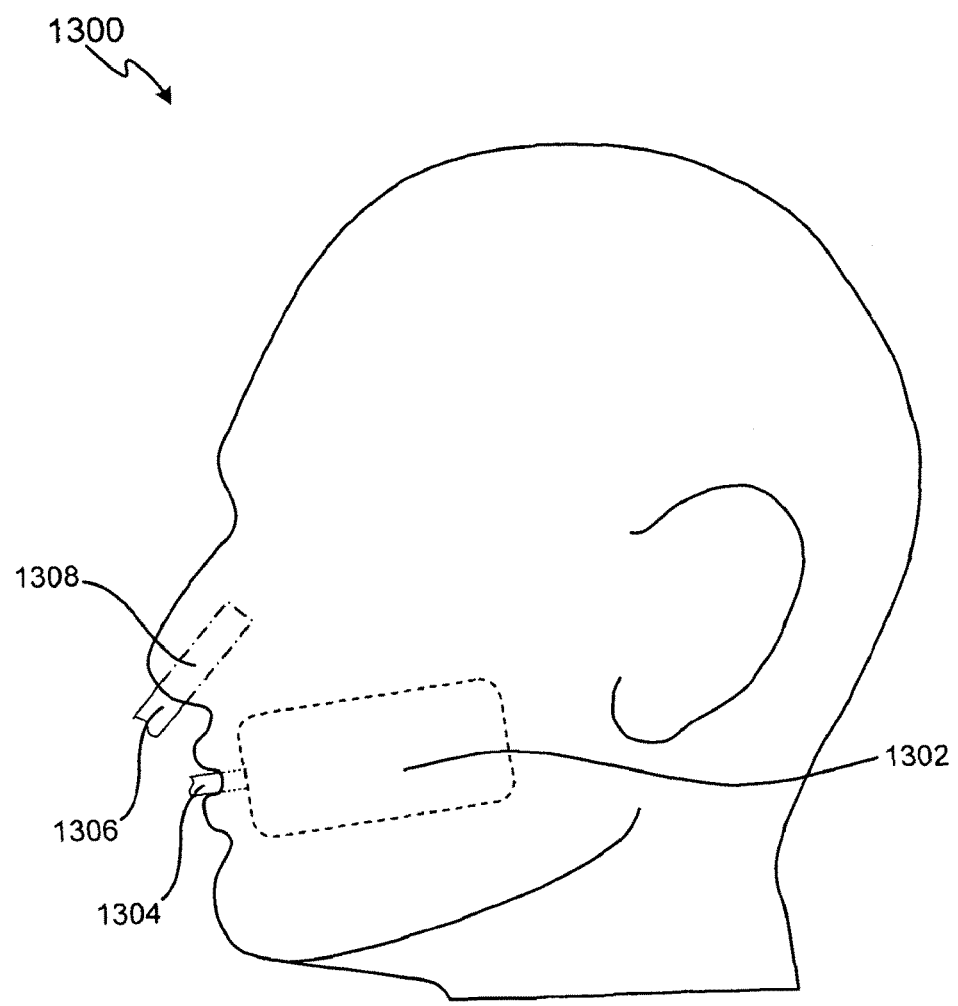
FIG. 13 illustrates a schematic diagram with imaging, therapy, or monitoring being provided with one or more active or passive oral inserts in accordance with an exemplary embodiment of the present invention.

In accordance with another exemplary embodiment, with reference to FIG. 13, treatment composed of imaging, monitoring, and/or therapy to a region of interest 1302 and/or 1308 may be aided, augmented, and/or delivered with passive or active devices 1304 and/or 1306 within the oral and/or nasal cavity, respectively. For example, if passive or active device 1304 and/or 1306 are second transducers or acoustic reflectors acoustically coupled to the mucous membranes it is possible to obtain through transmission, tomographic, or round-trip acoustic waves which are useful for treatment monitoring, such as in measuring acoustic speed of sound and attenuation, which are temperature dependent; furthermore such transducers could be used to treat and/or image. In addition an active, passive, or active/passive object 1304 and/or 1306 may be used to flatten the skin, and/or may be used as an imaging grid, marker, or beacon, to aid determination of position. A passive or active device 1304 and/or 1306 may also be used to aid cooling or temperature control. Natural air in the oral cavity and/or nasal cavity may also be used as passive device 1304 and/or 1306 whereby it may be utilized to as an acoustic reflector to aid thickness measurement and monitoring function.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. These and other changes or modifications are intended to be included within the scope of the present invention, as set forth in the following claims.

What is claimed is:

1. An ultrasound probe for treatment of skin laxity, the ultrasound probe comprising:
   a housing, wherein inside the housing comprises a motion mechanism and an ultrasound transducer,
   wherein the ultrasound transducer comprises a single active focused piezoelectric ultrasound therapy element,
   wherein the piezoelectric ultrasound therapy element is configured to provide a single mechanical focus,
   wherein the single mechanical focus is configured to provide ultrasound therapy energy in a form of a single thermal focus in a tissue at a depth below a skin surface,
   wherein the depth is a single, fixed depth below the skin surface to treat the tissue,
   wherein the tissue comprises any of the group consisting of: an epidermal tissue, a superficial dermal tissue, a mid-dermal tissue, a deep dermal tissue, a muscle tissue, and an adipose tissue,
      wherein the single thermal focus is formed without electronic focusing and without a lens,
   wherein a portion of the housing is configured for acoustic coupling to the skin surface;
   wherein the piezoelectric ultrasound therapy element is configured for delivery of energy at a temperature sufficient to tighten at least a portion of the tissue at the depth under the skin surface,
   wherein the piezoelectric ultrasound therapy element is connected to the motion mechanism,
   wherein the motion mechanism is configured to operate with an encoder,
   wherein the motion mechanism is configured to move the piezoelectric ultrasound therapy element to form a plurality of thermal lesions at the depth for tightening at least a portion of the tissue for reducing skin laxity.

2. The ultrasound probe of claim 1, wherein the ultrasound probe is disposable,
   wherein the piezoelectric ultrasound therapy element is configured to increase the temperature of the tissue in the region of interest to greater than 60° C.,
   wherein the piezoelectric ultrasound therapy element is a single element that delivers ultrasound energy at a frequency of between 2 MHz to 25 MHz.

3. The ultrasound probe of claim 1, further comprising a piezoelectric ultrasound imaging element co-housed with the piezoelectric ultrasound therapy element.

4. The ultrasound probe of claim 1, wherein the ultrasound probe is reusable, wherein the housing is configured for connection to a control system,
wherein the control system comprises a microprocessor and a communication device,
wherein the ultrasound transducer is electrically connected to the control system via a cable.

5. The ultrasound probe of claim 1, further comprising an EEPROM to store and record probe identification and usage history,
wherein the ultrasound therapy energy is configured to deliver an energy level for causing at least one of shrinking collagen and denaturing the tissue in the region of interest proximate a wrinkle,
wherein the piezoelectric ultrasound therapy element delivers the ultrasound therapy energy at a frequency of between 2 MHz to 25 MHz.

6. The ultrasound probe of claim 1, wherein the piezoelectric ultrasound therapy element is configured to connect to a control system and a power supply,
wherein the control system is connected to the motion mechanism, the piezoelectric ultrasound therapy element, and a power supply,
wherein the power supply is connected to the control system,
wherein the control system comprises a spatial control and a temporal control,
wherein the spatial control and the temporal control are configured for controlling the delivery of energy at a temperature sufficient to cause denaturation of at least the portion of the tissue at the depth under the skin surface,
wherein the spatial control and the temporal control are configured for controlling the delivery of energy at a frequency of between 2 MHz to 25 MHz.

7. An ultrasound probe for treatment of skin laxity, the ultrasound probe comprising:
an ultrasound transducer within a housing, the ultrasound transducer being configured for delivery of an ultrasound therapy energy at a temperature sufficient to heat at least a portion of a tissue at a depth under a skin surface,
wherein the tissue comprises any one or more of the group consisting of: an epidermal tissue, a superficial dermal tissue, a mid-dermal tissue, a deep dermal tissue, a muscle tissue, and an adipose tissue;
wherein the ultrasound transducer comprises a single active piezoelectric ultrasound therapy element,
wherein the single active piezoelectric ultrasound therapy element is configured to provide a single mechanical focus,
wherein the single mechanical focus is configured to provide ultrasound therapy energy in the form of a single thermal focus in the tissue at a depth below a skin surface,
wherein the single thermal focus is formed without electronic focusing and without a lens,
wherein the piezoelectric ultrasound therapy element is configured for delivery of the ultrasound therapy energy at the temperature sufficient to heat the at least a portion of the tissue at the depth under the skin surface,
wherein the ultrasound transducer forms a plurality of thermal lesions at the depth for reducing the appearance of skin laxity.

8. The ultrasound probe of claim 7, further comprising a storage system comprising probe identification and probe usage history, wherein the region of interest comprises the tissue, wherein the skin surface comprises a wrinkle, and wherein the plurality of thermal lesions tightens the tissue.

9. The ultrasound probe of claim 7, further comprising a piezoelectric ultrasound imaging element co-housed with the piezoelectric ultrasound therapy element, wherein the piezoelectric ultrasound therapy element delivers the ultrasound therapy energy at a frequency of between 2 MHz to 50 MHz.

10. The ultrasound probe of claim 7, wherein the ultrasound probe is reusable, wherein the piezoelectric ultrasound therapy element is configured for communication with a control system, wherein the ultrasound transducer is connected to the control system via a cable, and wherein the control system comprises:
a communication device;
a processor, software, an input device, and a power supply.

11. The ultrasound probe of claim 7,
wherein the piezoelectric ultrasound therapy element is a single element that delivers the ultrasound therapy energy at a frequency of between 2 MHz to 25 MHz,
wherein the piezoelectric ultrasound therapy element is configured to increase the temperature of the tissue in the region of interest to greater than 60° C.,
wherein the ultrasound probe is disposable,
and wherein the ultrasound probe comprises a storage system for transducer usage history and calibration.

12. An ultrasound probe for treatment of skin laxity, the ultrasound probe comprising:
a housing and an ultrasound transducer, wherein the ultrasound transducer is inside the housing,
wherein the ultrasound transducer comprises a single active focused piezoelectric ultrasound therapy element,
wherein the piezoelectric ultrasound therapy element is configured to provide a single mechanical focus,
wherein the single mechanical focus is configured to provide ultrasound therapy energy in the form of a single thermal focus in a tissue at a depth below a skin surface,
wherein the depth is up to 5 mm below the skin surface,
wherein the tissue comprises any of the group consisting of: an epidermal tissue, a superficial dermal tissue, a mid-dermal tissue, a deep dermal tissue, an adipose tissue, and a muscle tissue,
wherein the single thermal focus is formed without electronic focusing and without a lens,
wherein the piezoelectric ultrasound therapy element is configured for delivery of the ultrasound therapy energy at a temperature sufficient to denature at least a portion of the tissue in the region of interest at a depth under the skin surface,
wherein the piezoelectric ultrasound therapy element forms a plurality of thermal lesions at the depth for tightening the tissue for reducing skin laxity.

13. The ultrasound probe of claim 12, further comprising a control system and a power supply;
wherein the ultrasound therapy element is in communication with the control system,
wherein the ultrasound transducer is connected to the control system via a cable,
wherein the skin surface comprises a wrinkle.

14. The ultrasound probe of claim 12, further comprising an acoustic coupler between the ultrasound transducer and the skin surface, wherein the piezoelectric ultrasound therapy element is a single element that delivers ultrasound energy at a frequency of between 2 MHz to 25 MHz.

15. The ultrasound probe of claim 12, wherein the ultrasound probe is disposable, wherein the piezoelectric ultrasound therapy element is configured to increase the temperature of the tissue in a region of interest to greater than 60° C.

16. The ultrasound probe of claim 12, further comprising a storage system and a piezoelectric ultrasound imaging element, wherein the storage system records probe usage history, and wherein the piezoelectric ultrasound imaging element is co-housed with the piezoelectric ultrasound therapy element in the housing.

17. The ultrasound probe of claim 12, further comprising a monitoring system, wherein the monitoring system is configured to monitor a treatment parameter, wherein the treatment parameter measured comprises a temperature of the tissue below the skin surface.

18. The ultrasound probe of claim 12, further comprising a motion mechanism configured to operate with an encoder, wherein the motion mechanism is configured for movement of the piezoelectric ultrasound therapy element to form a plurality of thermal lesions at the depth in the region of interest.

19. The ultrasound probe of claim 12, further comprising a motion mechanism configured to operate with an encoder, wherein the motion mechanism is configured for any one of the group consisting of linear, rotational, and variable movement of the piezoelectric ultrasound therapy element.

20. The ultrasound probe of claim 12, further comprising a motion mechanism configured to operate with an encoder for monitoring a position of the ultrasound therapy element,
  wherein the piezoelectric ultrasound therapy element is a single element that delivers the ultrasound therapy energy at a frequency of between 2 MHz to 25 MHz,
  wherein the piezoelectric ultrasound therapy element is configured to deliver the ultrasound therapy energy at the depth below the skin surface.

* * * * *